United States Patent
Bös et al.

(10) Patent No.: US 6,479,483 B2
(45) Date of Patent: Nov. 12, 2002

(54) 4-PHENYL-PYRIDINE DERIVATIVES

(75) Inventors: Michael Bös, Montreal (CA); Quirico Branca, Binningen (CH); Guido Galley, Rheinfelden (DE); Thierry Godel, Basle (CH); Torsten Hoffmann, Birsfelden (CH); Walter Hunkeler, Magden (CH); Patrick Schnider, Oberwil (CH); Heinz Stadler, Rheinfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/901,982

(22) Filed: Jul. 10, 2001

(65) Prior Publication Data

US 2002/0091265 A1 Jul. 11, 2002

Related U.S. Application Data

(62) Division of application No. 09/507,456, filed on Feb. 22, 2000.

(30) Foreign Application Priority Data

Feb. 24, 1999 (EP) ............................................. 99103504
Nov. 29, 1999 (EP) ............................................. 99123689

(51) Int. Cl.[7] .................. C07D 213/82; C07D 401/12; C07D 413/12; A61P 25/00; A61K 31/44
(52) U.S. Cl. .................. 514/227.8; 544/365; 544/58.2; 544/58.6; 514/253.13; 514/355; 546/316
(58) Field of Search .............................. 544/365, 58.2, 544/58.6; 514/253.13, 355, 227.8; 546/316

(56) References Cited

U.S. PATENT DOCUMENTS

| | | | |
|---|---|---|---|
| 4,764,361 A | 8/1988 | Bilski et al. | 424/45 |
| 5,387,595 A | 2/1995 | Mills et al. | 514/357 |
| 5,554,633 A | 9/1996 | Teall | 514/357 |
| 5,612,337 A | 3/1997 | Baker et al. | 514/236.2 |
| 5,719,147 A | 2/1998 | Dorn et al. | 514/227.5 |
| 5,972,938 A | 10/1999 | Rupniak | 514/236.2 |
| 6,294,537 B1 | 9/2001 | Bichon et al. | 514/252 |

FOREIGN PATENT DOCUMENTS

| | | |
|---|---|---|
| EP | 089 765 | 9/1983 |
| EP | 244 937 | 3/1987 |
| EP | 0 235 663 | 9/1987 |
| EP | 244 080 | 11/1987 |
| EP | 359 547 | 3/1990 |
| EP | 385 350 | 9/1990 |
| EP | 405 931 | 1/1991 |
| EP | 427 526 | 5/1991 |
| EP | 524 781 | 1/1993 |
| EP | 638 557 | 2/1995 |
| EP | 0 733 632 | 9/1996 |
| GB | 1 557 420 | 12/1979 |
| KR | 8101320 | 10/1981 |
| KR | 8101697 | 10/1981 |
| WO | WO 92/06080 | 4/1992 |
| WO | WO 93/11110 | 6/1993 |
| WO | WO 94/21611 | 9/1994 |
| WO | WO 95/16679 | 6/1995 |
| WO | WO 95/18124 | 7/1995 |
| WO | WO 95/23798 | 9/1995 |
| WO | WO 95/33744 | 12/1996 |
| WO | WO 97/36871 | 10/1997 |
| WO | WO 98/21185 | 5/1998 |

OTHER PUBLICATIONS

Barker, Rviews in the Neurosciences, vol. 7, No. 3. pp. 187–214 (1996).
Longmore etal., Can. J. Physiol. Pharmacol., vol. 75, pp. 612–621 (1977).
Kramer et al., Science, vol. 281, pp. 1640–1645 (1998).
Maggi et al., J. Auton Pharmacol., vol. 13, pp. 23–93 (1993).
Navari et al., New England Journal of Medicine, vol. 340(3), pp. 190–195 (1999).
Abstract corresponding to WO 96/00213.
Abstract corresponding to WO 94/27604.
Ikeura et al., Chem. Phar. Bull., vol. 45(10), pp. 1642–1652 (1997).
Natsurgari et al., J. Med. Chem., vol. 38(16), pp. 3106–3120 (1995).
Abstract corresponding to WO/98/21185.

*Primary Examiner*—Mukund J. Shah
*Assistant Examiner*—Hong Liu
(74) *Attorney, Agent, or Firm*—Geroge W. Johnston; Patricia S. Rocha-Tramaloni; Arthur D. Dawson

(57) ABSTRACT

Compounds of the present invention are 4-phenyl-pyridine derivatives with activity as NK-1 receptor antagonists.

34 Claims, No Drawings

4-PHENYL-PYRIDINE DERIVATIVES

This is a divisional of prior application Ser. No. 09/507,456 filing date Feb. 22, 2000.

BACKGROUND OF THE INVENTION

Substance P is a naturally occurring undecapeptide belonging to the tachykinin family of peptides, the latter being so-named because of their prompt contractile action on extravascular smooth muscle tissue. The receptor for substance P is a member of the superfamily of G protein-coupled receptors.

The neuropeptide receptor for substance P (NK-1) is widely distributed throughout the mammalian nervous system (especially brain and spinal ganglia), the circulatory system and peripheral tissues (especially the duodenum and jejunum) and are involved in regulating a number of diverse biological processes.

The central and peripheral actions of the mammalian tachykinin substance P have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease (Neurosci. Res., 1996, 7, 187–214), anxiety (Can. J. Phys., 1997, 75, 612–621) and depression (Science, 1998, 281, 1640–1645).

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases reviewed in "Tachykinin Receptor and Tachykinin Receptor Antagonists", J. Auton. Pharmnacol., 13, 23–93, 1993.

Neurokinin 1 receptor antagonists are being developed for the treatment of a number of physiological disorders associated with an excess or imbalance of tachykinin, in particular substance P. Examples of conditions in which substance P has been implicated include disorders of the central nervous system such as anxiety, depression and psychosis (WO 95/16679, WO 95/18124 and WO 95/23798).

The neurokinin-1 receptor antagonists are further useful for the treatment of motion sickness and for treatment induced vomiting. The New England Journal of Medicine, Vol. 340, No. 3 190–195, 1999 has been described the reduction of cisplatin-induced emesis by a selective neurokinin-1-receptor antagonist. U.S. Pat. No. 5,972,938 describes a method for treating a psychoimmunologic or a psychosomatic disorder by administration of a tachykinin receptor, such as NK-1 receptor antagonist.

SUMMARY OF THE INVENTION

This invention relates to compounds of the general formula

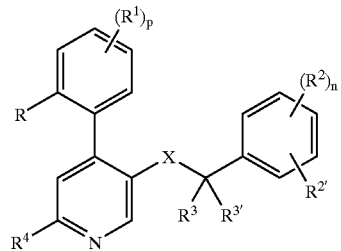

I wherein
R is lower alkyl, lower alkoxy, halogen or trifluoromethyl;
$R^1$ is halogen or hydrogen; and when p is 1, $R^1$ may in addition to the above substituents be taken together with R to form —CH=CH—CH=CH—
$R^2$ and $R^{2'}$ are independently hydrogen, halogen, trifluoromethyl, lower alkoxy or cyano;
and when n is 1, $R^2$ and $R^{2'}$ may in addition to the above substituents form —CH=CH—CH=CH—, unsubstituted or substituted by one or two substituents selected from lower alkyl or lower alkoxy,
$R^3$ and $R^{3'}$ are hydrogen, lower alkyl or taken together with the attached carbon atom form a cycloalkyl group;
$R^4$ is hydrogen, —N($R^5$)$_2$, —N($R^5$)(CH$_2$)$_n$OH, —N($R^5$)S(O)$_2$-lower alkyl, —N($R^5$)S(O)$_2$-phenyl, —N=CH—N($R^5$)$_2$, —N($R^5$)C(O)$R^5$,

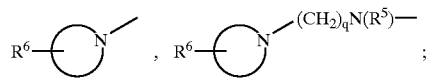

$R^5$ is hydrogen, $C_{3-6}$-cycloalkyl, benzyl or lower alkyl;
$R^6$ is hydrogen, hydroxy, lower alkyl, —(CH$_2$)$_n$COO—($R^5$), —N($R^5$)CO—lower alkyl, hydroxy-lower alkyl, —(CH$_2$)$_n$CN, —(CH$_2$)$_n$O(CH$_2$)$_n$OH, —CHO or a 5-or 6 membered heterocyclic ring containing from 1 to 4 heteroatoms, selected from the group consisting of oxygen, nitrogen, and sulfur, and with one of the carbon atoms in said ring being unsubstituted or substituted with an oxo group, which hetercyclic ring is directly bonded or bonded via an alkylene group to the remainder of the molecule;

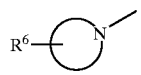

is a cyclic tertiary amine which may contain one additional heteroatom selected from the group consisting of oxygen, nitrogen, or sulfur, wherein any sulfur present in the ring is thio or can be oxidized to sulfoxide or sulfur dioxide by which said cyclic tertiary amine is directly attached to the remainder of the molecule or is attached through the linker —(CH$_2$)$_n$N($R^5$)—;
X is —C(O)N($R^5$)—, —(CH$_2$)$_m$O—, —(CH$_2$)$_m$N($R^5$)—, —N($R^5$)C(O)—, or —N($R^5$)(CH$_2$)$_m$—;
n, p and q are 1 to 4; and
m is 1 or 2;
and pharmaceutically acceptable acid addition salts thereof, which are antagonists of the Neurokinin 1 (NK-1, substance P) receptor.

This invention includes compounds and pharmaceutically acceptable salts thereof, the preparation of the above-mentioned compounds, medicaments containing them and their manufacture as well as the use of the above-mentioned compounds in the control or prevention of symptoms associated with certain conditions and diseases.

The following definitions of the general terms used in the present description apply irrespective of whether the terms in question appear alone or in combination.

As used herein, the term "lower alkyl" denotes a straight- or branched-chain alkyl group containing from 1–7 carbon atoms, for example, methyl, ethyl, propyl, isopropyl, n-butyl, i-butyl, t-butyl and the like. Preferred lower alkyl groups are groups with 1–4 carbon atoms.

The term "lower alkoxy" denotes a group wherein the alkyl residues are as defined above, and which is attached via an oxygen atom.

The term "halogen" denotes chlorine, iodine, fluorine and bromine.

The term "cycloalkyl" denotes a saturated carbocyclic group (e.g. a nonaromatic ring), preferably containing 3–6 carbon atoms (i.e. $C_3$–$C_6$ cycloalkyl).

A "cyclic tertiary amine" denotes a ring system which may contain one additional heteroatom selected from the group consisting of oxygen, nitrogen, or sulfur, wherein any sulfur present in the ring is thio or can be oxidized to sulfoxide or sulfur dioxide by which said cyclic tertiary amine, which ring is directly attached via the ring nitrogen to the remainder of the molecule or is attached through the linker —$(CH_2)_nN(R^5)$—.

The cyclic tertiary amine may contain three to five carbon atoms. When the ring is substituted it is preferably substituted at the heteroatom, for example N-alkyl-piperazine. Examples of such rings include pyrrol-1-yl, imidazol-1-yl, piperidin-1-yl, piperazin-1-yl, morpholin-4-yl, thiomorpholin-4-yl, 1-oxo-thiomorpholin-4-yl or 1,1-dioxo-thiomorpholin-4-yl.

When $R^4$ is substituted (as in for example "substituted piperazinyl"), the substituent is $R^6$, as defined above.

The term a "5-or 6 membered hetercyclic ring" is a ring system, which contains from 1 to 4 heteroatoms, selected from the group consisting of oxygen, nitrogen, and sulfur, and with one of the carbon atoms in said ring being unsubstituted or substituted with an oxo group. Examples of such rings are pyrimidine, oxadiazole, triazole, tetrazole, pyridine, thiazole, thiene, furane, pyrane, pyrrole, imidazole, pyrazole, isothiazole, piperazine or piperidine.

When $R^6$ is $R^{6'}$ (a 5 or 6 membered heterocyclic ring) is bonded via an alkylene group to the remainder of the molecule, this phrase designates the substituent $R^{6'}$ linked to a $CH_2$ (for example) linked to the

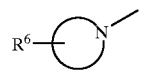

ring, e.g.

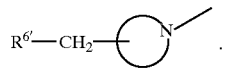

The term "alkylene" denotes a lower alkyl linker which is bound to a group at either end.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

Compounds of this invention are NK-1 receptor antagonists and, as such, are particularly useful for treating depression and pain, especially that resulting from inflammatory conditions such as migraine, rheumatoid arthritis, asthma, and inflammatory bowel disease or resulting from central nervous system (CNS) disorders such as Parkinson's disease or Alzheimer's disease.

Furthermore, the compounds of this invention are useful as agent against headache, anxiety, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases.

The compounds of formula I are further useful for the treatment of motion sickness and emesis.

Thus the most preferred indications in accordance with the present invention are those which include disorders of the central nervous system, for example indications for the treatment or prevention of certain depressive disorders, anxiety or emesis by the administration of NK-1 receptor antagonists. A major depressive episode has been defined as being a period of at least two weeks during which, for most of the day and nearly every day, there is either depressed mood or the loss of interest or pleasure in all, or nearly all activities.

DETAILED DESCRIPTION OF THE INVENTION

Accordingly this invention is directed to the NK-1 receptor antagonists of formula 1.

Preferred compounds of this invention include compounds of formula I where R is lower alkyl, lower alkoxy, halogen or trifluoromethyl and $R^1$ is halogen or hydrogen, or compounds where $R^2$ and $R^{2'}$ are independently hydrogen, halogen, trifluoromethyl, lower alkoxy or cyano.

Particularly preferred are compounds where R, $R^1$, $R^2$, and $R^{2'}$ are as described immediately above (i.e. R is lower alkyl, lower alkoxy, halogen or trifluoromethyl, $R^1$ is halogen or hydrogen, and $R^2$ and $R^{2'}$ are independently hydrogen, halogen, trifluoromethyl, lower alkoxy or cyano).

In some of these particularly preferred compounds, X is $N(R^5)C(O)$—.

Examples of these particularly preferred compounds where $R^4$ is hydrogen are 2-(3,5-Bis-trifluoromethyl-phenyl)-N-[4-(2-chloro-phenyl)-pyridin-3-yl]-N-methyl-isobutyramide, 2-(3,5-Bis-trifluoromethyl-phenyl-N-methyl-N-(4-o-tolyl-pyridin-3-yl)-isobutyramide, 2-(3,5-Bis-trifluoromethyl-phenyl)-N-(4-o-tolyl-pyridin-3-yl)-isobutyramide, 2-(3,5-Bis-trifluoromethyl-phenyl)-N-methyl-N-(4-o-tolyl-pyridin-3-yl)-acetamide, 2-(3,5-Bis-trifluoromethyl-phenyl)-N-methyl-N-(4-o-tolyl-pyridin-3-yl)-propionamide, 1-(3,5-Bis-trifluoromethyl-phenyl)-cyclopropanecarboxylic acid [4-(2-chloro-phenyl)-pyridin-3-yl]-methyl-amide.

In other such particularly preferred compounds where X is $N(R^5)C(O)$—, $R^4$ is

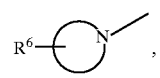

preferably a five-membered or a six-membered tertiary amine ring, for example unsubstituted or substituted piperazinyl, morpholino, thiomorpholino, piperidinyl, or pyrrolidinyl. Examples of the piperazinyl compounds are 2-(3,5-Bis-trifluoromethyl-phenyl)-N-methyl-N-[6-(4-methyl-piperazin-1-yl)-4-o-tolyl-pyridin-3-yl]-isobutyramide, 2-(3,5-bis-trifluoromethyl-phenyl)-N-[4-(2-chloro-phenyl)-6-(4-methyl-piperazin-1-yl)-pyridin-3-yl]-N-methyl-isobutyramide, 2-(3,5-Bis-trifluoromethyl-phenyl)-N-[4-(4-fluoro-2-methyl-phenyl)-6-(4-methyl-piperazin-1-yl)-pyridin-3-yl]-N-methyl-isobutyramide, 2-(3,5-Bis-trifluoromethyl-phenyl)-N-methyl-N-[6-(4-pyrimidin-2-yl-piperazin-1-yl)-4-o-tolyl-pyridin-3-yl]-isobutyramide, 2-(3,5-Bis-trifluoromethyl-phenyl)-N-methyl-N-(6-piperazin-1-yl-4-o-tolyl-pyridin-3-yl)-isobutyramide, [2-(3,5-Bis-trifluoromethyl-phenyl)-2-methyl-propyl]-[4-(4-fluoro-2-methyl-phenyl)-6-(4-methyl-piperazin-1-yl)-pyridin-3-yl]-methyl-amine.

Examples of morpholino compounds are 2-(3,5-Bis-trifluoromethyl-phenyl)-N-methyl-N-(6-morpholin-4-yl-4-o-tolyl-pyridin-3-yl)-isobutyramide, 2-(3,5-Bis-trifluoromethyl-phenyl)-N-[4-(2-chloro-phenyl)-6-morpholin-4-yl-pyridin-3-yl]-N-methyl-isobutyramide, 2-(3,5-Bis-trifluoromethyl-phenyl)-N-(6-morpholin-4-yl-4-o-tolyl-pyridin-3-yl)-isobutyramide, 2-(3,5-Bis-trifluoromethyl-phenyl)-N-methyl-N-(6-morpholin-4-yl-4-o-tolyl-pyridin-3-yl)-acetamide, 2-(3,5-Dimethoxy-phenyl)-N-methyl-N-(6-morpholin-4-yl-4-o-tolyl-pyridin-3-yl)-acetamide, 2-(3-Fluoro-5-trifluoromethyl-phenyl)-N-methyl-N-(6-morpholin-4-yl-4-o-tolyl-pyridin-3-yl)-acetamide.

Examples of unsubstituted or substituted piperidinyl compounds are 2-(3,5-bis-trifluoromethyl-phenyl)-N-[4'-(2-chloro-phenyl)-3,4,5,6-tetrahydro-2H-[1,2']bipyridinyl-5'-yl]-N-methyl-isobutyramide and 2-(3,5-bis-trifluoromethyl-phenyl)-N-[4'-(2-chloro-phenyl)-3,4,5,6-tetrahydro-2H-[1,2']bipyridinyl-5'-yl]-N-methyl-isobutyramide.

An example of a pyrrolidinyl compound is 2-(3,5-bis-trifluoromethyl-phenyl)-N-{6-[(2-hydroxy-ethyl)-methyl-amino]-4-6-tolyl-pyridin-3-yl}-N-methyl-isobutyramide.

In certain particularly preferred compounds where X is $N(R^5)C(O)$— and $R^4$ is

$R^4$ is attached through the linker —$(CH_2)_nN(R^5)$—.

An example of such a compound is 2-(3,5-bis-trifluoromethyl-phenyl)-N-methyl-N-{6-[methyl-(2-morpholin-4-yl-ethyl)-amino]-4-o-tolyl-pyridin-3-yl}-isobutyramide.

In yet other such particularly preferred compounds where X is $N(R^5)C(O)$—, $R^4$ is —$N(R^5)_2$, —$N(R^5)(CH_2)_nOH$, —$N(R^5)S(O)_2$-lower alkyl, $N(R^5)S(O)_2$-phenyl, —$N=CH$—$N(R^5)_2$, —$N(R^5)C(O)R^5$. Such compounds include 2-(3,5-Bis-trifluoromethyl-phenyl)-N-(6-dimethylamino-4-o-tolyl-pyridin-3-yl)-N-methyl-isobutyramide, 2-(3,5-Bis-trifluoromethyl-phenyl)-N-[4-(2-chloro-phenyl)-6-dimethylamino-pyridin-3-yl]-isobutyramide, 2-(3,5-Bis-trifluoromethyl-phenyl)-N-{6-[(2-hydroxy-ethyl)-methyl-amino]-4-o-tolyl-pyridin-3-yl}-N-methyl-isobutyramide, N-(6-Benzylamino-4-o-tolyl-pyridin-3-yl)-2-(3,5-bis-trifluoromethyl-phenyl)-N-methyl-isobutyramide, N-(6-Amino-4-o-tolyl-pyridin-3-yl)-2-(3,5-bis-trifluoromethyl-phenyl)-N-methyl-isobutyramide, 2-(3,5-Bis-trifluoromethyl-phenyl)-N-[6-(dimethylamino-methyleneamino)-4-o-tolyl-pyridin-3-yl]-N-methyl-isobutyramide, 2-(3,5-Bis-trifluoromethyl-phenyl)-N-(6-methanesulfonylamino-4-o-tolyl-pyridin-3-yl)-N-methyl-isobutyramide, N-(6-Benzenesulfonylamino-4-o-tolyl-pyridin-3-yl)-2-(3,5-bis-trifluoromethyl-phenyl)-N-methyl-isobutyramide.

In other particularly preferred compounds (i.e. compounds where R is lower alkyl, lower alkoxy, halogen or trifluoromethyl, $R^1$ is halogen or hydrogen, and $R^2$ and $R^{2'}$ are independently hydrogen, halogen, trifluoromethyl, lower alkoxy or cyano), X is —$C(O)N(R^5)$—.

In some of these compounds, $R^4$ is hydrogen. Such compounds include N-(3,5-Bis-trifluoromethyl-benzyl)-N-methyl-4-o-tolyl-nicotinamide, N-(3,5-Bis-trifluoromethyl-benzyl)-N-methyl-4-(2-chloro-phenyl)-nicotinamide, N-(3,5-Bis-trifluoromethyl-benzyl)-N-methyl-4-(2-trifluoromethyl-phenyl)-nicotinamide, N-(3,5-Bis-trifluoromethyl-benzyl)-N-methyl-4-(2-fluoro-phenyl)-nicotinamide, N-(3,5-Bis-trifluoromethyl-benzyl)-N-methyl-4-(2-fluoro-phenyl)-nicotinamide, N-(3,5-Bis-trifluoromethyl-benzyl)-N-methyl-4-phenyl-nicotinamide, N-(3,5-Bis-trifluoromethyl-benzyl)-N-ethyl-4-o-tolyl-nicotinamide, N-(3,5-Bis-trifluoromethyl-benzyl)-N-cyclopropyl-4-o-tolyl-nicotinamide, N-[1-(3,5-Bis-trifluoromethyl-phenyl)-ethyl]-N-methyl-4-o-tolyl-nicotinamide, N-(3,5-di-Fluorobenzyl)-N-methyl-4-o-tolyl-nicotinamide, N-(3,5-di-Chlorobenzyl)-N-methyl-4-o-tolyl-nicotinamide.

In other particularly preferred compounds where X is —$C(O)N(R^5)$—$R^4$ is

preferably a five-membered or a six-membered tertiary amine ring, for example unsubstituted or substituted piperazinyl, morpholino, thiomorpholino, piperidinyl, or pyrrolidinyl. Examples of compounds where $R^4$ is unsubstituted or substituted piperazinyl are N-(3,5-Bis-trifluoromethyl-benzyl)-N-methyl-6-(4-methyl-piperazin-1-yl)-4-o-tolyl-nicotinamide, N-(3,5-Bis-trifluoromethyl-benzyl)-4-(2-chloro-phenyl)-N-methyl-6-(4-methyl-piperazin-1-yl)-nicotinamide, 4-{5-[(3,5-Bis-trifluoromethyl-benzyl)-methyl-carbamoyl]-4-o-tolyl-pyridin-2-yl}-piperazine-1-carboxylic acid, 4-{5-[(3,5-Bis-trifluoromethyl-benzyl)-methyl-carbamoyl]-4-o-tolyl-pyridin-2-yl}-piperazine-1-carboxylic acid, N-(3,5-Bis-trifluoromethyl-benzyl)-N-methyl-6-(4-propyl-piperazin-1-yl)-4-o-tolyl-nicotinamide, N-(3,5-Bis-trifluoromethyl-benzyl)-N-methyl-6-piperazin-1-yl-4-o-tolyl-nicotinamide, N-(3,5-Bis-trifluoromethyl-benzyl)-6-[4-(2-hydroxy-ethyl)-piperazin-1-yl]-N-methyl-4-o-tolyl-nicotinamide, N-(3,5-Bis-trifluoromethyl-benzyl)-6-(4-cyanomethyl-piperazin-1-yl)-N-methyl-4-o-tolyl-nicotinamide, N-(3,5-Bis-trifluoromethyl-benzyl)-6-{4-[2-(2-hydroxy-ethoxy)-ethyl]-piperazin-1-yl}-N-methyl-4-o-tolyl-nicotinamide, N-(3,5-Bis-trifluoromethyl-benzyl)-N-methyl-6-(4-[1,2,4]oxadiazol-3-ylmethyl-piperazin-1-yl)-4-o-tolyl-nicotinamide, N-(3,5-Bis-trifluoromethyl-benzyl)-N-methyl-6-(4-[1,2,4]oxadiazol-3-ylmethyl-piperazin-1-yl)-4-o-tolyl-nicotinamide, N-(3,5-Bis-trifluoromethyl-benzyl)-6-(4-formyl-piperazin-1-yl)-N-methyl-4-o-tolyl-nicotinamide, N-(3,5-Bis-trifluoromethyl-benzyl)-N-methyl-6-[4-(1H-tetrazol-5-ylmethyl)-piperazin-1-yl]-4-o-tolyl-nicotinamide.

Examples of compounds where $R^4$ is morpholino or substituted morpholino are N-(3,5-Bis-trifluoromethyl-benzyl)-N-methyl-6-morpholin-4-yl-4-o-tolylnicotinamide, N-(2-Methoxy-benzyl)-N-methyl-6-morpholin-4-yl-4-o-tolyl-nicotinamide, N-(5-Chloro-2-methoxy-benzyl)-N-methyl-6-morpholin-4-yl-4-o-tolyl-nicotinamide, N-(2-Chloro-5-methoxy-benzyl)-N-methyl-6-morpholin-4-yl-4-o-tolyl-nicotinamide, N-(2-Chloro-5-methoxy-benzyl)-N-methyl-6-morpholin-4-yl-4-o-tolyl-nicotinamide, N-[2-Methoxy-5-(5-trifluoromethyl-tetrazol-1-yl)-benzyl]-N-methyl-6-morpholin-4-yl-4-o-tolyl-nicotinamide.

Examples of compounds where $R^4$ is thiomorpholino or oxidized thiomorpholino are N-(3,5-Bis-trifluoromethyl-benzyl)-N-methyl-6-thiomorpholin-4-yl-4-o-tolyl-nicotinamide, N-(3,5-Bis-trifluoromethyl-benzyl)-N-methyl-6-(1-oxo-1$\lambda^4$-thiomorpholin-4-yl)-4-o-tolyl-nicotinamide, N-(3,5-Bis-trifluoromethyl-benzyl)-6-(1,1-dioxo-1$\lambda^6$-thiomorpholin-4-yl)-N-methyl-4-o-tolyl-nicotinamide.

Examples of compounds where $R^4$ is unsubstituted or substituted piperidinyl are 5'-[(3,5-Bis-trifluoromethyl-benzyl)-methyl-carbamoyl]-4'-o-tolyl-3,4,5,6-tetrahydro-2H-[1,2']bipyridinyl-4-carboxylic acid and 5'-[(3,5-Bis-trifluoromethyl-benzyl)-methyl-carbamoyl]-4'-o-tolyl-3,4,5,6-tetrahydro-2H-[1,2']bipyridinyl-4-carboxylic acid.

An example of a compound where $R^4$ is unsubstituted or substituted pyrrolidinyl is (RS)-6-[3-(acetyl-methyl-amino)-pyrrolidin-1-yl]-N-(3,5-bis-trifluoromethyl-benzyl)-N-methyl-4-o-tolyl-nicotinamide.

In certain particularly preferred compounds where X is —C(O)N($R^5$)— and $R^4$ is

$R^4$ is attached through the linker —(CH$_2$)$_n$N($R^5$)—.

An example of such a compound is N-(3,5-bis-trifluoromethyl-benzyl)-N-methyl-6-[methyl-(2-morpholin-4-yl-ethyl)-amino]-4-o-tolyl-nicotinamide.

In yet other such particularly preferred compounds where X is —C(O)N($R^5$)—, $R^4$ is —N($R^5$)$_2$, —N($R^5$)(CH$_2$)$_n$OH, —N($R^5$)S(O)$_2$-lower alkyl, N($R^5$)S(O)$_2$-phenyl, —N=CH—N($R^5$)$_2$, —N($R^5$)C(O)$R^5$.

In yet other particularly preferred compounds (i.e. compounds where R is lower alkyl, lower alkoxy, halogen or trifluoromethyl, $R^1$ is halogen or hydrogen, and $R^2$ and $R^{2'}$ are independently hydrogen, halogen, trifluoromethyl, lower alkoxy or cyano), X is —(CH$_2$)$_m$O—. Preferably $R^4$ is hydrogen.

An example of such a compound is 3-(3,5-bis-trifluoromethyl-benzyloxymethyl)-4-o-tolyl-pyridine.

In further particularly preferred compounds X is —(CH$_2$)$_m$N($R^5$)—. Preferably $R^4$ is hydrogen.

An example of such a compound is (3,5-bis-trifluoromethyl-benzyl)-methyl-(4-o-tolyl-pyridin-3-ylmethyl)-amine.

In another such compound, (3,5-bis-trifluoromethyl-benzyl)-[4-(2-chloro-phenyl)-6-(4-methyl-piperazin-1-yl)-pyridin-3-ylmethyl]-methyl-amine, $R^4$ is substituted piperazin.

In certain compounds of formula 1 where R is lower alkyl, lower alkoxy, halogen or trifluoromethyl and $R^1$ is halogen or hydrogen, $R^2$ and $R^{2'}$ together form —CH=CH—CH=CH—, unsubstituted or substituted by one or two substituents selected from lower alkyl or lower alkoxy. Preferably X is —C(O)N($R^5$)—. More preferably, R is lower alkyl, $R^1$ is hydrogen, $R^3$ and $R^{3'}$ are hydrogen, and $R^4$ is morpholino. Such compounds are N-Methyl-N-(2-methyl-naphthalen-1-ylmethyl)-6-morpholin-4-yl-4-o-tolyl-nicotinamide, N-Methyl-N-(2-methyl-naphthalen-1-ylmethyl)-6-morpholin-4-yl-4-o-tolyl-nicotinamide, N-(2-Methoxy-naphthalen-1-ylmethyl)-N-methyl-6-morpholin-4-yl-4-o-tolyl-nicotinamide, N-(2-Methoxy-naphthalen-1-ylmethyl)-N-methyl-6-morpholin-4-yl-4-o-tolyl-nicotinamide, N-(1,4-Dimethoxy-naphthalen-2-ylmethyl)-N-methyl-6-morpholin-4-yl-4-o-tolyl-nicotinamide.

In certain other compound of formula 1 where $R^2$ and $R^{2'}$ are independently hydrogen, halogen, trifluoromethyl, lower alkoxy or cyano, R and $R^1$ together form —CH=CH—CH=CH—. Preferably X is —C(O)N($R^5$)—. More preferably, $R^2$ and $R^{2'}$ are trifluoromethyl; $R^3$ and $R^{3'}$ are hydrogen, and $R^4$ is piperazinyl substituted with lower alkyl.

Such a compound is N-(3,5-bis-trifluoromethyl-benzyl)-N-methyl-6-(4-methyl-piperazin-1-yl)-4-naphthalen-1-yl-nicotinamide.

In certain preferred compounds, R is halogen or lower alkyl. It is also preferred that $R^1$ is hydrogen. Preferred substituents at $R^2$ and $R^{2'}$ are trifluoromethyl or halogen. Preferred substituents at $R^3$ and $R^{3'}$ are hydrogen or lower alkyl. It is also preferred that $R^5$ is lower alkyl. For X —N($R^5$)C(O)— is preferred. Preferably any combination of these substituents are found, for example R is halogen and $R^2$ and $R^{2'}$ are trifluoromethyl or halogen, and other combinations of the above substituents. In especially preferred compounds, all of the above are true, i.e. R is halogen or lower alkyl, $R^1$ is hydrogen, $R^2$ and $R^{2'}$ are trifluoromethyl or halogen, $R^3$ and $R^{3'}$ are hydrogen or lower alkyl, and X is —N($R^5$)C(O)— is preferred. In particular in such compounds, $R^5$ is preferably lower alkyl.

Examples of such compounds are 2-(3,5-bis-trifluoromethyl-phenyl)-N-methyl-N-[6-(4-methyl-piperazin-1-yl)-4-o-tolyl-pyridin-3-yl]-isobutyramide (where $R^4$ is 4-methyl-piperazin-1-yl), 2-(3,5-Bis-trifluoromethyl-phenyl)-N-[4-(2-chloro-phenyl)-pyridin-3-yl]-N-methyl-isobutyramide (where $R^4$ is hydrogen) and 2-(3,5-Bis-trifluoromethyl-phenyl)-N-methyl-N-(6-morpholin-4-yl-4-o-tolyl-pyridin-3-yl)-isobutyramide (where $R^4$ is unsubstituted morpholino).

An embodiment of this invention is 2-(3,5-bis-trifluoromethyl-phenyl)-N-methyl-N-(6-morpholin-4-yl-4-o-tolyl-pyridin-3-yl)-isobutyramide, the compound of formula I which has the formula:

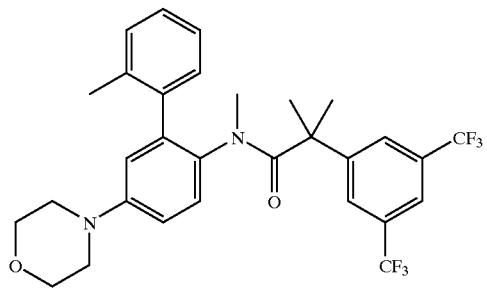

Ia and to pharmaceutically acceptable acid addition salts thereof.

This compound of formula Ia and its salts are characterized by valuable therapeutic properties as a highly selective antagonist of the Neurokinin 1 (NK-1, substance P) receptor. As described earlier, such activity is particularly useful for treating CNS disorders, such as depression, anxiety or emesis.

The present compound of formula Ia and its pharmaceutically acceptable salts can be prepared by methods known in the art, for example, by processes described below, which process comprises
a) reacting the compound of formula

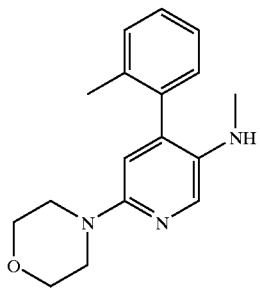

II with the compound of formula

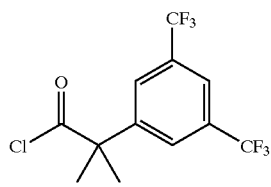

III to the compound of formula

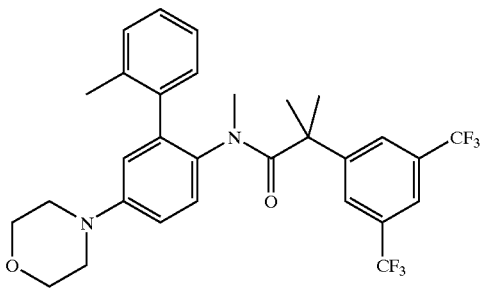

I and, if desired, converting the compound obtained into a pharmaceutically acceptable acid addition salt.

In accordance with process variant a) DIPEA (N-ethyldiisopropyl-amine) is added to a mixture of the compound of formula II and the compound of formula III in dichloromethane and the mixture is stirred at temperatures between 35–40° C. The desired compound of formula I is yielded after purification in good yields.

The salt formation is effected at room temperature in accordance with methods which are known per se and which are familiar to any person skilled in the art. Not only salts with inorganic acids, but also salts with organic acids are possible. Hydrochlorides, hydrobromides, sulphates, nitrates, citrates, acetates, maleates, succinates, methanesulphonates, p-toluenesulphonates and the like are examples of such salts.

The following schemes 1 and 2 and example 23 describe the processes for the preparation of the compound of formula Ia in more detail. The starting materials of formulae III, IV and VII are known compounds or may be prepared according to methods known in the art.

In the schemes the following abbreviations have been used:

| PivCl | pivaloyl chloride |
| THF | tetrahydrofuran |
| TMEDA | N,N,N',N'-tetramethylethylene diamine |
| DIPEA | N-ethyldiisopropyl-amine |

Scheme 1

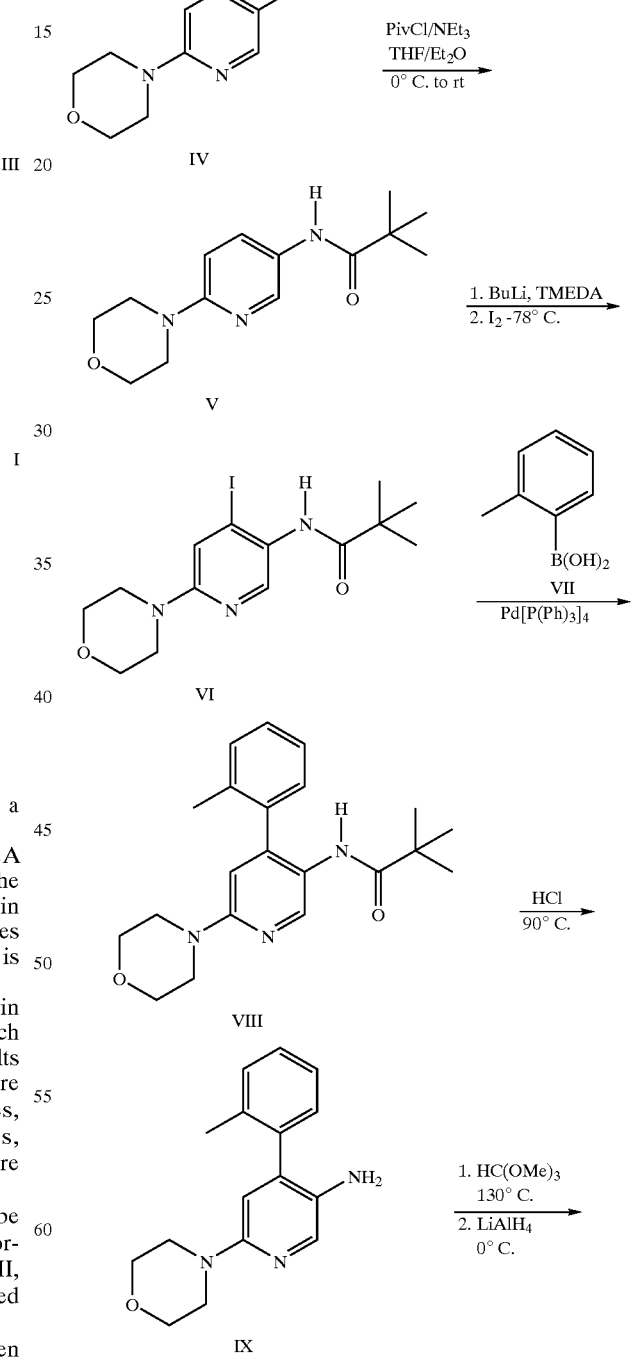

-continued

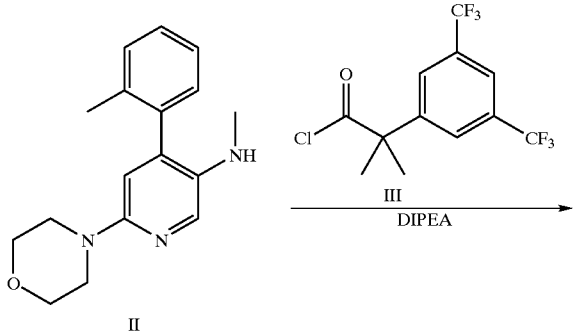

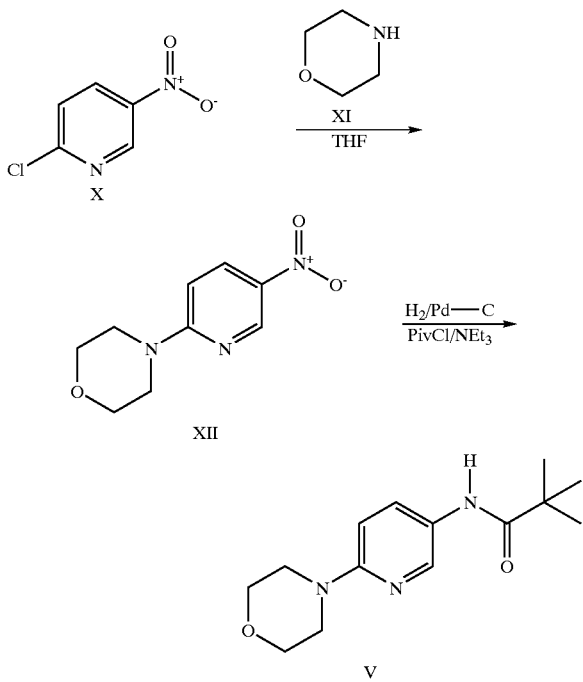

The affinity of compound of formula 1a for the NK$_1$ receptor was evaluated at human NK$_1$ receptors in CHO cells infected with the human NK$_1$ receptor (using the Semliki virus expression system) and radiolabelled with [$^3$H]substance P (final concentration 0.6 nM). Binding assays were performed in HEPES buffer (50 mM, pH 7.4) containing BSA (0.04%), leupeptin (8 μg/ml), MnCl$_2$ (3 mM) and phosphoramidon (2 μM). Binding assays consisted of 250 μl of membrane suspension (1.25×10$^5$ cells/assay tube), 0.125 μl of buffer of displacing agent and 125 μl of[$^3$H]substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 2×2 ml washes of HEPES buffer (50 mM, pH 7.4). The radioactivity retained on the filters was measured by scintillation counting. All assays were performed in triplicate in at least 2 separate experiments.

The compound of formula Ia is a potent and selective antagonist at recombinant human neurokinin, (NK$_1$) receptors expressed in CHO cells. It has an affinity (pKi) of 9.0 for the human NK$_1$ receptor over 2 orders of magnitude of selectivity for the NK$_1$ receptor compared to NK$_2$ and NK$_3$ receptors and compared to over 50 other binding sites that have been evaluated.

The following assays may be used for further screening for any compound of this invention to determine in vivo activity.

The activity in vitro of the compound of formula 1a was examined by studying its effect on substance P induced Ca$^{2+}$ influxes in CHO cells expressing the recombinant human NK$_1$ receptor. In these cells, substance P causes a concentration dependent influx of Ca$^{2+}$ which can be measured using FLIPR technology. Increasing concentrations of 2-(3, 5-bis-trifluoromethyl-phenyl)-N-methyl-N-(6-morpholin-4-yl-4-o-tolyl-pyridin-3-yl)-isobutyramide cause a rightward shift in the concentration effect curve of substance P. Expressing these data on a Schild plot allows the calculation of the antagonist affinity (pA$_2$) for this compound of 8.9 (slope of the Schild regression=1.1). These data indicate that 2-(3,5-bis-trifluoromethyl-phenyl)-N-methyl-N-(6-morpholin-4-yl-4-o-tolyl-pyridin-3-yl)-isobutyramide is a competitive antagonist at human recombinant NK$_1$ receptors.

In vivo the compound of formula Ia antagonises foot-tapping behaviour induced in gerbils with intracerebroventricular (i.c.v.) injections of an NK$_1$ receptor agonist. The dose for this compound calculated to inhibit 50% of the foot-tapping behaviour following oral administration was 0.2 mg/kg. The plasma levels required to completely antagonise this behaviour have also been measured and it was found that a total plasma concentration of 10 ng/ml is required to completely block the foot-tapping behavoiur. This antagonism persisted for a number of hours and had a functional half life of 8 hours in this model.

The compound of formula 1a, 2-(3,5-Bis-trifluoromethyl-phenyl)-N-methyl-N-(6-morpholin-4-yl-4-o-tolyl-pyridin-3-yl)-isobutyramide, was also tested as an antiemetic agent in ferrets. Emesis was induced in ferrets by various emetogens (apomorphine, morphine, ipecacuanha, cisplatin and CuSO$_4$. Pretreatment with this compound (0.3 mg/kg, p.o.) 2 hours before the emetigen, completely blocked the emesis induced by all emetogens. A full dose-response curve was constructed against apomorphine-induced emesis and an ED$_{50}$ dose of 0.1 mg/kg, p.o. was calculated.

In a model of motion sickness in the *suncus murinus*, the compound was found to have an ED$_{50}$ of 0.2 mg/kg, p.o.

Therefore, in conclusion, 2-(3,5-bis-trifluoromethyl-phenyl)-N-methyl-N-(6-morpholin-4-yl-4-o-tolyl-pyridin-3-yl)-isobutyramide is a potent antagonist of NK$_1$ induced behaviours in gerbils and blocks emesis in ferrets and *suncus murinus* with similar potency.

The pharmacokinetic parameters have been evaluated in both rats and dogs. In rats, the compound has a terminal half-life of 23 hours, a clearance of 4 ml/min/kg, a volume of distribution of 8 l/kg and an oral bioavailability of 50%. In dogs the molecule had a half-life of 40 hours, a clearance of 16 ml/min/kg, a volume of distribution of 22 l/kg and an oral bioavailability of 30–40%.

Another embodiment of this invention is a compound of formula I (2-(3,5-bis-trifluoromethyl-phenyl)-N-methyl-N-[6-(4-methyl-piperazin-1-yl)-4-o-tolyl-pyridin-3-yl]-isobutyramide) which has the formula Ib

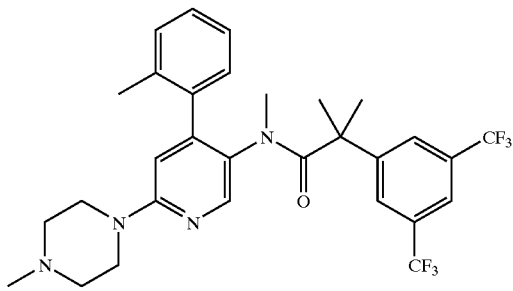

and to pharmaceutically acceptable acid addition salts thereof.

The compound of formula Ib and its salts is also characterized by valuable therapeutic properties as a highly selective antagonist of the Neurokinin 1 (NK-1, substance P).

The present compound of formula Ib and its pharmaceutically acceptable salts can be prepared by methods known in the art, for example, by processes described below, which process comprises a) reacting the compound of formula

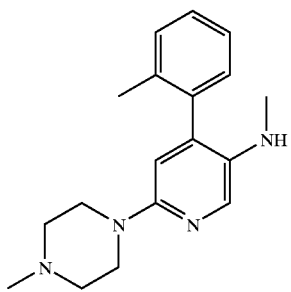

with the compound of formula

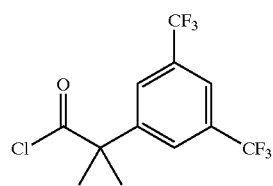

to the compound of formula

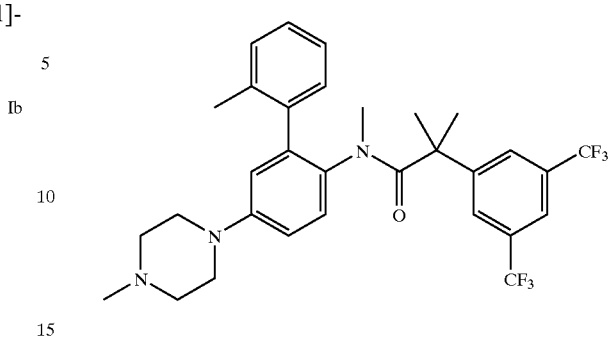

and,
if desired, converting the compound obtained into a pharmaceutically acceptable acid addition salt.

In accordance with process variant a) DIPEA (N-ethyldiisopropyl-amine) is added to a mixture of the compound of formula II and the compound of formula III in dichloromethane and the mixture is stirred at temperatures between 35–40° C. The desired compound of formula I is yielded after purification in good yields.

The salt formation is effected at room temperature in accordance with methods which are known per se and which are familiar to any person skilled in the art. Not only salts with inorganic acids, but also salts with organic acids are possible. Hydrochlorides, hydrobromides, sulphates, nitrates, citrates, acetates, maleates, succinates, methanesulphonates, p-toluenesulphonates and the like are examples of such salts.

The following schemes 1 and 2 and example 14 describe the processes for the preparation of the compound of formula Ib in more detail. The starting materials of formulae III, IV and VII are known compounds or may be prepared according to methods known in the art.

In the schemes the following abbreviations have been used:

| | |
|---|---|
| PivCl | pivaloyl chloride |
| THF | tetrahydrofuran |
| TMEDA | N,N,N',N'-tetramethylethylene diamine |
| DIPEA | N-ethyldiisopropyl-amine |

Scheme 1

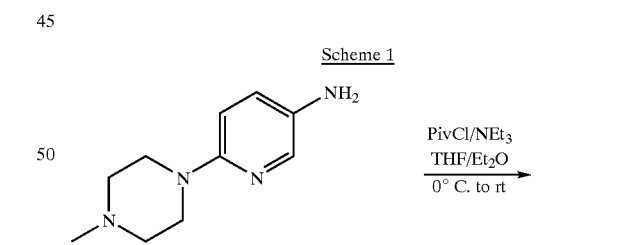

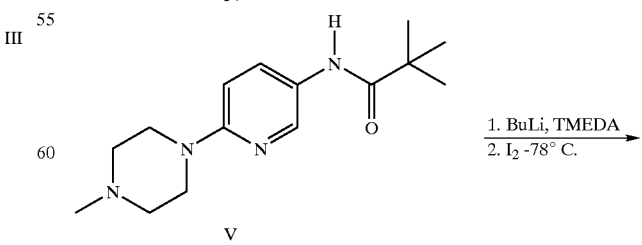

Scheme 2

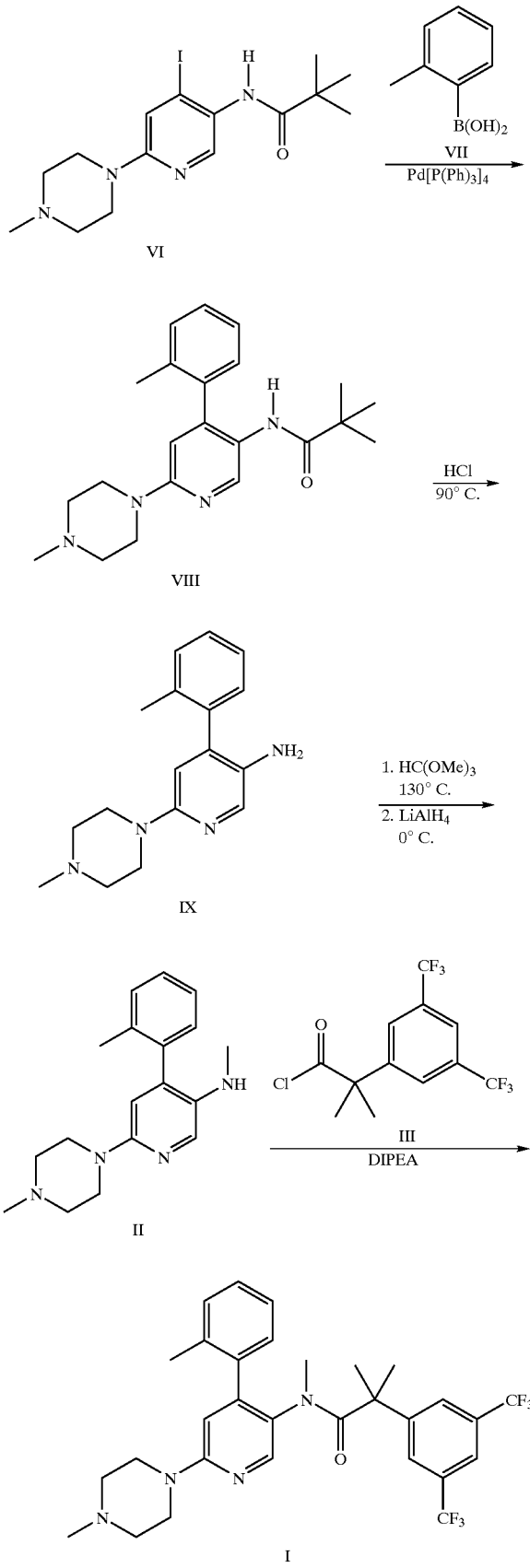
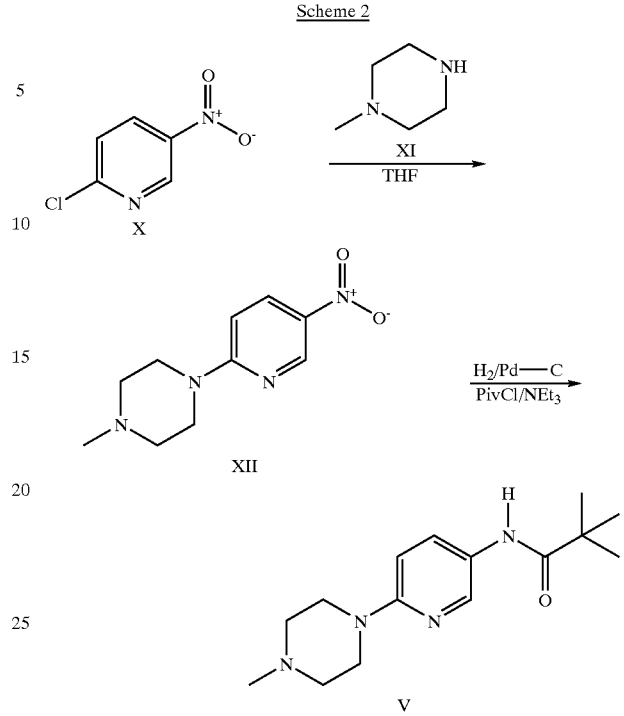

The affinity of the compound of formula Ib for the $NK_1$ receptor was evaluated at human $NK_1$ receptors in CHO cells infected with the human $NK_1$ receptor (using the Semliki virus expression system) and radiolabelled with [$^3$H]substance P (final concentration 0.6 nM). Binding assays were performed in HEPES buffer (50 mM, pH 7.4) containing BSA (0.04%) leupeptin (8 μg/ml), $MnCl_2$ (3 mM) and phosphoramidon (2 μM). Binding assays consisted of 250 μl of membrane suspension (1.25×10$^5$ cells/assay tube), 0.125 μl of buffer of displacing agent and 125 μl of [$^3$H] substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 2×2 ml washes of HEPES buffer (50 mM, pH 7.4). The radioactivity retained on the filters was measured by scintillation counting. All assays were performed in triplicate in at least 2 separate experiments.

The compound of formula Ib is a potent and selective antagonist at recombinant human neurokinin, ($NK_1$) receptors expressed in CHO cells. It has an affinity (pKi) of 9.0 for the human $NK_1$ receptor and over 2 orders of magnitude of selectivity for the $NK_1$ receptor compared to $NK_2$ and $NK_3$ receptors and compared to over 50 other binding sites that have been evaluated.

The following assays may be used for further screening for any compound of this invention to determine in vivo activity.

The activity of 2-(3,5-bis-trifluoromethyl-phenyl)-N-methyl-N-[6-(4-methyl-piperazin-1-yl)-4-o-tolyl-pyridin-3-yl]-isobutyramide in vitro was examined by studying its effect on substance P induced $Ca^{2+}$ influxes in CHO cells expressing the recombinant human $NK_1$ receptor. In these cells, substance P causes a concentration dependent influx of $Ca^{2+}$ which can be measured using FLIPR technology. The compound inhibited this effect in a concentration dependent manner. These data indicate that 2-(3,5-bis-trifluoromethyl-phenyl)-N-methyl-N-[6-(4-methyl-piperazin-1-yl)-4-o-tolyl-pyridin-3-yl]-isobutyramide is a competitive antagonist at human recombinant $NK_1$ receptors.

In vivo 2-(3,5-bis-trifluoromethyl-phenyl)-N-methyl-N-[6-(4-methyl-piperazin-1-yl)-4-o-tolyl-pyridin-3-yl]-isobutyramide antagonises foot-tapping behaviour induced in Gerbils with intracerebroventricular (i.c.v.) injections of an $NK_1$ receptor agonist. The dose of this compound calculated to inhibit 50% of the foot-tapping behaviour following oral administration was 0.5 mg/kg. The plasma levels required to completely antagonise this behaviour have also been measured and it was found that a total plasma concentration of 30 ng/ml is required to completely block the foot-tapping behavoiur. This antagonism persisted for a number of hours and had a functional half life of 30 hours in this model.

2-(3,5-bis-trifluoromethyl-phenyl)-N-methyl-N-[6-(4-methyl-piperazin-1-yl)-4-o-tolyl-pyridin-3-yl]-isobutyramide was also tested as an antiemetic agent in Ferrets. Emesis was induced in Ferrets by various emetogens (apomorphine, morphine, ipecacuanha, cisplatin and $CuSO_4$. Pretreatment of this compound (0.3 mg/kg, p.o.) 2 hours before the emetigen, completely blocked the emesis induced by all emetogens. A full dose-response curve was constructed against apomorphine-induced emesis and an $ED_{50}$ dose of 0.1 mg/kg, p.o. was calculated.

In a model of motion sickness in the suncus murinus, 2-(3,5-bis-trifluoromethyl-phenyl)-N-methyl-N-[6-(4-methyl-piperazin-1-yl)-4-o-tolyl-pyridin-3-yl]-isobutyramide was found to have an $ED_{50}$ of 0.2 mg/kg, p.o.

Therefore, in conclusion, 2-(3,5-bis-trifluoromethyl-phenyl)-N-methyl-N-[6-(4-methyl-piperazin-1-yl)-4-o-tolyl-pyridin-3-yl]-isobutyramide is a potent antagonist of $NK_1$ induced behaviours in Gerbil and blocks emesis in Ferrets and suncus murinus with similar potency.

The pharmacokinetic parameters have been evaluated in both rats and dogs. In rats, the compound has a terminal half-life of 24 hours, a clearance of 3.7 mL/min/kg, a volume of distribution of 5.7 l/kg and an oral bioavailability of 45%. In dogs the molecule had a half-life of 18 hours, a clearance of 9.2 ml/min/kg, a volume of distribution of 15 l/kg and an oral bioavailability of 75%.

Yet another embodiment of this invention is 2-(3,5-Bis-trifluoromethyl-phenyl)-N-[4-(2-chloro-phenyl)-pyridin-3-yl]-N-methyl-isobutyramide, the compound of formula Ic

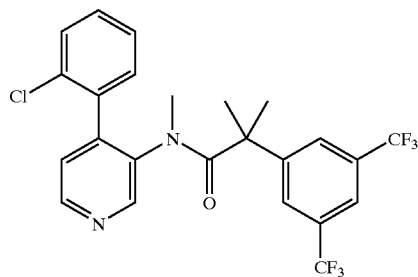

and to pharmaceutically acceptable acid addition salts thereof.

The compound of formula Ic and its salts are characterized by valuable therapeutic properties. It has been found that the compound of the present invention is a highly selective antagonist of the Neurokinin 1 (NK-1, substance P) receptor.

The present compound of formula Ic and pharmaceutically acceptable salts can be prepared by methods known in the art, for example, by processes described below, which process comprises a) reacting the compound of formula

II

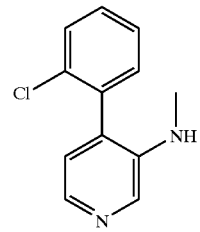

with the compound of formula

III

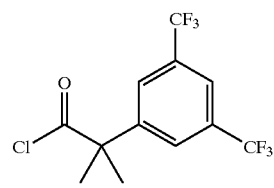

to the compound of formula

I

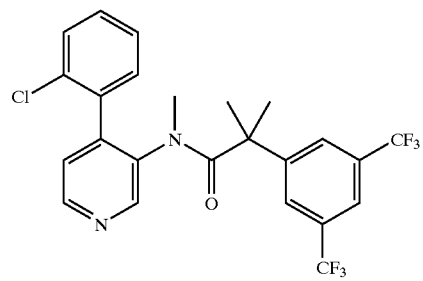

and, if desired, converting the compound obtained into a pharmaceutically acceptable acid addition salt.

In accordance with process variant a) DIPEA (N-ethyldiisopropyl-amine) is added to a mixture of the compound of formula II and the compound of formula III in dichloromethane and the mixture is stirred at temperatures between 35–40° C. The desired compound of formula Ic is yielded after purification in good yields.

The salt formation is effected at room temperature in accordance with methods which are known per se and which are familiar to any person skilled in the art. Not only salts with inorganic acids, but also salts with organic acids are possible. Hydrochlorides, hydrobromides, sulphates, nitrates, citrates, acetates, maleates, succinates, methanesulphonates, p-toluenesulphonates and the like are examples of such salts.

The following schemes 1 and 2 and example 17 describe the processes for the preparation of the compound of formula Ic in more detail. The starting materials of formulae III, IV and VII are known compounds or may be prepared according to methods known in the art.

In the schemes the following abbreviations have been used:

| | |
|---|---|
| PivCl | pivaloyl chloride |
| THF | tetrahydrofuran |
| TMEDA | N,N,N',N'-tetramethylethylene diamine |
| DIPEA | N-ethyldiisopropyl-amine |

Scheme 1

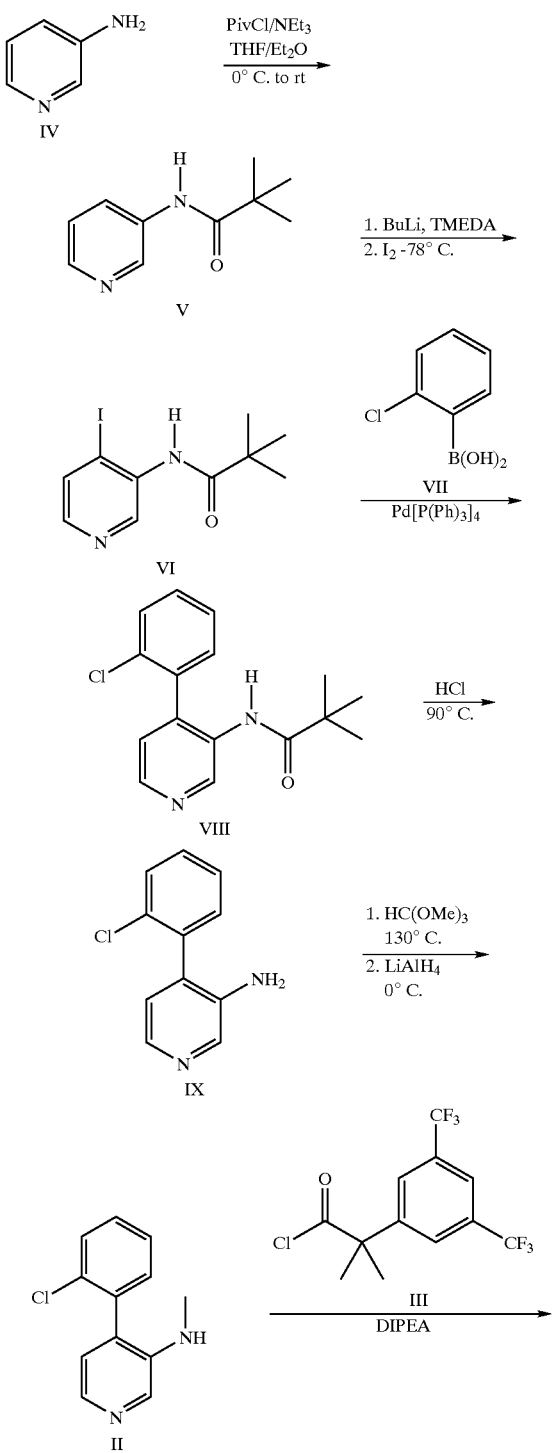

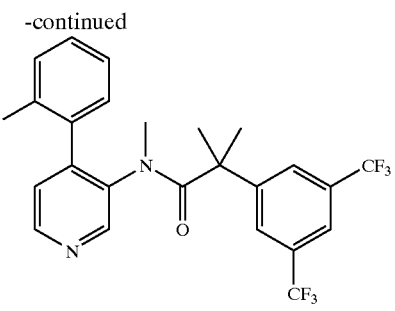

Scheme 2

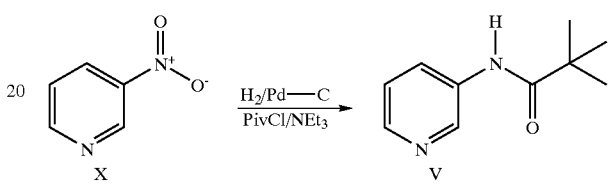

The affinity of the compound of formula Ic for the $NK_1$ receptor was evaluated at human $NK_1$ receptors in CHO cells infected with the human $NK_1$ receptor (using the Semliki virus expression system) and radiolabelled with [$^3$H]substance P (final concentration 0.6 nM). Binding assays were performed in HEPES buffer (50 mM, pH 7.4) containing BSA (0.04%) leupeptin (8 μg/ml), $MnCl_2$ (3 mM) and phosphoramidon (2 μM). Binding assays consisted of 250 μl of membrane suspension ($1.25 \times 10^5$ cells/assay tube), 0.125 μl of buffer of displacing agent and 125 μl of [$^3$H] substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 2×2 ml washes of HEPES buffer (50 mM, pH 7.4). The radioactivity retained on the filters was measured by scintillation counting. All assays were performed in triplicate in at least 2 separate experiments.

2-(3,5-Bis-trifluoromethyl-phenyl)-N-[4-(2-chlorophenyl)-pyridin-3-yl]-N-methyl-isobutyramide is a potent and selective antagonist at recombinant human neurokinin, ($NK_1$) receptors expressed in CHO cells. It has an affinity (pKi) of 8.6 for the human $NK_1$ receptor over 2 orders of magnitude of selectivity for the $NK_1$ receptor compared to $NK_2$ and $NK_3$ receptors and compared to over 50 other binding sites that have been evaluated. The activity of the compound of formula Ic in vitro was examined by studying its effect on substance P induced $Ca^{2+}$ influxes in CHO cells expressing the recombinant human $NK_1$ receptor. In these cells, substance P causes a concentration dependent influx of $Ca^{2+}$ which can be measured using FLIPR technology. 2-(3,5-Bis-trifluoromethyl-phenyl)-N-[4-(2-chloro-phenyl)-pyridin-3-yl]-N-methyl-isobutyramide inhibited this effect in a concentration dependent manner. These data indicate that this compound is a competitive antagonist at human recombinant $NK_1$ receptors.

In vivo the compound of formula Ic antagonises foot-tapping behaviour induced in Gerbils with intracerebroventricular (i.c.v.) injections of an $NK_1$ receptor agonist. The dose of this compound calculated to inhibit 50% of the foot-tapping behaviour following oral administration was 1.5 mg/kg. The plasma levels required to completely antagonise this behaviour have also been measured and it was found that a total plasma concentration of 100 ng/ml are required to completely block the foot-tapping behavior.

Therefore, in conclusion, 2-(3,5-bis-trifluoromethyl-phenyl)-N-[4-(2-chloro-phenyl)-pyridin-3-yl]-N-methyl-isobutyramide is a potent antagonist of $NK_1$ induced behaviours in Gerbils.

The pharmacokinetic parameters have been evaluated in both rats and dogs. In rats, the compound of formula Ic has a terminal half-life of 11 hours, a clearance of 45 mL/min/kg, a volume of distribution of 2.6 l/kg and an oral bioavailability of ~30%. In dogs the molecule had a half-life of 3.5 hours, a clearance of 30 ml/min/kg, a volume of distribution of 4.5 l/kg and an oral bioavailability of 16%.

Exemplary preferred are compounds, in which X is —C(O)N($R^5$)—, wherein $R^5$ is methyl, ethyl or cyclopropyl, for example the following compounds: N-(3,5-Bis-trifluoromethyl-benzyl)-N-methyl-4-o-tolyl-nicotinamide, N-(3,5-Bis-trifluoromethyl-benzyl)-N-methyl-4-(2-chloro-phenyl)-nicotinamide, N-(3,5-Bis-trifluoromethyl-benzyl)-N-methyl-4-(2-trifluoromethyl-phenyl)-nicotinamide, N-(3,5-Bis-trifluoromethyl-benzyl)-N-methyl-4-(2-fluoro-phenyl)-nicotinamide, N-(3,5-Bis-trifluoromethyl-benzyl)-N-methyl-4-(2-methoxy-phenyl)-nicotinamide, N-(3,5-Bis-trifluoromethyl-benzyl)-N-methyl-4-phenyl-nicotinamide, N-(3,5-Bis-trifluoromethyl-benzyl)-N-ethyl-4-o-tolyl-nicotinamide, N-(3,5-Bis-trifluoromethyl-benzyl)-N-cyclopropyl-4-o-tolyl-nicotinamide, N-[1-(3,5-Bis-trifluoromethyl-phenyl)-ethyl]-N-methyl-4-o-tolyl-nicotinamide, N-(3,5-Di-fluorobenzyl)-N-methyl-4-o-tolyl-nicotinamide, N-(3,5-Di-chlorobenzyl)-N-methyl-4-o-tolyl-nicotinamide, N-(3,5-Bis-trifluoromethyl-benzyl)-N-methyl-6-(4-methyl-piperazin-1-yl)-4-o-tolyl-nicotinamide, 2'-Methyl-5-(4-methyl-piperazin-1-yl)-biphenyl-2-carboxylic acid-(3,5-bis-trifluoro-methyl-benzyl)-methyl-amide, N-(3,5-Bis-trifluoromethyl-benzyl)-N-methyl-6-(4-methyl-piperazin-1-yl)-4-naphthalen-1-yl-nicotinamide, (4-{5-[(3,5-Bis-trifluoromethyl-benzyl)-methyl-carbamoyl]-4-o-tolyl-pyridin-2-yl}-piperazin-1-yl)-acetic acid ethyl ester, 5'-[(3,5-Bis-trifluoromethyl-benzyl)-methyl-carbamoyl]-4'-o-tolyl-3,4,5,6-tetrahydro-2H-[1,2'] bipyridinyl-4-carboxylic acid ethyl ester, N-(3,5-Bis-trifluoromethyl-benzyl)-N-methyl-6-(4-propyl-piperazin-1-yl)-4-o-tolyl-nicotinamide, (RS)-6-[3-(Acetyl-methyl-amino)-pyrrolidin-1-yl]-N-(3,5-bis-trifluoromethyl-benzyl)-N-methyl-4-o-tolyl-nicotinamide, N-(3,5-Bis-trifluoromethyl-benzyl)-N-methyl-6-[methyl-(2-morpholin-4-yl-ethyl)-amino]-4-o-tolyl-nicotinamide, N-(3,5-Bis-trifluoromethyl-benzyl)-N-methyl-6-morpholin-4-yl-4-o-tolyl-nicotinamide, N-(3,5-Bis-trifluoromethyl-benzyl)-N-methyl-6-thiomorpholin-4-yl-4-o-tolyl-nicotinamide, N-(3,5-Bis-trifluoromethyl-benzyl)-N-methyl-6-(1-oxo-1l-4-thiomorpholin-4-yl)-4-o-tolyl-nicotinamide, N-(3,5-Bis-trifluoromethyl-benzyl)-6-(1,1-dioxo-1l-6-thiomorpholin-4-yl)-N-methyl-4-o-tolyl-nicotinamide, N-(3,5-Bis-trifluoromethyl-benzyl)-N-methyl-6-piperazin-1-yl-4-o-tolyl-nicotinamide, N-(3,5-Bis-trifluoromethyl-benzyl)-6-[4-(2-hydroxy-ethyl)-piperazin-1-yl]-N-methyl-4-o-tolyl-nicotinamide, N-(3,5-Bis-trifluoromethyl-benzyl)-6-(4-cyanomethyl-piperazin-1-yl)-N-methyl-4-o-tolyl-nicotinamide, N-(3,5-Bis-trifluoromethyl-benzyl)-6-{4-[2-(2-hydroxy-ethoxy)-ethyl]-piperazin-1-yl}-N-methyl-4-o-tolyl-nicotinamide, N-(3,5-Bis-trifluoromethyl-benzyl)-N-methyl-6-(4-[1,2,4]oxadiazol-3-ylmethyl-piperazin-1-yl)-4-o-tolyl-nicotinamide, N-(3,5-Bis-trifluoromethyl-benzyl)-N-methyl-6-[4-(5-oxo-4,5-dihydro-1H-[1,2,4]triazol-3-ylmethyl)-piperazin-1-yl]-4-o-tolyl-nicotinamide, N-(3,5-Bis-trifluoromethyl-benzyl)-6-(4-formyl-piperazin-1-yl)-N-methyl-4-o-tolyl-nicotinamide and N-Methyl-N-(2-methyl-naphthalen-1-ylmethyl)-6-morpholin-4-yl-4-o-tolyl-nicotinamide.

Further preferred are compounds, in which X is —N($R^5$)—CO—, wherein $R^5$ is hydrogen or methyl.

Examples of such compounds are: 2-(3,5-Bis-trifluoromethyl-phenyl)-N-methyl-N-[6-(4-methyl-piperazin-1-yl)-4-o-tolyl-pyridin-3-yl]-isobutyramide, 2-(3,5-Bis-trifluoromethyl-phenyl)-N-[4-(2-chloro-phenyl)-6-(4-methyl-piperazin-1-yl)-pyridin-3-yl]-N-methyl-isobutyramide, 2-(3,5-Bis-trifluoromethyl-phenyl)-N-[4-(4-fluoro-2-methyl-phenyl)-6-(4-methyl-piperazin-1-yl)-pyridin-3-yl]-N-methyl-isobutyramide, 2-(3,5-Bis-trifluoromethyl-phenyl)-N-[4-(2-chloro-phenyl)-pyridin-3-yl]-N-methyl-isobutyramide, 2-(3,5-Bis-trifluoromethyl-phenyl-N-methyl-N-(4-o-tolyl-pyridin-3-yl)-isobutyramide, 2-(3,5-Bis-trifluoromethyl-phenyl)-N-(4-o-tolyl-pyridin-3-yl)-isobutyramide, 2-(3,5-Bis-trifluoromethyl-phenyl)-N-methyl-N-(4-o-tolyl-pyridin-3-yl)-acetamide, 2-(3,5-Bis-trifluoromethyl-phenyl)-N-methyl-N-(4-o-tolyl-pyridin-3-yl)-propionamide, 2-(3,5-Bis-trifluoromethyl-phenyl)-N-methyl-N-(6-morpholin-4-yl-4-o-tolyl-pyridin-3-yl)-isobutyramide, 2-(3,5-Bis-trifluoromethyl-phenyl)-N-[4-(2-chloro-phenyl)-6-morpholin-4-yl-pyridin-3-yl]-N-methyl-isobutyramide, 2-(3,5-Bis-trifluoromethyl-phenyl)-N-methyl-N-{6-[methyl-(2-morpholin-4-yl-ethyl)-amino]-4-o-tolyl-pyridin-3-yl}-isobutyramide, 2-(3,5-Bis-trifluoromethyl-phenyl)-N-methyl-N-[6-(4-pyrimidin-2-yl-piperazin-1-yl)-4-o-tolyl-pyridin-3-yl]-isobutyramide, 2-(3,5-Bis-trifluoromethyl-phenyl)-N-(6-morpholin-4-yl-4-o-tolyl-pyridin-3-yl)-isobutyramide, 2-(3,5-Bis-trifluoromethyl-phenyl)-N-[4-(2-chloro-phenyl)-6-dimethylamino-pyridin-3-yl]-isobutyramide, 2-(3,5-Bis-trifluoromethyl-phenyl)-N-methyl-N-(6-piperazin-1-yl-4-o-tolyl-pyridin-3-yl)-isobutyramide, 2-(3,5-Bis-trifluoromethyl-phenyl)-N-(4-hydroxy-4'-o-tolyl-3,4,5,6-tetrahydro-2H-[1,2']bipyridinyl-5'-yl)-N-methyl-isobutyramide, 2-(3,5-Bis-trifluoromethyl-phenyl)-N-{6-[(2-hydroxy-ethyl)-methyl-amino]-4-o-tolyl-pyridin-3-yl}-N-methyl-isobutyramide, (R)-2-(3,5-Bis-trifluoromethyl-phenyl)-N-[6-(3-hydroxy-pyrrolidin-1-yl)-4-o-tolyl-pyridin-3-yl]-N-methyl-isobutyramide, 2-(3,5-Bis-trifluoromethyl-phenyl)-N-methyl-N-(6-morpholin-4-yl-4-o-tolyl-pyridin 3-yl)-acetamide and [2-(3,5-Bis-trifluoromethyl-phenyl)-2-methyl-propyl]-[4-(4-fluoro-2-methyl-phenyl)-6-(4-methyl-piperazin-1-yl)-pyridin-3-yl]-methyl-amine.

The present compounds of this invention and their pharmaceutically acceptable salts can be prepared by methods known in the art, for example, by processes described below, which process comprises a) reacting a compound of formula

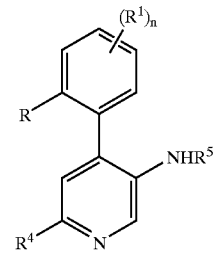

II with a compound of formula.

The present compounds of this invention and their pharmaceutically acceptable salts can be prepared by methods known in the art, for example, by processes described below, which process comprises a) reacting a compound of formula

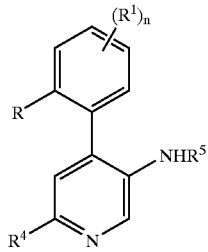

II with a compound of formula

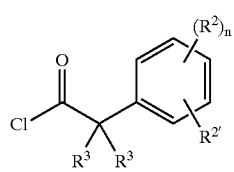

III to a compound of formula

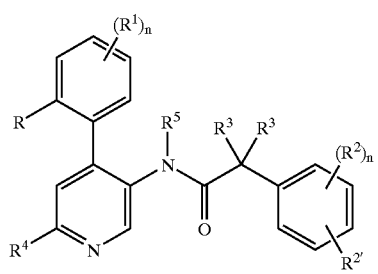

I-1 wherein $R^1$–$R^5$, R and n have the significances given above, or b) reacting a compound of formula

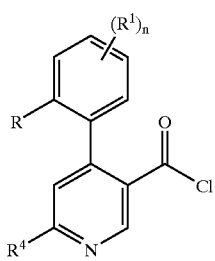

IV with a compound of formula

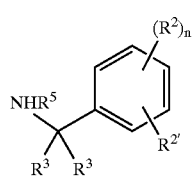

V to give a compound of formula

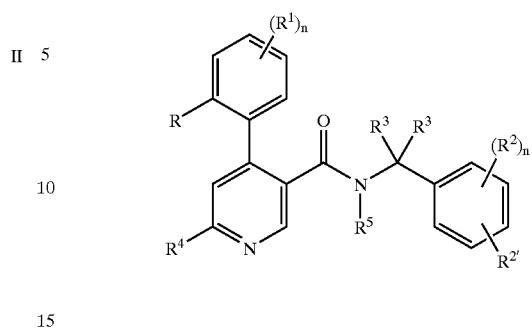

I-2 wherein $R^1$–$R^5$, R and n have the significances given above, or c) reducing a compound of formula

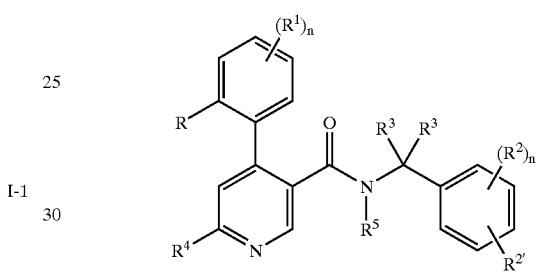

I-2 to a compound of formula

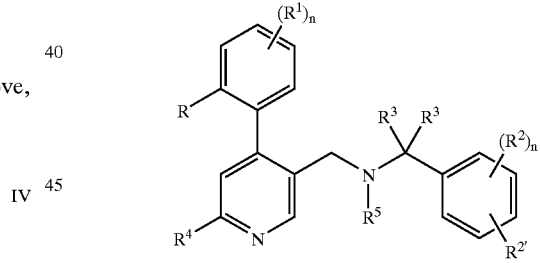

I-4 wherein the definition of substituents is given above, or d) reacting a compound of formula

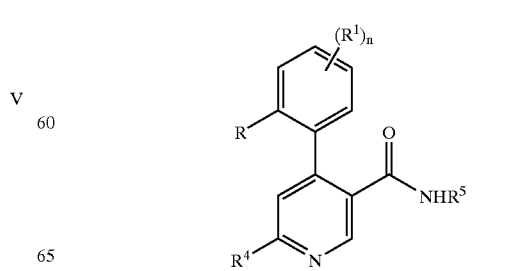

VI with a compound of formula

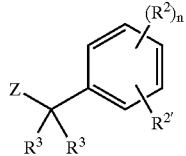

to a compound of formula

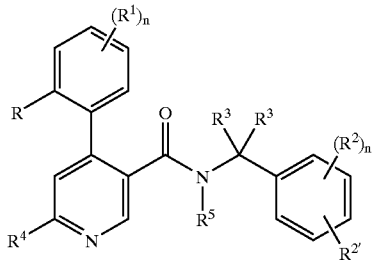

wherein Z is Cl, Br, I or —OS(O)$_2$C$_6$H$_4$CH$_3$ and the other definitions of substituents are given above, or e) reacting a compound of formula

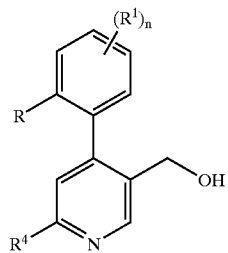

with a compound of formula

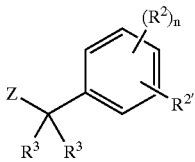

to a compound of formula

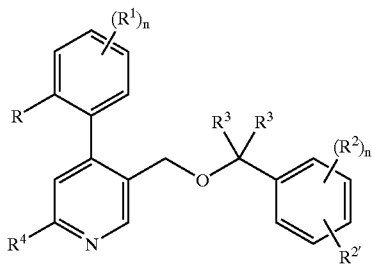

wherein Z is Cl, Br, I or OS(O)$_2$C$_6$H$_4$CH$_3$ and the definition of the other substituents is given above, or f) reducing a compound of formula

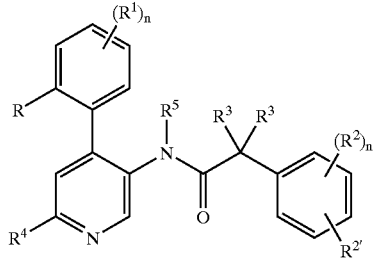

to a compound of formula

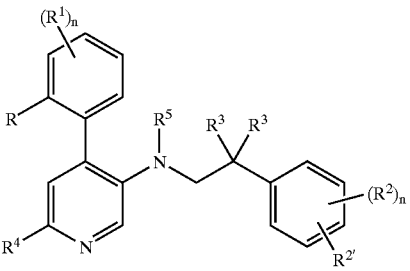

wherein the definition of substituents is given above, or h) modifying one or more substituents R$^1$–R$^6$ or R within the definitions given above, and if desired, converting the compound obtained into a pharmaceutically acceptable acid addition salt.

In accordance with process variant a) DIPEA (N-ethyldiisopropyl-amine) is added to a mixture of a compound of formula II, for example methyl-[6-(4-methyl-piperazin-1-yl)-4-o-tolyl-pyridin-3-yl]amine, and a compound of formula III, for example 2-(3,5-bis-trifluoromethyl-phenyl)-2-methyl-propionyl chloride in dichloromethane and the mixture is stirred at temperatures between 35–40° C. The desired compound of formula I-1 is isolated after purification in good yields.

Process variant b) describes the reaction of a compound of formula IV with a compound of formula V to a compound of formula I-2. The reaction is carried out in conventional manner, for example in a solvent, such as a mixture of toluene and triethylamine. The mixture is refluxed for about 1 hour.

In accordance with process variant c) a compound of formula I-2 is reduced to a compound of formula I-4. This reaction is carried out with a reducing agent, such as LiAlH$_4$ or BH$_3$.THF, in conventional manner.

Process variant d) describes the reaction of a compound of formula VI with a compound of formula VII to a compound of formula I-2. This reaction is carried out by deprotonation of a compound of formula VI with KHMDS (potassium hexamethyldisilazide) and subsequent addition of a compound of formula VII. A suitable solvent is tetrahydrofuran. The reaction is carried out at room temperature.

In accordance with process variant e) a compound of formula I-5 is prepared. This reaction is carried out by deprotonation of a compound of formula VIII with NaH and subsequent addition of a compound of formula VII. This reaction is carried out in conventional manner.

A further method for the preparation of a compound of this invention is described in process variant f). A compound of formula I-1 is reduced to a compound of formula I-3 in conventional manner, for example with LiAlH$_4$ or BH$_3$.THF.

The salt formation is effected at room temperature in accordance with methods which are known per se and which are familiar to any person skilled in the art. Not only salts with inorganic acids, but also salts with organic acids come into consideration. Hydrochlorides, hydrobromides, sulphates, nitrates, citrates, acetates, maleates, succinates, methanesulphonates, p-toluenesulphonates and the like are examples of such salts.

The following schemes 1–8 describe the processes for preparation of compounds of formula I in more detail. The starting materials of formulae V, IX, XII, XV, XVI, XXII, XXV, XXVIII, IXXX and XXX are known compounds and maybe prepared according to methods known in the art.

In the schemes the following abbreviations have been used:

| | |
|---|---|
| PivCl | pivaloyl chloride |
| THF | tetrahydrofuran |
| TMEDA | N,N,N',N'-tetramethylethylene diamine |
| DIPEA | N-ethyldiisopropyl-amine |
| KHMDS | potassium hexamethyldisilazide |

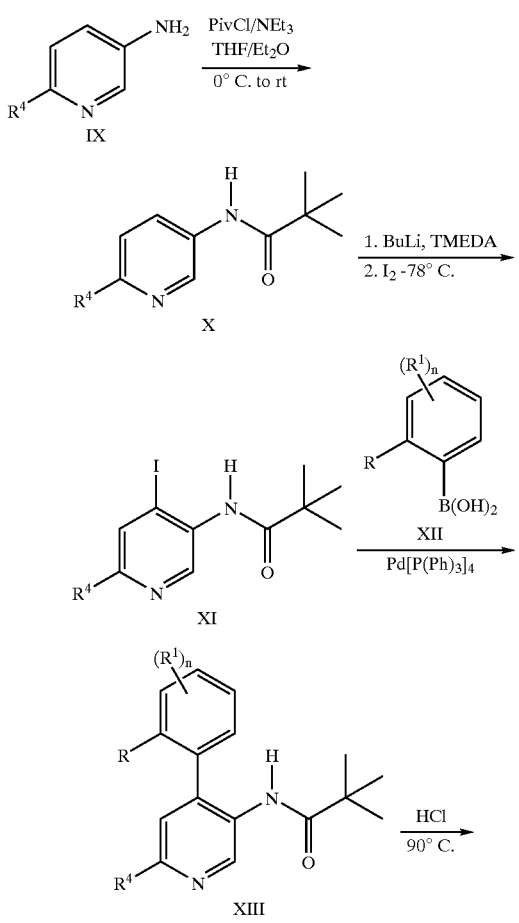

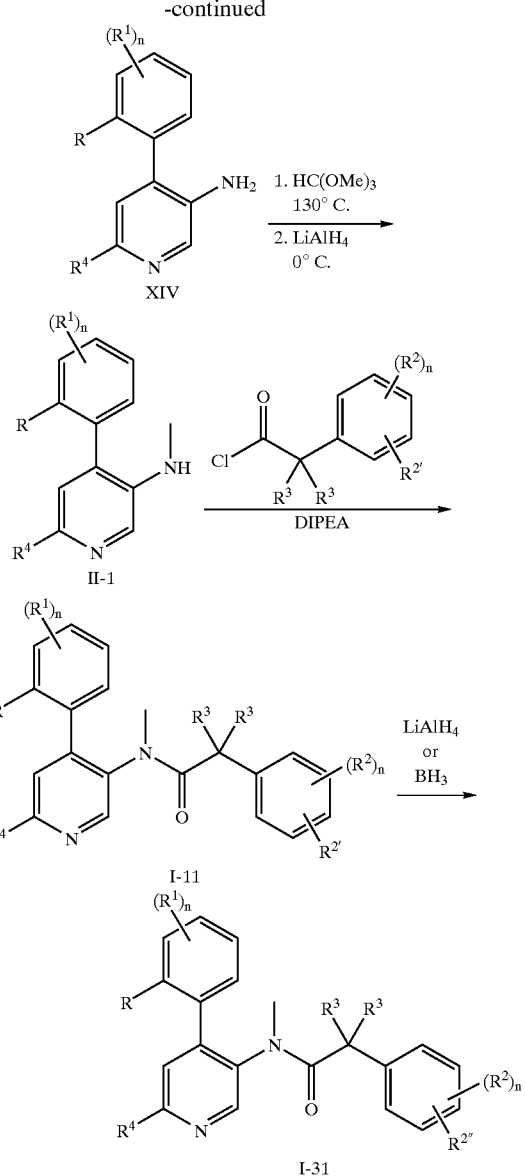

The definition of substituents is given above.

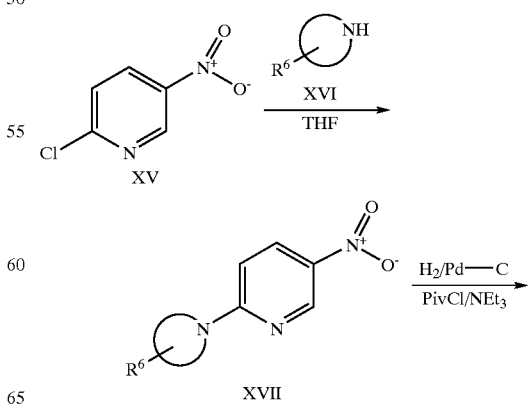

-continued
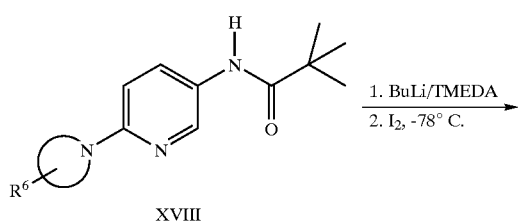
XVIII
1. BuLi/TMEDA
2. I₂, -78° C.
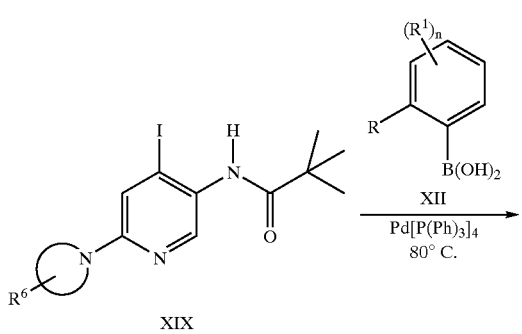
XIX
Pd[P(Ph)₃]₄
80° C.
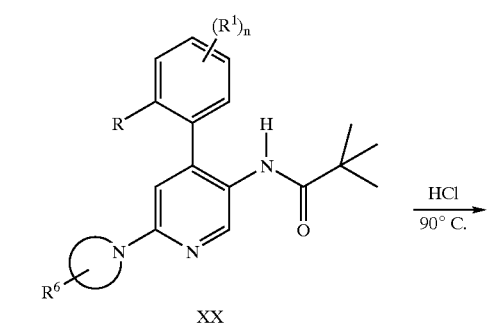
XX
HCl
90° C.
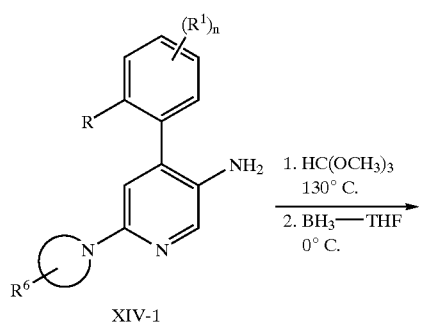
XIV-1
1. HC(OCH₃)₃
130° C.
2. BH₃—THF
0° C.
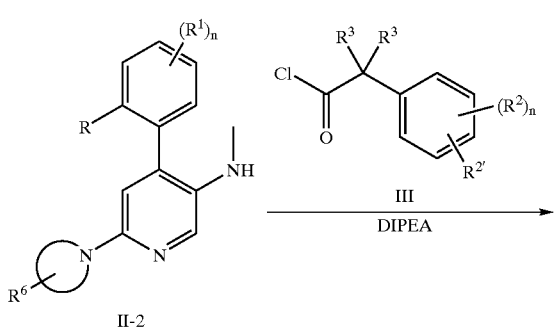
II-2
III
DIPEA
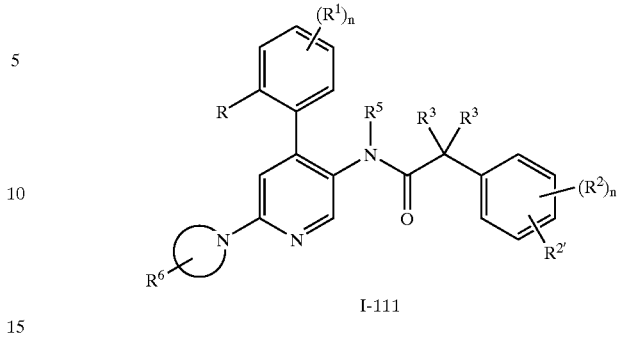
I-111
The definition of substituents is given above.
Scheme 3
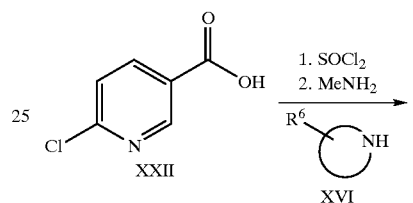
XXII
1. SOCl₂
2. MeNH₂
R⁶—NH
XVI
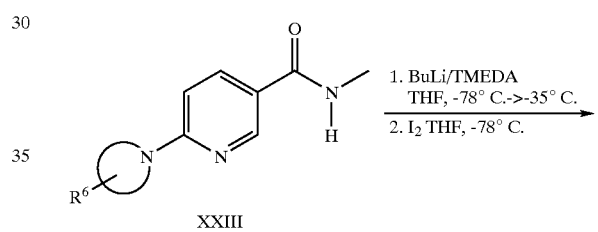
XXIII
1. BuLi/TMEDA
THF, -78° C.→-35° C.
2. I₂ THF, -78° C.
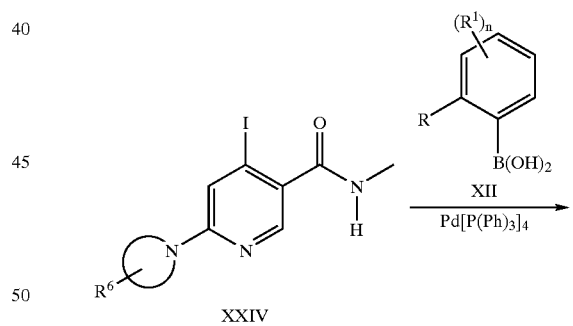
XXIV
Pd[P(Ph)₃]₄
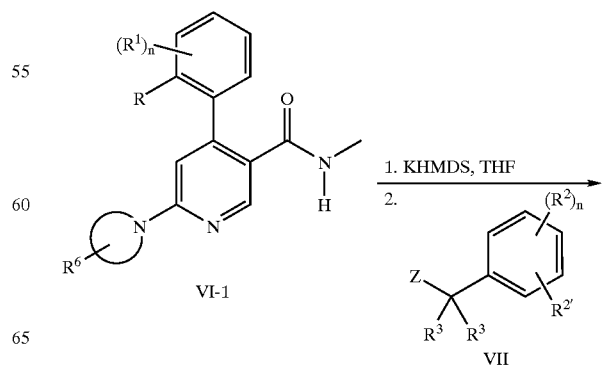
VI-1
1. KHMDS, THF
2. VII -continued
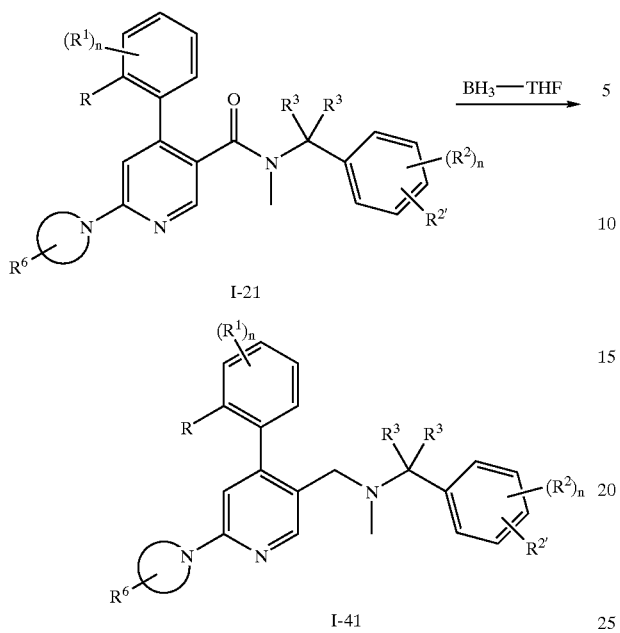
Z=Cl, Br, I or OS(O)$_2$C$_6$H$_4$CH$_3$
and the definition of the substituents is given above.
Scheme 4
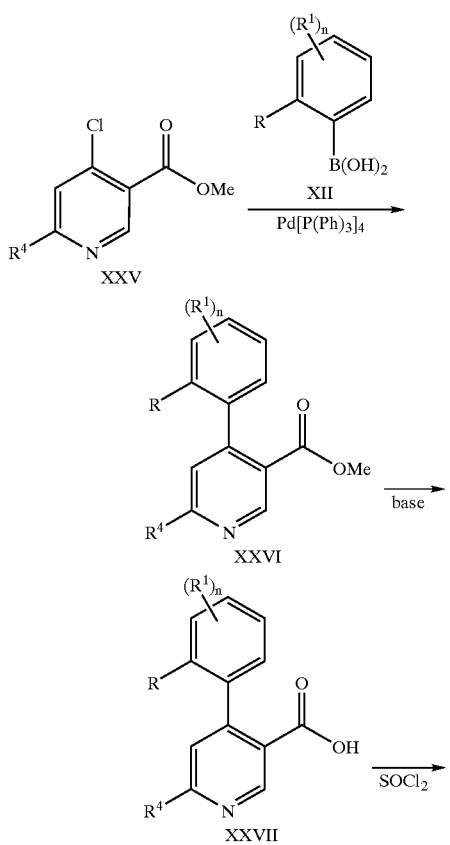
-continued
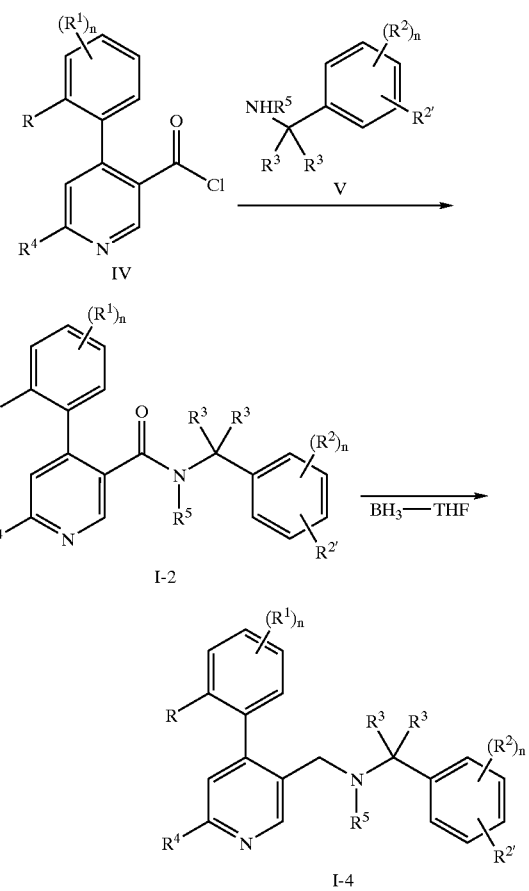
The definition of substituents is given above.
Scheme 5
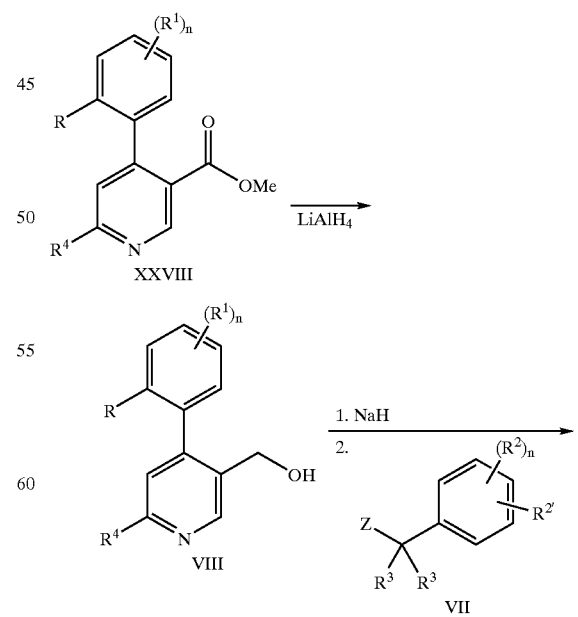

33
-continued
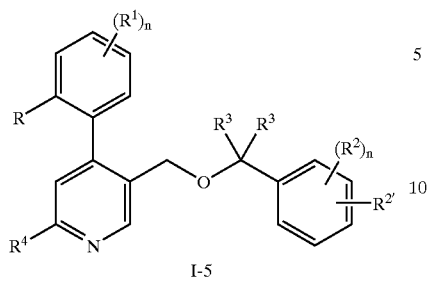
I-5
Z is Cl, Br, I or —OS(O)$_2$C$_6$H$_4$CH$_3$ and the definition of the other substituents is described above.
Scheme 6
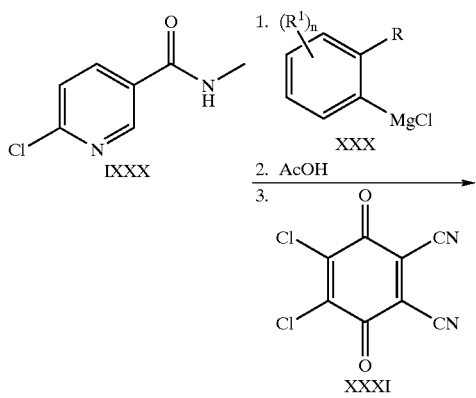
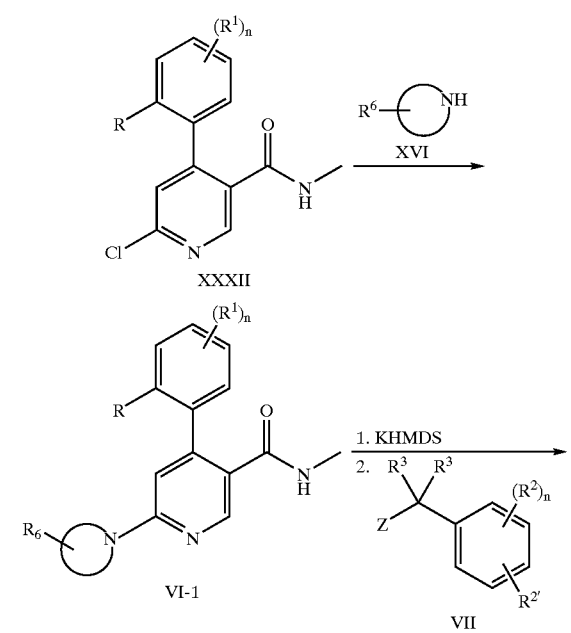
34
-continued
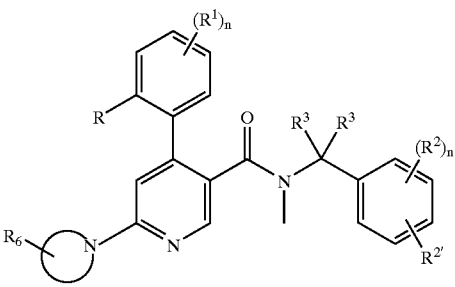
I-21
Z is Cl, Br, I or —OS(O)$_2$C$_6$H$_4$CH$_3$ and the definition of the other substituents is given above.
Scheme 7
The definition of substituents is given above.

Scheme 8

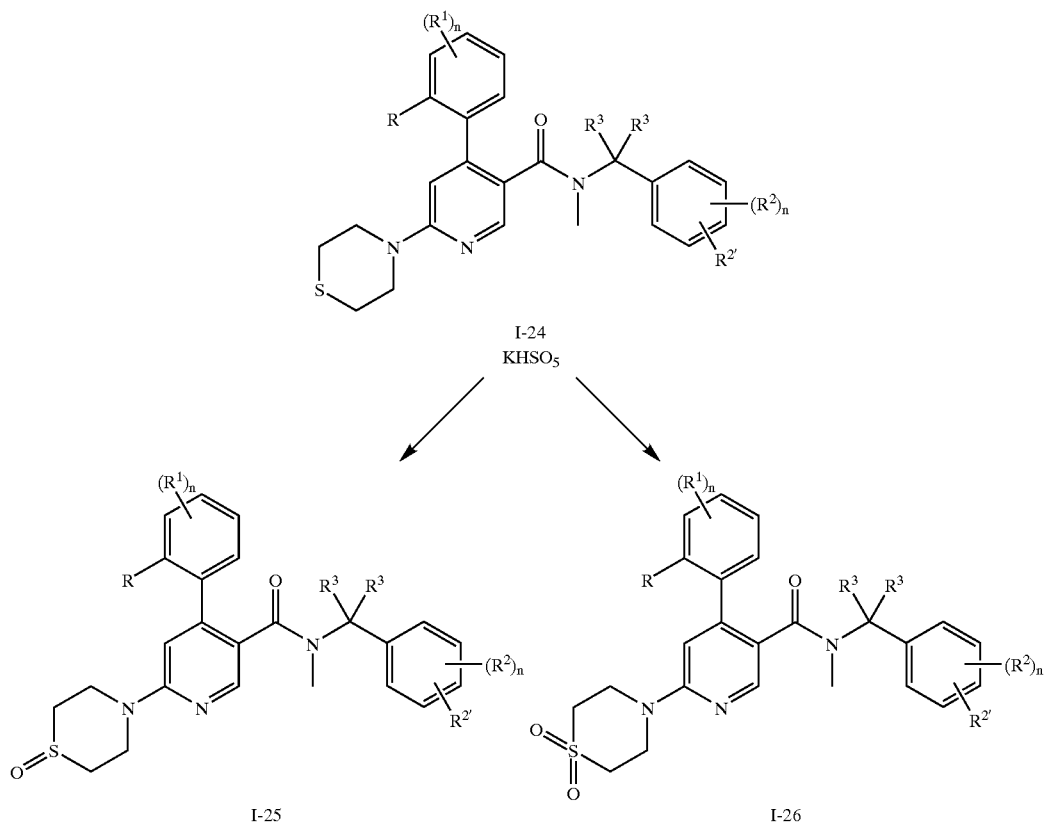

The definition of substituents is given above.

As mentioned earlier, the compounds of this invention and their pharmaceutically usable addition salts possess valuable pharmacological properties. It has been found that the compounds of the present invention are antagonists of the Neurokinin 1 (NK-1, substance P) receptor.

The compounds were investigated in accordance with the tests given hereinafter. These tests demonstrate the pharmacological activity of the compounds of this invention as NK-1 receptor antagonists. Such activity is correlated with treatment of pain and depression, for example that related to diseases caused by inflammation or to central nervous system disorders. A pKi in the range of about 8.0 to about 9.8 indicates an especially high affinity.

The affinity of test compounds for the $NK_1$ receptor was evaluated at human $NK_1$ receptors in CHO cells infected with the human $NK_1$ receptor (using the Semliki virus expression system) and radiolabelled with [$^3$H]substance P (final concentration 0.6 nM). Binding assays were performed in HEPES buffer (50 mM, pH 7.4) containing BSA (0.04%) leupeptin (8 µg/ml), $MnCl_2$ (3 mM) and phosphoramidon (2 µM). Binding assays consisted of 250 µl of membrane suspension ($1.25 \times 10^5$ cells/assay tube), 0.125 µl of buffer of displacing agent and 125 µl of [$^3$H]substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 2×2 ml washes of HEPES buffer (50 mM, pH 7.4). The radioactivity retained on the filters was measured by scintillation counting. All assays were performed in triplicate in at least 2 separate experiments.

The affinity to the NK-1 receptor, given as pKi, is in the scope of 8.00–9.80 for the preferred compounds. Examples of such compounds are

| | |
|---|---|
| N-(3,5-bis-trifluoromethyl-benzyl)-N-methyl-4-(2-chloro-phenyl)-nicotinamide | 8.20 |
| 2-(3,5-bis-trifluoromethyl-phenyl)-N-methyl-N-(4-o-tolyl-pyridin-3-yl)-isobutyramide | 8.47 |
| 2-(3,5-bis-trifluoromethyl-phenyl)-N-methyl-N-{6-[methyl-(2-morpholin-4-yl-ethyl)-amino]-4-o-tolyl-pyridin-3-yl}-isobutyramide | 8.70 |
| 2-(3,5-bis-trifluoromethyl-phenyl)-N-methyl-N-(6-piperazin-1-yl-4-o-tolyl-pyridin-3-yl)-isobutyramide | 9.0 |
| N-(3,5-Bis-trifluoromethyl-benzyl)-N-methyl-6-[4-(5-oxo-4,5-dihydro-1H-[1,2,4]triazol-3-ylmethyl)-piperazin-1-yl]-4-o-tolyl-nicotinamide | 9.54 |

All the compounds of this invention as well as their pharmaceutically usable acid addition salts can be used as medicaments, e.g. in the form of pharmaceutical compositions. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of this invention and their pharmaceutically usable acid addition salts can be processed with pharmaceutically inert, inorganic or organic excipients for the production of tablets, coated tablets, dragees and hard gelatine capsules. Lactose, corn starch or derivatives thereof, talc, stearic acid or its salts etc can be used as such excipients e.g. for tablets, dragées and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The effective amount for the dosage can vary within wide limits and will, of course, be fitted to the individual requirements in each particular case. In general, in the case of oral administration a daily dosage of about 10 to 1000 mg per person of a compound of this invention should be appropriate, although the above upper limit can also be exceeded when necessary.

The following Examples illustrate the present invention without limiting it. All temperatures are given in degrees Celsius.

Table of Examples

| R | $R^1$ | $R^2$ | $R^{2'}$ | $R^3$ | $R^4$ | | X | Ex. No. |
|---|---|---|---|---|---|---|---|---|
| $CH_3$ | H | 3-$CF_3$ | 5-$CF_3$ | H/H | H | | —CON($CH_3$)— | 1 |
| Cl | H | 3-$CF_3$ | 5-$CF_3$ | H/H | H | | —CON($CH_3$)— | 2 |
| $CF_3$ | H | 3-$CF_3$ | 5-$CF_3$ | H/H | H | | —CON($CH_3$)— | 3 |
| F | H | 3-$CF_3$ | 5-$CF_3$ | H/H | H | | —CON($CH_3$)— | 4 |
| $OCH_3$ | H | 3-$CF_3$ | 5-$CF_3$ | H/H | H | | —CON($CH_3$)— | 5 |
| H | H | 3-$CF_3$ | 5-$CF_3$ | H/H | H | | —CON($CH_3$)— | 6 |
| $CH_3$ | H | 3-$CF_3$ | 5-$CF_3$ | H/H | H | | —CON($CH_2CH_3$)— | 7 |
| $CH_3$ | H | 3-$CF_3$ | 5-$CF_3$ | H/H | H | | —CON(cyclopropyl)- | 8 |
| $CH_3$ | H | 3-$CF_3$ | 5-$CF_3$ | H/$CH_3$ | H | | —CON($CH_3$)— | 9 |
| $CH_3$ | H | 3-F | 5-F | H/H | H | | —CON($CH_3$)— | 10 |
| $CH_3$ | H | 3-Cl | 5-Cl | H/H | H | | —CON($CH_3$)— | 11 |
| $CH_3$ | H | 3-$CF_3$ | 5-$CF_3$ | H/H | | 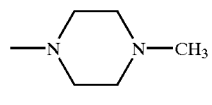 | —CON($CH_3$)— | 12 |
| Cl | H | 3-$CF_3$ | 5-$CF_3$ | H/H | | 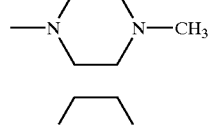 | —CON($CH_3$)— | 13 |
| $CH_3$ | H | 3-$CF_3$ | 5-$CF_3$ | $CH_3$/$CH_3$ | | 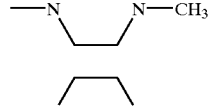 | —N($CH_3$)CO— | 14 |
| Cl | H | 3-$CF_3$ | 5-$CF_3$ | $CH_3$/$CH_3$ | | 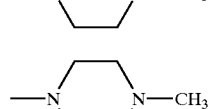 | —N($CH_3$)CO— | 15 |
| $CH_3$ | 4-F | 3-$CF_3$ | 5-$CF_3$ | $CH_3$/$CH_3$ | | 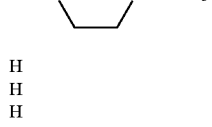 | —N($CH_3$)CO— | 16 |
| Cl | H | 3-$CF_3$ | 5-$CF_3$ | $CH_3$/$CH_3$ | H | | —N($CH_3$)CO— | 17 |
| $CH_3$ | H | 3-$CF_3$ | 5-$CF_3$ | $CH_3$/$CH_3$ | H | | —N($CH_3$)CO— | 18 |
| $CH_3$ | H | 3-$CF_3$ | 5-$CF_3$ | $CH_3$/$CH_3$ | H | | —NHCO— | 19 |
| $CH_3$ | H | 3-$CF_3$ | 5-$CF_3$ | H/H | H | | —N($CH_3$)CO— | 20 |
| $CH_3$ | H | 3-$CF_3$ | 5-$CF_3$ | H/$CH_3$ | H | | —N($CH_3$)CO— | 21 |
| Cl | H | 3-$CF_3$ | 5-$CF_3$ | cyclopropyl | H | | —N($CH_3$)CO— | 22 |
| $CH_3$ | H | 3-$CF_3$ | 5-$CF_3$ | $CH_3$/$CH_3$ | | 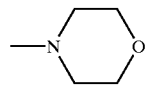 | —N($CH_3$)C(O)— | 23 |
| Cl | H | 3-$CF_3$ | 5-$CF_3$ | $CH_3$/$CH_3$ | | 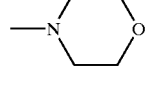 | —N($CH_3$)C(O)— | 24 |

-continued

Table of Examples

| R | R¹ | R² | R²' | R³ | R⁴ | X | Ex. No. |
|---|---|---|---|---|---|---|---|
| CH₃ | H | 3-CF₃ | 5-CF₃ | CH₃/CH₃ | 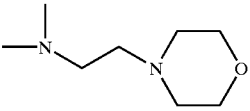 | —N(CH₃)C(O)— | 25 |
| CH₃ | H | 3-CF₃ | 5-CF₃ | CH₃/CH₃ | 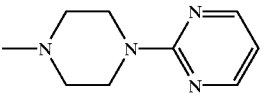 | —N(CH₃)C(O)— | 26 |
| CH₃ | H | 3-CF₃ | 5-CF₃ | CH₃/CH₃ | 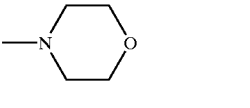 | —NHC(O)— | 27 |
| Cl | H | 3-CF₃ | 5-CF₃ | CH₃/CH₃ | 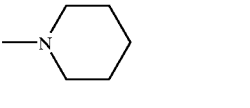 | —N(CH₃)C(O)— | 28 |
| CH₃ | H | 3-CF₃ | 5-CF₃ | CH₃/CH₃ | —N(CH₃)₂ | —N(CH₃)C(O)— | 29 |
| Cl | H | 3-CF₃ | 5-CF₃ | CH₃/CH₃ | —N(CH₃)₂ | —N(CH₃)C(O)— | 30 |
| CH₃ | H | 3-CF₃ | 5-CF₃ | CH₃/CH₃ | 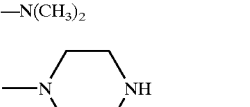 | —N(CH₃)C(O)— | 31 |
| CH₃ | H | 3-CF₃ | 5-CF₃ | CH₃/CH₃ | 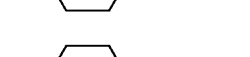 | —N(CH₃)C(O)— | 32 |
| CH₃ | H | 3-CF₃ | 5-CF₃ | CH₃/CH₃ | —N(CH₃)(CH₂)₂OH | —N(CH₃)C(O)— | 33 |
| CH₃ | H | 3-CF₃ | 5-CF₃ | CH₃/CH₃ |  | —N(CH₃)C(O)— | 34 |
| CH₃ | H | 3-CF₃ | 5-CF₃ | H/H | 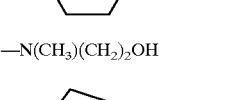 | —N(CH₃)C(O)— | 35 |
| CH₃ | H | 3-OCH₃ | 5-OCH₃ | H/H | 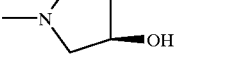 | —N(CH₃)C(O)— | 36 |
| CH₃ | H | 3-F | 5-CF₃ | H/H | 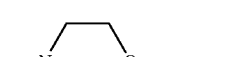 | —N(CH₃)C(O)— | 37 |
| CH₃ | F | 3-CF₃ | 5-CF₃ | CH₃/CH₃ | 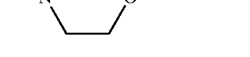 | —N(CH₃)CH₂— | 38 |
| CH₃ | H | 3-CF₃ | 5-CF₃ | H/H | H | —CH₂N(CH₃)— | 39 |
| CH₃ | H | 3-CF₃ | 5-CF₃ | H/H | H | —CH₂—O— | 40 |
| are together —CH=CH— CH=CH | | 3-CF₃ | 5-CF₃ | H/H | 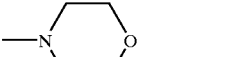 | —C(O)N(CH₃)— | 41 |
| Cl | H | 3-CF₃ | 5-CF₃ | H/H | 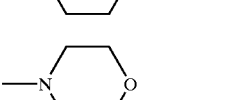 | —CH₂N(CH₃)— | 42 |

-continued
Table of Examples
| R | R¹ | R² | R²' | R³ | R⁴ | X | Ex. No. |
|---|---|---|---|---|---|---|---|
| CH₃ | H | 3-CF₃ | 5-CF₃ | H/H | 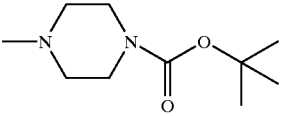 | —C(O)N(CH₃)— | 43 |
| CH₃ | H | 3-CF₃ | 5-CF₃ | H/H | 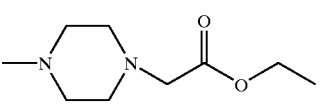 | —C(O)N(CH₃)— | 44 |
| CH₃ | H | 3-CF₃ | 5-CF₃ | H/H | 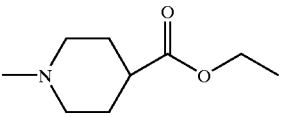 | —C(O)N(CH₃)— | 45 |
| CH₃ | H | 3-CF₃ | 5-CF₃ | H/H | 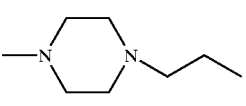 | —C(O)N(CH₃)— | 46 |
| CH₃ | H | 3-CF₃ | 5-CF₃ | H/H | 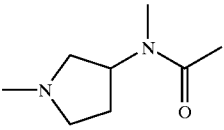 | —C(O)N(CH₃)— | 47 |
| CH₃ | H | 3-CF₃ | 5-CF₃ | H/H | 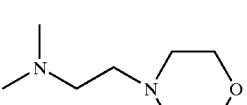 | —C(O)N(CH₃)— | 48 |
| CH₃ | H | 3-CF₃ | 5-CF₃ | H/H | 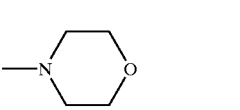 | —C(O)N(CH₃)— | 49 |
| CH₃ | H | 3-CF₃ | 5-CF₃ | H/H | 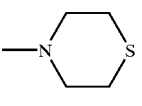 | —C(O)N(CH₃)— | 50 |
| CH₃ | H | 3-CF₃ | 5-CF₃ | H/H | 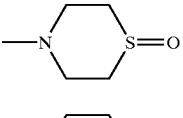 | —C(O)N(CH₃)— | 51 |
| CH₃ | H | 3-CF₃ | 5-CF₃ | H/H | 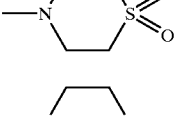 | —C(O)N(CH₃)— | 52 |
| CH₃ | H | 3-CF₃ | 5-CF₃ | H/H | 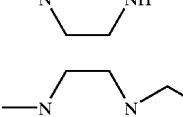 | —C(O)N(CH₃)— | 53 |
| CH₃ | H | 3-CF₃ | 5-CF₃ | H/H | 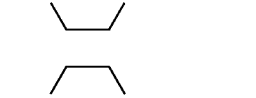 | —C(O)N(CH₃)— | 54 |
| CH₃ | H | 3-CF₃ | 5-CF₃ | H/H | 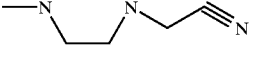 | —C(O)N(CH₃)— | 55 |

-continued

Table of Examples

| R | R¹ | R² | R²' | R³ | R⁴ | X | Ex. No. |
|---|---|---|---|---|---|---|---|
| CH₃ | H | 3-CF₃ | 5-CF₃ | H/H | 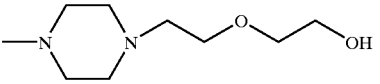 | —C(O)N(CH₃)— | 56 |
| CH₃ | H | 3-CF₃ | 5-CF₃ | H/H | 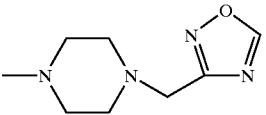 | —C(O)N(CH₃)— | 57 |
| CH₃ | H | 3-CF₃ | 5-CF₃ | H/H | 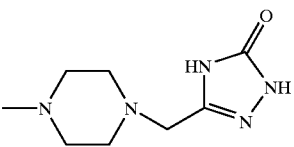 | —C(O)N(CH₃)— | 58 |
| CH₃ | H | 3-CF₃ | 5-CF₃ | H/H | 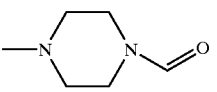 | —C(O)N(CH₃)— | 59 |
| CH₃ | H | are together —CH=CH—CH=CH— subst. by CH₃ | | H/H | 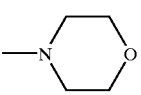 | —C(O)N(CH₃)— | 60 |
| CH₃ | H | are together —CH=CH—CH=CH— | | H/H | 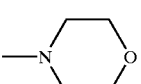 | —C(O)N(CH₃)— | 61 |
| CH₃ | H | are together —CH=CH—CH=CH— subst. by OCH₃ | | H/H | 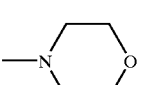 | —C(O)N(CH₃)— | 62 |
| CH₃ | H | 2-OCH₃ | H | H/H | 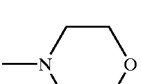 | —C(O)N(CH₃)— | 63 |
| CH₃ | H | 2-OCH₃ | 5-Cl | H/H | 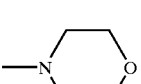 | —C(O)N(CH₃)— | 64 |
| CH₃ | H | 2-Cl | 5-OCH₃ | H/H | 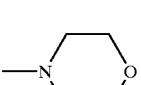 | —C(O)N(CH₃)— | 65 |
| CH₃ | H | 2,3,4,5-F n = 4 | 6-F | H/H | 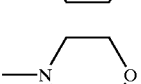 | —C(O)N(CH₃)— | 66 |
| CH₃ | H | are together —CH=CH—CH=CH— | | H/H | 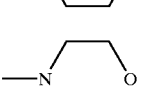 | —C(O)N(CH₃)— | 67 |
| CH₃ | H | 2-OCH₃ | 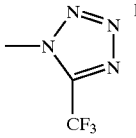 | H/H | 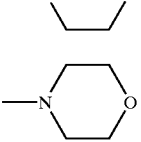 | —C(O)N(CH₃)— | 68 |

-continued

Table of Examples

| R | R¹ | R² | R²' | R³ | R⁴ | X | Ex. No. |
|---|---|---|---|---|---|---|---|
| CH₃ | H | are together —CH=CH—CH=CH₂—, subst. by di-OCH₃ | | H/H | morpholine (—N(CH₂CH₂)₂O) | —C(O)N(CH₃)— | 69 |
| CH₃ | H | 3-CF₃ | 5-CF₃ | H/H | 4-carboxypiperidinyl | —C(O)N(CH₃)— | 70 |
| CH₃ | H | 3-CF₃ | 5-CF₃ | H/H | piperazinyl-CH₂-tetrazole | —C(O)N(CH₃)— | 71 |
| CH₃ | H | 3-CF₃ | 5-CF₃ | H/H | —N(H)—CH₂—C₆H₅ | —N(CH₃)C(O)— | 72 |
| CH₃ | H | 3-CF₃ | 5-CF₃ | CH₃/CH₃ | —NH₂ | —N(CH₃)C(O)— | 73 |
| CH₃ | H | 3-CF₃ | 5-CF₃ | CH₃/CH₃ | —N=CH—N(CH₃)₂ | —N(CH₃)C(O)— | 74 |
| CH₃ | H | 3-CF₃ | 5-CF₃ | CH₃/CH₃ | —NH—S(O)₂CH₃ | —N(CH₃)C(O)— | 75 |
| CH₃ | H | 3-CF₃ | 5-CF₃ | CH₃/CH₃ | —HN—S(O)₂—C₆H₅ | —N(CH₃)C(O)— | 76 |

EXAMPLE 1

N-(3,5-bis-Trifluoromethyl-benzyl)-N-methyl-4-o-tolyl-nicotinamide a) Methyl 4-o-Tolyl-nicotinoate A mixture of 1.2 g (6.9 mmol) methyl 4-chloronicotinoate, 20 ml dimethoxyethane, 6.4 ml 2 N sodium carbonate solution, 0.4 g (0.34 mmol) tetrakis(triphenylphosphine)palladium(0) and 1.4 g (10.3 mmol) o-tolylboronic acid was heated under argon at 80° C. for 18 h. After cooling to room temperature, the aqueous phase was separated and washed twice with ethyl acetate. The combined organic layers were washed with 50 ml brine, dried (sodium sulfate), evaporated and dried in vacuo. The crude oil was subjected to column chromatography to yield 1.5 g (97%) of the title compound as an oil that crystallized upon storage at 0° C.

MS m/e (%): 227 (M⁺, 15).

b) 4-o-Tolyl-nicotinic Acid

A solution of 1.13 g (5.0 mmol) methyl 4-o-tolyl-nicotinoate in 15 ml ethanol and 12 ml 2 N sodium hydroxide solution was heated to reflux for 1 h. The pH was adjusted to 5 and the mixture was extracted twice with ethyl acetate. The combined organic layers were dried (sodium sulfate) and evaporated to give 1 g (94%) of the title compound as off white crystals.

M.p. 201–202° C.

c) N-(3,5-bis-Trifluoromethyl-benzyl)-N-methyl-4-o-tolyl-nicotinamide

A solution of 1 g (4.6 mmol) 4-o-tolyl-nicotinic acid in 10 ml dichloromethane and 2 drops of N,N-dimethylformamide was stirred with 1 ml (14 mmol) thionyl chloride for 2 h at room temperature. The solvent was removed and the residue was taken up in 10 ml toluene and 2 ml triethylamine. After the addition of 1.3 g (5.1 mmol) 3,5-bis-trifluorobenzyl-methyl amine the mixture was refluxed for 1 h and extracted twice with ethyl acetate and washed with sodium bicarbonate. The combined organic layers were dried (sodium sulfate) and evaporated. The crude oil was subjected to column chromatography to give 1.4 g (67%) of the title compound as an oil.

MS m/e (%): 452 (M⁺, 5).

EXAMPLE 2

N-(3,5-bis-Trifluoromethyl-benzyl)-N-methyl-4-(2-chloro-phenyl)-nicotinamide

The title compound was obtained as an oil in comparable yields according to the procedures described above for the preparation of Example 1. using o-chlorophenylboronic acid instead of o-tolylboronic acid in step a).

MS m/e (%): 471 (M⁺, 3).

EXAMPLE 3

N-(3,5-bis-Trifluoromethyl-benzyl)-N-methyl-4-(2-trifluoromethyl-phenyl)-nicotinamide The title compound was obtained as an oil in comparable yields according to the procedures described above for the preparation of Example 1 using o-trifluoromethylphenylboronic acid instead of o-tolylboronic acid in step a).

MS m/e (%): 506 (M⁺, 15).

EXAMPLE 4

N-(3,5-bis-Trifluoromethyl-benzyl)-N-methyl-4-(2-fluoro-phenyl)-nicotinamide

The title compound was obtained as an oil in comparable yields according to the procedures described above for the preparation of Example 1 using o-fluorophenylboronic acid instead of o-tolylboronic acid in step a).

MS m/e (%): 456 (M$^+$, 30).

EXAMPLE 5

N-(3,5-bis-Trifluoromethyl-benzyl)-N-methyl-4-(2-methoxy-phenyl)-nicotinamide

The title compound was obtained as an oil in comparable yields according to the procedures described above for the preparation of Example 1 using o-methoxyphenylboronic acid instead of o-tolylboronic acid in step a).

MS m/e (%): 469 (M+H$^+$, 100).

EXAMPLE 6

N-(3,5-bis-Trifluoromethyl-benzyl)-N-methyl-4-phenyl-nicotinamide

The title compound was obtained as an oil in comparable yields according to the procedures described above for the preparation of Example 1 using phenylboronic acid instead of o-tolylboronic acid in step a).

MS m/e (%): 438 (M$^+$, 60).

EXAMPLE 7

N-(3,5-bis-Trifluoromethyl-benzyl)-N-ethyl-4-o-tolyl-nicotinamide

The title compound was obtained as an oil in comparable yields according to the procedures described above for the preparation of Example 1 using 3,5-bis-trifluorobenzyl-ethyl amine instead of 3,5-bis-trifluorobenzyl-methyl amine in step c). MS m/e (%): 465 (M–H$^-$, 3).

EXAMPLE 8

N-(3,5-bis-Trifluoromethyl-benzyl)-N-cyclopropyl-4-o-tolyl-nicotinamide Hydrochloride (1:0.8)

a) N-(3,5-bis Trifluoromethyl-benzyl)-N-cyclopropyl-4-o-tolyl-nicotinamide

A solution of 106 mg (0.5 mmol) 4-o-tolyl-nicotinic acid in 5 ml dichloromethane and 2 drops N,N-dimethylformamide was stirred with 0.1 ml (1.4 mmol) thionyl chloride for 1.5 h at room temperature. The solvent was removed and the residue was taken up in 5 ml dichloromethane and 0.3 ml triethylamine. After the addition of 155 mg (0.55 mmol) (3,5-bis-trifluoromethyl-benzyl)-cyclopropyl-amine the mixture was stirred at room temperature for 1 h and washed twice with water. The organic layer was dried (magnesium sulfate) and evaporated. The crude oil was subjected to column chromatography to give 140 mg (58%) of the title compound as an oil.

MS m/e (%): 479 (M$^+$, 100).

b) N-(3,5-bis Trifluoromethyl-benzyl)-N-cyclopropyl-4-o-tolyl-nicotinamide Hydrochloride (1:0.8)

To a solution of 140 mg N-(3,5-bis trifluoromethyl-benzyl)-N-cyclopropyl-4-o-tolyl-nicotinamide in 1 ml diethyl ether were added 3 drops of 3 N hydrochloric acid solution in methanol. After stirring for 15 min at 0° C., the mixture was evaporated to dryness to give 100 mg (41%) of the title compound as white crystals. M.p. 174–178° C.

MS m/e (%): 479 (M$^+$, 100).

EXAMPLE 9

N-[1-(3,5-bis-Trifluoromethyl-phenyl)-ethyl]-N-methyl-4-o-tolyl-nicotinamide

The title compound was obtained as an oil in comparable yields according to the procedures described above for the preparation of Example 1 using 2-(3,5-bis-trifluorophenyl) ethyl-methyl amine instead of 3,5-bis-trifluorobenzyl-methyl amine in step c).

MS m/e (%): 467 (M+H$^+$, 100).

EXAMPLE 10

N-(3,5-di-Fluorobenzyl)-N-methyl-4-o-tolyl-nicotinamide

The title compound was obtained as a solid in comparable yields according to the procedures described above for the preparation of Example 1 using 3,5-difluorobenzyl-methyl amine instead of 3,5-bis-trifluorobenzyl-methyl amine in step c).

MS m/e (%): 353 (M+H$^+$, 100).

EXAMPLE 11

N-(3,5-di-Chlorobenzyl)-N-methyl-4-o-tolyl-nicotinamide

The title compound was obtained as an oil in comparable yields according to the procedures described above for the preparation of Example 1 using 3,5-dichlorobenzyl-methyl amine instead of 3,5-bis-trifluorobenzyl-methyl amine in step c).

MS m/e (%): 385 (M+H$^+$, 100), 387 (M+H$^+$, 70).

EXAMPLE 12

N-(3,5-bis-Trifluoromethyl-benzyl)-N-methyl-6-(4-methyl-piperazin-1-yl)-4-o-tolyl-nicotinamide Hydrochloride (1:2)

a) 6-Chloro-N-methyl-nicotinamide

To 50 g (317 mmol) of 2-chloronicotinic acid was added 230 ml (3.16 mol) thionyl chloride at 0° C. After heating the mixture at reflux for 2 h excess thionyl chloride was removed by distillation. The oily brown residue was dissolved in 250 ml dichloromethane. The solution was treated with methylamine gas at 0° C. until no exothermic reaction was observed any longer. The resulting suspension was diluted with 1000 ml dichloromethane/water. The layers were separated and the aqueous layer extracted with three 300 ml portions of dichloromethane. Drying of the organic layer with sodium sulfate and concentration gave 53.2 g (98%) of the title compound as a light yellow solid.

MS m/e (%): 171 (M+H$^+$, 15).

b) N-Methyl-6-(4-methyl-piperazin-1-yl)-nicotinamide

A mixture of 52.0 g (30.5 mmol) 6-chloro-N-methyl-nicotinamide and 176 ml (1.58 mol) 1-methylpiperazine was heated at 100° C. for 1.5 h in an autoclave. After cooling to room temperature excess 1-methylpiperazine was removed by distillation. The residue was partitioned in 1000 ml dichloromethane/1 N aqueous sodium hydroxide solution. The layers were separated and the aqueous layer was extracted with three 500 ml portions of dichloromethane. Concentration and short column chromatography yielded 72.3 g (97%) of the title compound as a light brown solid.

MS m/e (%): 235 (M+H$^+$, 100).

c) 4-Iodo-N-methyl-6-(4-methyl-piperazin-1-yl)-nicotinamide

To a solution of 936 mg (3.99 mmol) N-methyl-6-(4-methyl-piperazin-1-yl)-nicotinamide and 2.46 ml (16.4 mmol) N,N,N',N'-tetramethylethylenediamine in 20 ml dry tetrahydrofuran 10 ml (16 mmol) of a 1.6 M solution of n-butyllithium in hexane were added dropwise at –78° C. After 0.5 h the mixture was warmed to –35° C. Stirring was continued for 3 h at that temperature. After cooling to −78° C. a solution of 1.52 g (6.00 mmol) iodine in 2.5 ml tetrahydrofuran was added. The reaction mixture was allowed to warm up to room temperature overnight. The reaction mixture was quenched with 30 ml of a 20% aqueous sodium hydrogensulfite solution at 0° C. Extraction with three 30 ml portions of ethyl acetate, drying with sodium sulfate and concentration gave 1.2 g of a brown oil. Column chromatography afforded 618 mg (43%) of the title compound.

MS m/e (%): 360 (M$^+$, 15).

d) N-Methyl-6-(4-methyl-piperazin-1-yl)-4-o-tolyl-nicotinamide

A suspension of 4.00 g (11.1 mmol) 4-iodo-N-methyl-6-(4-methyl-piperzin-1-yl)-nicotinamide and 642 mg (0.555 mmol) tetrakis(triphenylphosphine)palladium(0) in 60 ml toluene was dioxygenated with a stream of argon for 30 min. After addition of 11 ml of a 2 N aqueous solution of sodium carbonate and 1.66 g (12.2 mmol) o-tolylboronic acid, the mixture was heated at reflux overnight. Cooling to room temperature was followed by dilution with water and extraction with three 50 ml portions of ethyl acetate. The aqueous layer was saturated with sodium chloride and extracted with three 50 ml portions of dichloromethane. The combined organic layers were dried with sodium sulfate and concentrated. Column chromatography afforded 2.26 g (63%) of the tide compound.

MS m/e (%): 324 (M$^+$, 5).

e) N-(3,5-bis-Trifluoromethyl-benzyl)-N-methyl-6-(4-methyl-piperazin-1-yl)-4-o-tolyl-nicotinamide Hydrochloride (1:2)

To a solution of 750 mg (2.32 mmol) N-methyl-6-(4-methyl-piperazin-1-yl)-4-o-tolyl-nicotinamide in 16 ml tetrahydrofuran, 3 ml of a 1 M solution (3 mmol) of potassium hexamethyldisilazide in tetrahydrofuran was added at room temperature. After 1 h, 0.43 ml (2.3 mmol) 3,5-bis(trifluoromethyl)benzyl bromide was added dropwise to the resulting suspension. The reaction was quenched with water after 1 h and the mixture was extracted with three 20 ml portions of ethyl acetate. The combined organic extracts were washed with saturated aqueous sodium chloride solution, dried with sodium sulfate and concentrated. Column chromatography gave 950 mg (74%) N-(3,5-bis-trifluoromethyl-benzyl)-N-methyl-6-(4-methyl-piperazin-1-yl)-4-o-tolyl-nicotinamide. The white foam was dissolved in a small amount of diethyl ether and treated with 2 ml 3 N hydrochloric acid solution in diethyl ether. Concentration afforded 1.02 g (74%) of the title compound as a white solid.

MS m/e (%): 551 (M+H$^+$, 100).

EXAMPLE 13

N-(3,5-bis-Trifluoromethyl-benzyl)-4-(2-chloro-phenyl)-N-methyl-6-(4-methyl-piperazin-1-yl)-nicotinamide Hydrochloride (1:2)

The title compound was prepared analogously to the preparation of Example 12 using 2-chlorophenylboronic acid instead of o-tolylboronic acid in step d).

MS m/e (%): 571 (M+H$^+$, 100)

EXAMPLE 14

2-(3,5-bis-Trifluoromethyl-phenyl)-N-methyl-N-[6-(4-methyl-piperan-1-yl)-4-o-tolyl-pyridin-3-yl]-isobutyramide Hydrochloride (1:2)

a) 1-Methyl-4-(5-nitro-pyridin-2-yl)-piperazine

To a solution of 20 g (126 mmol) of 2-chloro-5-nitropyridine in 200 ml tetrahydrofuran were added dropwise 35 ml (315 mmol) 1-methylpiperazine within 10 min. The reaction mixture was refluxed for additional 1.5 h. After cooling to room temperature, the solvent was removed in vacuo and the residue was re-dissolved in 200 ml ethyl acetate. The organic phase was washed with 200 ml 1 N sodium bicarbonate solution, dried (magnesium sulfate) and evaporated to give 27.9 g (quantitative) of the title compound as a yellow solid.

MS m/e (%): 223 (M+H$^+$, 100).

b) 2,2-Dimethyl-N-[6-(4-methyl-piperazin-1-yl)-pyridin-3-yl-propionamide

To a solution of 27.9 g (125.5 mmol) of 1-methyl-4-(5-nitro-pyridin-2-yl)-piperazine in 400 ml methanol were added 2.6 g of 10% of palladium on activated charcoal. The reaction mixture was hydrogenated (room temperature to ca. 45° C., 1 bar) until the theoretical amount of hydrogen was taken up (about 2 h). The catalyst was filtered off and was washed twice with 100 ml portions of methanol. The filtrate was evaporated in vacuo to give 28 g of a purple oil which consisted to ca. 90% of the desired aniline derivative according to analysis by thin layer chromatography.

This crude product was dissolved in a mixture of 400 ml tetrahydrofuran and 100 ml diethyl ether. After cooling to 0° C., 30 ml (215 mmol) of triethylamine were added in one portion. Stirring was continued while 26 g (215 mmol) of pivaloyl chloride were added dropwise within a period of 10 min. The ice bath was removed and the reaction mixture was stirred for 1 h at room temperature. Then, the solvent was removed in vacuo and the residue was suspended in 200 ml 1 N sodium bicarbonate solution. The product was extracted three times with 200 ml portions of dichloromethane, dried (sodium sulfate) and purified by flash chromatography to give 30 g (86%) of the title compound as pink crystals.

MS m/e (%): 277 (M+H$^+$, 100).

c) N-[4-Iodo-6-(4-methyl-piperazin-1-yl)-pyridin-3-yl]-2,2-dimethyl-propionamide A solution of 30 g (108 mmol) 2,2-dimethyl-N-[6-(4-methyl-piperazin-1-yl)-pyridin-3-yl]-propionamide and 58 ml (380 mmol) N,N,N',N'-tetramethylethylenediamine under argon in 650 ml tetrahydrofuran was cooled in a dry ice bath to −78° C. Within 1 h, 239 ml (380 mmol) of a 1.6 N n-butyllithium solution in hexane were added dropwise. The reaction mixture was allowed to warm up to −30° C. overnight. After cooling again to −78° C., 43.6 g (170 mmol) iodine dissolved in 60 ml tetrahydrofuran were added dropwise during 15 min. The dry ice bath was replaced by an ice bath and a solution of 90 g (363 mmol) sodium thiosulfate pentahydrate in 250 ml water were added within 10 min when the temperature of the reaction mixture had reached 0° C. Then, 1000 ml diethyl ether were added and the organic layer was separated. The aqueous layer was extracted twice with 500 ml dichloromethane and the combined organic layers were dried (magnesium sulfate) and evaporated. Flash chromatography gave 18.5 g (42%) of the tide compound as a light brown oil which crystallized upon standing at room temperature.

MS m/e (%): 403 (M+H$^+$, 100).

d) 2,2-Dimethyl-N-[6-(4-methyl-piperazin-1-yl)-4-o-tolyl-pyridin-3-yl]-propionamide A mixture of 54 g (134 mmol) N-[4-iodo-6-(4-methyl-piperazin-1-yl)-pyridin-3-yl]-2,2-dimethyl-propionamide, 420 ml toluene, 150 ml 2 N sodium carbonate solution, 4.63 g (3.9 mmol) tetrakis(triphenylphosphine)palladium(0) and 20.16 g (147 mmol) o-tolylboronic acid was heated under argon at 80° C. for 12 h. After cooling to room temperature, the aqueous phase was separated and washed twice with toluene. The combined organic layers were washed with 50 ml brine, dried (sodium sulfate), evaporated and dried in vacuo to yield 49 g (quantitative) of the title compound as a brown oil.

MS m/e (%): 367 (M+H+, 100).

e) 6-(4-Methyl-piperazin-1-yl)-4-o-tolyl-pyridin-3-ylamine

A suspension of 56 g (152 mmol) 2,2-dimethyl-N-[6-(4-methyl-piperazin-1-yl)-4-o-tolyl-pyridin-3-yl]-propionamide in 1300 ml 3 N hydrochloric acid solution was heated to 90–95° C. overnight. The reaction mixture was cooled to room temperature, washed with three 500 ml portions diethyl ether and filtered over celite. The filtrate was diluted with 500 ml water and was adjusted to pH 7–8 by addition of 28% sodium hydroxide solution under ice cooling. The product was extracted with four 1000 ml portions of dichloromethane. The combined organic layers were washed with 500 ml brine, dried (magnesium sulfate) and evaporated to give 35 g (82%) of the title compound as a light brown oil.

MS m/e (%):283 (M+H+, 100).

f) Methyl-[6-(4-methyl-piperazin-1-yl)-4-o-tolyl-pyridin-3-yl]-amine

A solution of 35 g (124 mmol) 6-(4-methyl-piperazin-1-yl)-4-o-tolyl-pyridin-3-ylamine in 270 ml trimethyl orthoformate and 8 drops trifluoroacetic acid was heated for 3 h at 130° C. The reaction mixture was evaporated and dried in vacuo for 30 min. The residual oil was dissolved in 100 ml tetrahydrofuran and was added dropwise under ice cooling to 9.4 g (248 mmol) lithium aluminum hydride in 300 ml tetrahydrofuran. The reaction mixture was stirred for 1 h at room temperature, cooled to 0° C. again and acidified (pH 1–2) by addition of 28% hydrochloric acid solution. After stirring for 5 min, 28% sodium hydroxide solution was added to reach pH 10. The solution was filtered over celite, evaporated and purified by flash chromatography to give 23.6 g (64%) of the title compound as a light brown oil.

MS m/e (%): 297 (M+H+, 100).

g) 2-(3,5-bis-Trifluoromethyl-phenyl)-N-methyl-N-[6-(4-methyl-piperazin-1-yl)-4-o-tolyl-pyridin-3-yl]-isobutyramide A solution of 20 g (67.5 mmol) methyl-[6-(4-methyl-piperazin-1-yl)-4-o-tolyl-pyridin-3-yl]amine and 17.5 ml (101 mmol) N-ethyldiisopropylamine in 200 ml dichloromethane was cooled in an ice bath and a solution of 24 g (75 mmol) 2-(3,5-bis-trifluoromethyl-phenyl)-2-methyl-propionyl chloride in 50 ml dichloromethane was added dropwise. The reaction mixture was warmed to 35–40° C. for 3 h, cooled to room temperature again and was stirred with 250 ml saturated sodium bicarbonate solution. The organic layer was separated and the aqueous phase was extracted with dichloromethane. The combined organic layers were dried (magnesium sulfate) and evaporated. The residue was purified by flash chromatography to give 31.6 g (81%) of the title compound as white crystals. M.p. 155–157° C.

MS m/e (%): 579 (M+H+, 100).

h) 2-(3,5-bis-Trifluoromethyl-phenyl)-N-methyl-N-[6-(4-methyl-piperazin-1-yl)-4-o-tolyl-pyridin-3-yl]-isobutyramide Hydrochloride (1:2)

To a solution of 31.6 g (54.6 mmol) 2-(3,5-bis-trifluoromethyl-phenyl)-N-methyl-N-[6-(4-methyl-piperazin-1-yl)-4-o-tolyl-pyridin-3-yl]-isobutyramide in 250 ml diethyl ether were added under ice cooling 60 ml 3 N hydrochloric acid solution in diethyl ether. After stirring for 15 min at 0° C., the suspension was evaporated to dryness, re-suspended in 100 ml diethyl ether, filtered and dried in vacuo to give 34.8 g (98%) of the title compound as white crystals. M.p. 235–238° C.

MS m/e (%): 579 (M+H+, 100).

EXAMPLE 15

2-(3,5-bis-Trifluoromethyl-phenyl)-N-[4-(2-chlorophenyl)-6-(4-methyl-piperazin-1-yl)-pyridin-3-yl]-N-methyl-isobutyramide Hydrochloride (1:2)

The title compound was obtained as white crystals in comparable yields according to the procedures described above for the preparation of Example 14 using o-chlorophenylboronic acid instead of o-tolylboronic acid in step d).

MS m/e (%): 599 (M+H+, 100), 601 (M+H+, 43).

EXAMPLE 16

2-(3,5-bis-Trifluoromethyl-phenyl)-N-[4-(4-fluoro-2-methyl-phenyl)-6-(4-methyl-piperazin-1-yl)-pyridin-3-yl]-N-methyl-isobutyramide Hydrochloride (1:2)

The title compound was obtained as white crystals in comparable yields according to the procedures described above for the preparation of Example 14 using 4-fluoro-2-methylphenylboronic acid instead of o-tolylboronic acid in step d).

MS m/e (%): 597 (M+H+, 100).

EXAMPLE 17

2-(3,5-bis-Trifluoromethyl-phenyl)-N-[4-(2-chlorophenyl)-pyridin-3-yl]-N-methyl-isobutyramide Hydrochloride (1:1)

a) 2,2-Dimethyl-N-(4-iodo-pyridin-3-yl)-acetamide

A solution of 91 g (510 mmol) N-3-pyridylpivalamide and 230 ml (1.53 mol) N,N,N',N'-tetramethylethylenediamine under argon in 2000 ml tetrahydrofuran was cooled in a dry ice bath to −78° C. Within 1 h, 153 ml (1.53 mmol) of a 10 N n-butyllithium solution in hexane were added dropwise. The reaction mixture was stirred at 0° C. for additional 2 h. After cooling again to −78° C., 380 g (1.5 mol) iodine dissolved in 300 ml tetrahydrofuran were added dropwise during 1.5 h. The dry ice bath was removed and the reaction mixture was allowed to warm up to room temperature overnight. Stirring was continued and 1000 ml water and 1000 ml saturated sodium thiosulfate pentahydrate solution were added. The aqueous layer was separated and extracted twice with 800 ml ethyl acetate. The combined organic layers were dried (magnesium sulfate) and evaporated. Chromatographical filtration gave 75 g (48%) of the title compound as brown crystals.

MS m/e (%): 305 (M+H+, 100).

b) N-[4-(2-Chloro-phenyl)-pyridin-3-yl]-2,2-dimethyl-propionamide

A mixture of 35 g (115 mmol) 2,2-dimethyl-N-(4-iodo-pyridin-3-yl)-acetamide, 400 ml toluene, 120 ml 2 N sodium carbonate solution, 4.0 g (3.5 mmol) tetrakis (triphenylphosphine)palladium(0) and 20.0 g (128 mmol) o-chlorophenylboronic acid was heated under argon at 80° C. for 12 h. After cooling to room temperature, the aqueous phase was separated and washed twice with toluene. The combined organic layers were washed with 50 ml brine, dried (magnesium sulfate) and evaporated. The residue was purified by flash chromatography to yield 21.6 g (65%) of the title compound as white crystals.

MS m/e (%): 289 (M+H+, 100), 291 (M+H+, 40).

c) 4-(2-Chloro-phenyl)-pyridin-3-ylamine

A suspension of 22.2 g (77 mmol) N-[4-(2-chloro-phenyl)-pyridin-3-yl]-2,2-dimethyl-propionamide in 730 ml 3 N hydrochloric acid solution was heated to 90–95° C. overnight. The reaction mixture was cooled to room temperature, washed with three 130 ml portions diethyl ether and 500 ml ethyl acetate were added. The aqueous phase was adjusted to pH 7–8 by addition of 28% sodium hydroxide solution under ice cooling. The organic phase was separated and the product was extracted with three 200 ml portions of ethyl acetate. The combined organic layers were dried (magnesium sulfate) and evaporated to give 14.9 g (95%) of the title compound as white crystals.

MS m/e (%): 205 (M+H$^+$, 100), 207 (M+H$^+$, 39).

d) [4-(2-Chloro-phenyl)-pyridin-3-yl]-methyl-amine

A solution of 14.9 g (72.8 mmol) 4-(2-chloro-phenyl)-pyridin-3-ylamine in 80 ml trimethyl orthoformate and 5 drops trifluoroacetic acid was heated for 2.5 h at 130° C. The reaction mixture was evaporated and dried in vacuo for 30 min. The residual oil was dissolved in 130 ml tetrahydrofuran and 220 ml (220 mmol) of 1 M borane-tetrahydrofuran complex were added dropwise under ice cooling. After stirring overnight at room temperature, the reaction mixture was evaporated, cooled to 0° C. and 130 ml 5 N hydrochloric acid solution in ethanol were added carefully. The solution was refluxed for 1 h, cooled to room temperature again and crushed ice was added. The aqueous phase was washed with three 100 ml portions diethyl ether and the organic layers were extracted with 100 ml 1 N hydrochloric acid solution. The combined aqueous layers were adjusted to pH 8–9 by addition of concentrated sodium hydroxide solution and were extracted with three 500 ml portions ethyl acetate. The combined organic extracts were dried (magnesium sulfate), evaporated and the solid residue was recrystallized from hexane/ethyl acetate to give 12.3 g (77%) of the title compound as white crystals.

MS m/e (%): 219 (M+H$^+$, 100), 221 (M+H$^+$, 42).

e) 2-(3,5-bis-Trifluoromethyl-phenyl)-N-[4-(2-chloro-phenyl)-pyridin-3-yl]-N-methyl-isobutyramide A solution of 12.2 g (55.8 mmol) [4-(2-chloro-phenyl)-pyridin-3-yl]-methyl-amine and 15.3 ml (89 mmol) N-ethyldiisopropylamine in 130 ml dichloromethane was cooled in an ice bath and a solution of 19 g (59.6 mmol) 2-(3,5-bis-trifluoromethyl-phenyl)-2-methyl-propionyl chloride in 30 ml dichloromethane was added dropwise. The reaction mixture was warmed to 35–40° C. for 20 h, cooled to room temperature again and was stirred with 250 ml saturated sodium bicarbonate solution. The organic layer was separated and the aqueous phase was extracted with dichloromethane. The combined organic layers were dried (magnesium sulfate) and evaporated. The residue was purified by flash chromatography to give 24.7 g (88%) of the title compound as white crystals.

MS m/e (%): 501 (M+H$^+$, 100), 503 (M+H$^+$, 36).

f) 2-(3,5-bis-Trifluoromethyl-phenyl)-N-[4-(2-chloro-phenyl)-pyridin-3-yl]-N-methyl-isobutyramide Hydrochloride (1:1)

To a solution of 24.7 g (54.6 mmol) 2-(3,5-bis-trifluoromethyl-phenyl)-N-[4-(2-chloro-phenyl)-pyridin-3-yl]-N-methyl-isobutyramide in 100 ml diethyl ether were added under ice cooling 60 ml 3 N hydrochloric acid solution in diethyl ether. After stirring for 20 min at 0° C., the suspension was evaporated to dryness, re-suspended in 100 ml diethyl ether, filtered and dried in vacuo to give 26.3 g (99%) of the title compound as white crystals. M.p. 186–188° C.

MS m/e (%): 501 (M+H$^+$, 100), 503 (M+H$^+$, 36).

EXAMPLE 18

2-(3,5-bis-Trifluoromethyl-phenyl)-N-methyl-N-(4-o-tolyl-pyridin-3-yl)-isobutyramide Hydrochloride (1:1)

The title compound was obtained as white crystals in comparable yields according to the procedures described above for the preparation of example 17 using o-tolylboronic acid instead of o-chlorophenylboronic acid in step b).

MS m/e (%): 480 (M$^+$, 5), 255 (25), 225 (100).

EXAMPLE 19

2-(3,5-bis-Trifluoromethyl-phenyl)-N-(4-o-tolyl-pyridin-3-yl)-isobutyramide

The title compound was obtained as a brown oil in comparable yields according to the procedures described above for the preparation of Example 17 using o-tolylboronic acid instead of o-chlorophenylboronic acid in step b). Step d) was skipped and no hydrochloride salt was prepared.

MS m/e (%): 467 (M+H$^+$, 100).

EXAMPLE 20

2-(3,5-bis-Trifluoromethyl-phenyl)-N-methyl-N-(4-tolyl-pyridin-3-yl)-acetamide Hydrochloride (1:1)

The title compound was obtained in comparable yields according to the procedures described above for the preparation of Example 17 using o-tolylboronic acid instead of o-chlorophenylboronic acid in step b). Step e) was performed as follows:

To a solution of 511 mg (1.88 mmol) 3,5-bis(trifluoromethyl)phenylacetic acid in 8 ml tetrahydrofuran at 0° C. were added 305 mg (1.88 mmol) 1,1'-carbonyldiimidazole in one portion. The reaction mixture was stirred for 2 h at room temperature and 310 mg (1.56 mmol) methyl-(4-o-tolyl-pyridin-3-yl)-amine were added. Stirring was continued at 55° C. overnight. The reaction mixture was evaporated and the residue was purified by flash chromatography. The hydrochloride salt formation was performed as described in f) and gave 290 mg (38%) of the title compound as yellow crystals.

MS m/e (%): 453 (M+H$^+$, 100).

EXAMPLE 21

2-(3,5-bis-Trifluoromethyl-phenyl)-N-methyl-N-(4-o-tolyl-pyridin-3-yl)-propionamide Hydrochloride (1:1)

The title compound was obtained as white crystals in comparable yields according to the procedures described above for the preparation of Example 17 using o-tolylboronic acid instead of o-chlorophenylboronic acid in step b) and using 2-(3,5-bis-trifluoromethyl-phenyl)-propionyl chloride instead of 2-(3,5-bis-trifluoromethyl-phenyl)-2-methyl-propionyl chloride in step e).

MS m/e (%): 466 (M$^+$, 5), 241 (12), 225 (100).

EXAMPLE 22

1-(3,5-bis-Trifluoromethyl-phenyl)-cyclopropanecarboxylic Acid [(4-(2-Chloro-phenyl)-pyridin-3-yl]-methyl-amide Hydrochloride a) 1-(3,5-bis-Trifluoromethyl-phenyl)-cyclopropanecarboxylic Acid [4-(2-chlorophenyl)-pyridin-3-yl]-methyl-amide To a solution of 88 mg (0.4 mmole) 4-(2-chloro-phenyl)-pyridin-3-yl]-methyl-amine and 0.11 ml (0.6 mmole) N-ethyldiisopropylamine in 4 ml dichloromethane was added a solution of 174 mg (0.3 mmole) 1-(3,5-bistrifluoromethyl-phenyl)-cyclopropanecarboxylic acid chloride in 1 ml dichloromethane. After refluxing for 72 h the reaction mixture was washed twice with water, dried (magnesium sulfate) and evaporated. Chromatography of the residue (silicagel, ethyl acetate:hexane 7:3) afforded 132 mg (66%) of the title compound as a yellow oil.

MS m/e (%): 499 (M+H, 100).

b) 1-(3,5-bis-Trifluoromethyl-phenyl)-cyclopropanecarboxylic Acid [4-(2-chloro-phenyl)-pyridin-3-yl]-methyl-amide Hydrochloride To 125 mg 1-(3,5-bis-trifluoromethyl-phenyl)-cyclopropanecarboxylic acid [4-(2-chloro-phenyl)-pyridin-3-yl]-methyl-amide were added 1.5 ml 3 N hydrochloric acid in methanol. After evaporating the solution 3 ml ether were added and the suspension was stirred for 1 h at 0° C. Filtration afforded 100 mg (75%) of the title compound as white crystals. Mp.: 194–196° C.

EXAMPLE 23

2-(3,5-bis-Trifluoromethyl-phenyl)-N-methyl-N-(6-morpholin-4-yl-4-o-tolyl-pyridin-3-yl)-isobutyramide Hydrochloride (1:1.45)

a) 4-(5-Nitro-2-pyridyl)-morpholine

To a solution of 20 g (126 mmol) of 2-chloro-5-nitropyridine in 150 ml tetrahydrofuran were added dropwise 27 ml (315 mmol) morpholine within 10 min. The reaction mixture was refluxed for additional 2 h. After cooling to room temperature, the solvent was removed in vacuo and the residue was re-dissolved in 200 ml ethyl acetate. The organic phase was washed with 200 ml 1 N sodium bicarbonate solution, dried (magnesium sulfate) and evaporated to give 27.3 g (quantitative) of the title compound as a yellow solid. M.p. 142–143° C.

b) 2.2-Dimethyl-N-(6-morpholin-4-yl-pyridin-3-yl)-propionamide

To a solution of 27.3 g (126 mmol) of 4-(5-nitro-2-pyridyl)-morpholine in 600 ml methanol were added 2.5 g of 10% of palladium on activated charcoal. The reaction mixture was hydrogenated (room temperature to ca. 45° C., 1 bar) until the theoretical amount of hydrogen was taken up (about 3 h). The catalyst was filtered off and was washed twice with 100 ml portions of methanol. The filtrate was evaporated in vacuo to give 22.6 g of a purple oil which consisted to ca. 95% of the desired aniline derivative according to analysis by thin layer chromatography.

This crude product was dissolved in a mixture of 240 ml tetrahydrofuran and 60 ml diethyl ether. After cooling to 0° C., 26 ml (189 mmol) of triethylamine were added in one portion. Stirring was continued while 23 g (189 mmol) of pivaloyl chloride were added dropwise within a period of 10 min. The ice bath was removed and the reaction mixture was stirred for 1 h at room temperature. Then, the solvent was removed in vacuo and the residue was suspended in 200 ml 1 N sodium bicarbonate solution. The product was extracted three times with 200 ml portions of dichloromethane, dried (sodium sulfate) and evaporated. Recrystallization of the solid residue from ethyl acetate/hexane 1:8 gave 28.6 g (86%) of the title compound as white crystals.

MS m/e (%): 264 (M+H$^+$, 100).

c) N-(4-Iodo-6-morpholin-4-yl-pyridin-3-yl)-2,2-dimethyl-propionamide

A solution of 28.4 g (108 mmol) 2,2-dimethyl-N-(6-morpholin-4-yl-pyridin-3-yl)-propionamide and 49 ml (324 mmol) N,N,N',N'-tetramethylethylenediamine under argon in 600 ml tetrahydrofuran was cooled in a dry ice bath to −78° C. Within 1 h, 202 ml (324 mmol) of a 1.6 N n-butyllithium solution in hexane were added dropwise. The reaction mixture was allowed to warm up to −35° C. overnight. After cooling again to −78° C., 37 g (146 mmol) iodine dissolved in 60 ml tetrahydrofuran were added dropwise during 15 min. The dry ice bath was replaced by an ice bath and a solution of 90 g (363 mmol) sodium thiosulfate pentahydrate in 250 ml water were added within 10 min when the temperature of the reaction mixture had reached 0° C. Then, 1000 ml diethyl ether were added and the organic layer was separated. The aqueous layer was extracted twice with 500 ml dichloromethane and the combined organic layers were dried (magnesium sulfate) and evaporated. Flash chromatography gave 15.6 g (37%) of the title compound as a light brown oil which crystallized upon standing at room temperature.

MS m/e (%): 389 (M$^+$, 71), 358 (25), 304 (43), 57 (100).

d) 2,2-Dimethyl-N-(6-morpholin-4-yl-4-o-tolyl-pyridin-3-yl)-propionamide

A mixture of 3.50 g (9.0 mmol) N-(4-iodo-6-morpholin-4-yl-pyridin-3-yl)-2,2-dimethyl-propionamide, 35 ml toluene, 18 ml 2 N sodium carbonate solution, 312 mg (0.27 mmol) tetrakis(triphenylphosphine)palladium(0) and 1.34 g (9.9 mmol) o-tolylboronic acid was heated under argon at 80° C. for 12 h. After cooling to room temperature, the aqueous phase was separated and washed twice with ethyl acetate. The combined organic layers were washed with 50 ml brine, dried (sodium sulfate) and evaporated. Purification by flash-chromatography gave 3.23 g (quantitative) of the title compound as a white foam.

MS m/e (%): 354 (M+H$^+$, 100).

e) 6-Morpholin-4-yl-4-o-tolyl-pyridin-3-ylamine

A suspension of 2.93 g (8.28 mmol) 2,2-dimethyl-N-(6-morpholin-4-yl-4-o-tolyl-pyridin-3-yl)-propionamide in 80 ml 3 N hydrochloric acid solution and 5 ml 1-propanol was heated to 90–95° C. overnight. The reaction mixture was cooled to room temperature, washed with three 20 ml portions diethyl ether and filtered over celite. The filtrate was diluted with 20 ml water and was adjusted to pH 7–8 by addition of 28% sodium hydroxide solution under ice cooling. The product was extracted with four 100 ml portions of dichloromethane. The combined organic layers were washed with 50 ml brine, dried (magnesium sulfate) and evaporated to give 2.31 g (quantitative) of the title compound as a white foam.

MS m/e (%): 269 (M$^+$, 100).

f) Methyl-(6-morpholin-4-yl-4-o-tolyl-pyridin-3-yl)-amine

A solution of 2.24 g (8.3 mmol) 6-morpholin-4-yl-4-o-tolyl-pyridin-3-ylamine in 17 ml trimethyl orthoformate and 3 drops trifluoroacetic acid was heated for 2 h at 130° C. The reaction mixture was evaporated and dried in vacuo for 30 min. The residual oil was dissolved in 5 ml tetrahydrofuran and was added dropwise under ice cooling to 630 mg (16.6 mmol) lithium aluminum hydride in 20 ml tetrahydrofuran. The reaction mixture was stirred for 1 h at room temperature, cooled to 0° C. again and acidified (pH 1–2) by addition of 28% hydrochloric acid solution. After stirring for 5 min, 28% sodium hydroxide solution was added to reach pH 10. The solution was filtered over celite, evaporated and purified by flash chromatography to give 1.56 g (66%) of the title compound as a white foam.

MS m/e (%): 283 (M$^+$, 100).

g) 2-(3,5-bis-Trifluoromethyl-phenyl)-N-methyl-N-(6-morpholin-4-yl-4-o-tolyl-pyridin-3-yl)-isobutyramide A solution of 1.46 g (5.15 mmol) methyl-(6-morpholin-4-yl-4-o-tolyl-pyridin-3-yl)-amine and 1.32 ml (7.73 mmol) N-ethyldiisopropylamine in 15 ml dichloromethane was cooled in an ice bath and 1.8 g (5.67 mmol) 2-(3,5-bis-trifluoromethyl-phenyl)-2-methyl-propionyl chloride were added dropwise. The reaction mixture was warmed to 35–40° C. for 3 h, cooled to room temperature again and was stirred with 25 ml saturated sodium bicarbonate solution. The organic layer was separated and the aqueous phase was extracted with dichloromethane. The combined organic layers were dried (magnesium sulfate) and evaporated. The residue was purified by flash chromatography to give 2.9 g (quantitative) of the title compound as white crystals. M.p. 131–132° C.

h) 2-(3,5-bis-Trifluoromethyl-phenyl)-N-methyl-N-(6-morpholin-4-yl-4-o-tolyl-pyridin-3-yl)-isobutyramide Hydrochloride (1:1.45)

To a solution of 2.9 g (5.13 mmol) 2-(3,5-bis-trifluoromethyl-phenyl)-N-methyl-N-(6-morpholin-4-yl-4-o-tolyl-pyridin-3-yl)-isobutyramide in 50 ml diethyl ether were added under ice cooling 2.8 ml 3 N hydrochloric acid solution in diethyl ether. After stirring for 15 min at 0° C., the suspension was evaporated to dryness, re-suspended in 100 ml diethyl ether, filtered and dried in vacuo to give 2.82 g (89%) of the title compound as white crystals.

MS m/e (%): 566 (M+H$^+$, 100), 588 (M+Na$^+$, 11).

EXAMPLE 24

2-(3,5-bis-Trifluoromethyl-phenyl)-N-[4-(2-chlorophenyl)-6-morpholin-4-yl-pyridin-3-yl]-N-methyl-isobutyramide Hydrochloride (1:1)

The title compound was obtained as white crystals in comparable yields according to the procedures described above for the preparation of Example 23 using 2-chlorophenylboronic acid instead of o-tolylboronic acid in step d).

MS m/e (%): 586 (M+H$^+$, 100).

EXAMPLE 25

2-(3,5-bis-Trifluoromethyl-phenyl)-N-methyl-N-{6-[methyl-(2-morpholin-4-yl-ethyl)-amino]-4-o-tolyl-pyridin-3-yl}-isobutyramide The title compound was obtained as light brown oil in comparable yields according to the procedures described above for the preparation of Example 23 using 4-[2-(methylamino)ethyl]-morpholine instead of morpholine in step a). No hydrochloride salt was prepared.

MS m/e (%): 623 (M+H$^+$, 100).

EXAMPLE 26

2-(3,5-bis-Trifluoromethyl-phenyl)-N-methyl-N-[6-(4pyrimidin-2-yl-piperazin-1-yl)-4-o-tolyl-pyridin-3-yl]-isobutyramide The title compound was obtained as colourless oil in comparable yields according to the procedures described above for the preparation of Example 23 using 2-(1-piperazinyl)pyrimidine instead of morpholine in step a). No hydrochloride salt was prepared.

MS m/e (%): 643 (M+H$^+$, 100).

EXAMPLE 27

2-(3,5-bis-Trifluoromethyl-phenyl)-N-(6-morpholin-4-yl-4-o-tolyl-pyridin-3-yl)-isobutyramide The title compound was obtained as white powder in comparable yields according to the procedures described above for the preparation of Example 23 but step f) was skipped and no hydrochloride salt was prepared.

MS m/e (%): 552 (M+H$^+$, 100).

EXAMPLE 28

2-(3,5-bis-Trifluoromethyl-phenyl)-N-[4'-(2-chlorophenyl)-3,4,5,6-tetrahydro-2H-[1,2']bipyridinyl-5'-yl]-N-methyl-isobutyramide Hydrochloride (1:1)

The title compound was obtained as a white powder in comparable yields according to the procedures described above for the preparation of Example 23 using piperidine instead of morpholine in step a) and using 2-chlorophenylboronic acid instead of o-tolylboronic acid in step d).

MS m/e (%): 583 (M$^+$, 20), 296 (78), 255 (100).

EXAMPLE 29

2-(3,5-bis-Trifluoromethyl-phenyl)-N-(6-dimethylamino-4-o-tolyl-pyridin-3-yl)-N-methyl-isobutyramide The title compound was obtained as white solid in comparable yields according to the procedures described above for the preparation of Example 23 using dimethylamine hydrochloride instead of morpholine in step a). No hydrochloride salt was prepared. M.p. 174–175° C.

MS m/e (%): 524 (M+H$^+$, 100).

EXAMPLE 30

2-(3,5-bis-Trifluoromethyl-phenyl)-N-[4-(2-chlorophenyl)-6-dimethylamino-pyridin-3-yl]-isobutyramide The title compound was obtained as white solid in comparable yields according to the procedures described above for the preparation of Example 23 using dimethylamine hydrochloride instead of morpholine in step a) and using 2-chlorophenylboronic acid instead of o-tolylboronic acid in step d). No hydrochloride salt was prepared. M.p. 162–163° C.

MS m/e (%): 544 (M+H$^+$, 100).

EXAMPLE 31

2-(3,5-bis-Trifluoromethyl-phenyl)-N-methyl-N-(6-piperazin-1-yl-4-o-tolyl-pyridin-3-yl)-isobutyramide To a solution of 100 mg (0.173 mmol) 2-(3,5-bis-trifluoromethyl-phenyl)-N-methyl-N-[6-(4-methyl-piperazin-1-yl)-4-o-tolyl-pyridin-3-yl]-isobutyramide (example 14 g) and 7 mg (0.035 mmol) 1,8-bis (dimethylamino)naphthalene in 1 ml 1,2-dichloroethane at 0° C. were added 26 mg (0.181 mmol) 1-chloroethyl chloroformate. After heating the reaction mixture for 1 h at 80° C. the solvent was removed in vacuo and the intermediate was purified by flash chromatography, re-dissolved in 1 ml methanol and refluxed for 3 h. Flash chromatography gave 56 mg (57%) of the title compound as white foam.

MS m/e (%): 565 (M+H$^+$, 100).

EXAMPLE 32

2-(3,5-bis-Trifluoromethyl-phenyl)-N-(4-hydroxy-4'-o-tolyl-3,4,5,6-tetrahydro-2H-[1,2']bipyridinyl-5'-yl)-N-methyl-isobutyramide The title compound was obtained as white foam in comparable yields according to the procedures described above for the preparation of Example 23 using 4-hydroxypiperidine instead of morpholine in step a). No hydrochloride salt was prepared.

MS m/e (%): 580 (M+H$^+$, 100).

EXAMPLE 33

2-(3,5-bis-Trifluoromethyl-phenyl)-N-{6-[(2-hydroxy-ethyl)-methyl-amino]-4-o-tolyl-pyridin-3-yl}-N-methyl-isobutyramide The title compound was obtained as white foam in comparable yields according to the procedures described above for the preparation of Example 23 using N-methylethanolamine instead of morpholine in step a). No hydrochloride salt was prepared.

MS m/e (%): 554 (M+H$^+$, 100).

EXAMPLE 34

(R)-2-(3,5-bis-Trifluoromethyl-phenyl)-N-[6-(3-hydroxy-pyrrolidin-1-yl)-4-o-tolyl-pyridin-3-yl]-N-methyl-isobutyramide The title compound was obtained as white foam in comparable yields according to the procedures described above for the preparation of Example 23 using (R)-3-hydroxypyrrolidine instead of morpholine in step a). No hydrochloride salt was prepared.

MS m/e (%): 566 (M+H$^+$, 100).

EXAMPLE 35

2-(3,5-bis-Trifluoromethyl-phenyl)-N-methyl-N-(6-morpholin-4-yl-4-o-tolyl-pyridin-3-yl)-acetamide To a solution of 300 mg (1.1 mmol) 3,5-bis(trifluoromethyl)-phenylacetic acid in 7 ml N,N-dimethylformamide were added 185 mg (1.14 mmol) 1,1'-carbonyl-diimidazole and the solution was stirred for 30 min at room temperature. After addition of 283 mg (1 mmol) of methyl-(6-morpholin-4-yl-4-tolyl-pyridin-3-yl)-amine (as described in step f) for the preparation of Example 23), the reaction mixture was heated over night at 90° C. After cooling to room temperature, the solvent was removed in vacuo and the residue was re-dissolved in 30 ml ethyl acetate. The organic phase was washed with water (2×30 ml), brine, dried (magnesium sulfate) and evaporated. Flash chromatography gave 506 mg (94%) of the title compound as a light brown foam.

MS m/e (%): 538 (M+H$^+$, 100).

EXAMPLE 36

2-(3,5-Dimethoxy-phenyl)-N-methyl-N-(6-morpholin-4-yl-4-o-tolyl-pyridin-3-yl)-acetamide To a solution of 226 mg (1.15 mmol) 3,5-dimethoxyphenylacetic acid in 7 ml N,N-dimethylformamide were added 244 mg (1.5 mmol) 1,1'-carbonyl-diimidazole and the solution was stirred for 30 min at room temperature. After addition of 283 mg (1 mmol) of methyl-(6-morpholin-4-yl-4-tolyl-pyridin-3-yl)-amine (as described in step f) for the preparation of Example 23), the reaction mixture was heated at 70° C. for 7 h. After cooling to room temperature, the solvent was removed in vacuo and the residue was re-dissolved in 30 ml ethyl acetate. The organic phase was washed with water (2×30 ml), brine, dried (magnesium sulfate) and evaporated. Flash chromatography gave 347 mg (75%) of the title compound as a white foam.

MS m/e (%): 462 (M+H$^+$, 100).

EXAMPLE 37

2-(3-Fluoro-5-trifluoromethyl-phenyl)-N-methyl-N-(6-morpholin-4-yl-4-o-tolyl-pyridin-3-yl)-acetamide To a solution of 266 mg (1.2 mmol) 3-fluoro-5-trifluoromethyl-phenylacetic acid in 7 ml N,N-dimethylformamide were added 195 mg (1.2 mmol) 1,1'-carbonyl-diimidazole and the solution was stirred for 30 min at room temperature. After addition of 283 mg (1 mmol) of methyl-(6-morpholin-4-yl-4-tolyl-pyridin-3-yl)-amine (as described in step f) for the preparation of Example 23), the reaction mixture was heated at 90° C. for 6 h. After cooling to room temperature, the solvent was removed in vacuo and the residue was re-dissolved in 30 ml ethyl acetate. The organic phase was washed with water (2×30 ml), brine, dried (magnesium sulfate) and evaporated. Flash chromatography gave 432 mg (88%) of the title compound as a light yellow foam.

MS m/e (%): 488 (M+H$^+$, 100).

EXAMPLE 38

[2-(3,5-bis-Trifluoromethyl-phenyl)-2-methyl-propyl]-[4-(4-fluoro-2-methyl-phenyl)-6-(4-methyl-piperazin-1-yl)-pyridin-3-yl]-methyl-amine Hydrochloride (1:3)

To a mixture of 400 mg (0.60 mmol) 2-(3,5-bis-trifluoromethyl-phenyl)-N-[4-(4-fluoro-2-methyl-phenyl)-6-(4-methyl-piperazin-1-yl)-pyridin-3-yl]-N-methyl-isobutyramide hydrochloride (1:2) (example 16) and 50 ml dichloromethane were added 20 ml 1 N sodium hydroxide solution. After shaking for 1 min, the organic phase was separated and evaporated to dryness. The residue was re-dissolved in 5 ml tetrahydrofuran and 4 ml of a 1 M borane tetrahydrofuran complex solution were added. After heating at 60° C. for 3 days, 10 ml 3 N hydrochloric acid solution in diethyl ether were added and the reaction mixture was refluxed for 4 h. The reaction mixture was cooled to room temperature, washed with 10 ml 1 N sodium hydroxide solution, dried (sodium sulfate) and purified by flash chromatography to yield 279 mg of a pale yellow oil which was transformed into the hydrochloride salt as described in step h) for the preparation of Example 23 to give 153 mg (37%) of the title compound as pale yellow crystals.

MS m/e (%): 583 (M+H$^+$, 100).

EXAMPLE 39

(3,5-bis-Trifluoromethyl-benzyl)-methyl-(4-o-tolyl-pyridin-3-ylmethyl)-amine

Lithium aluminum hydride (107 mg, 2.82 mmol, 3 eq) was suspended in 7 ml tetrahydrofuran at 0° C. under argon. N-(3,5-bis-trifluoromethyl-benzyl)-N-methyl-4-o-tolyl-nicotinamide (example 1, 425 mg, 0.94 mmol), dissolved in 4 ml tetrahydrofuran, was slowly added at ~5° C. The mixture was stirred 5 min at room temperature and 1 hr under reflux.

Ethyl acetate (1 ml) was added, then the mixture was cooled to room temperature and aqueous saturated sodium sulfate solution was added dropwise. The mixture was dried (sodium sulfate), filtered, concentrated and purified by flash chromatography to give 93 mg (23%) of the title compound as a colourless oil.

MS m/e (%): 439 (M+H$^+$, 100).

EXAMPLE 40

3-(3,5-bis-Trifluoromethyl-benzyloxymethyl)-4-o-tolyl-pyridine a) (4-o-Tolyl-pyridin-3-yl)-methanol Lithium aluminum hydride (439 mg, 11.6 mmol, 1 eq) was suspended in 23 ml tetrahydrofuran at 0° C. under argon. 4-o-Tolyl-nicotinic acid methyl ester (2.63 g, 11.6 mmol), dissolved in 12 ml tetrahydrofuran, was slowly added at 5° C. The mixture was stirred 5 min at room temperature and 1 h under reflux.

Ethyl acetate (1 ml) was added, then the mixture was cooled to room temperature and aqueous saturated sodium sulfate solution was added dropwise. The mixture was dried (sodium sulfate), filtered, concentrated and purified by flash chromatography to give 0.77 g (33%) of the title compound as a pale yellow liquid.

Starting material (1.60 g, 61%) was recovered.

MS m/e (%): 199 ($M^+$, 3), 180 (100).

b) 3-(3,5-Trifluoromethyl-benzyloxymethyl)-4-o-tolyl-pyridine

Sodium hydride (89.1 mg, 2.04 mmol, 1.1 eq) was washed twice with n-hexane under argon and suspended in 1 ml dimethyl formamide. (4-o-Tolyl-pyridin-3-yl)-methanol (370 mg, 1.86 mmol), dissolved in 4 ml dimethyl formamide, was added dropwise and the mixture was stirred 1 h at room temperature. 3,5-Bis(trifluoromethyl)benzyl bromide (627 mg, 2.04 mmol, 1 eq), dissolved in 2 ml dimethyl formamide, was added and the mixture was stirred 2.5 h at room temperature.

The mixture was concentrated and the residue was partitioned between water and dichloromethane. The organic extract was washed with brine, dried (sodium sulfate), filtered, concentrated and purified by flash chromatography to give 196 mg (25%) of the title compound as yellow oil.

Starting material (0.24 g, 65%) was recovered.

MS m/e (%): 426 ($M+H^+$, 100).

EXAMPLE 41

N-(3,5-bis-Trifluoromethyl-benzyl)-N-methyl-6-(4-methyl-piperazin-1-yl)-4-naphthalen-1-yl-nicotinamide Hydrochloride (1:2)

The title compound was obtained as a white solid in comparable yields according to the procedures described above for the preparation of N-(3,5-bis-trifluoromethyl-benzyl)-N-methyl-6-(4-methyl-piperazin-1-yl)-4-o-tolyl-nicotinamide (Example 12) using 1-naphthylboronic acid instead of o-tolylboronic acid in step d) and using N-methyl-6-(4-methyl-piperazin-1-yl)-4-naphthalen-1-yl-nicotinamide instead of N-methyl-6-(4-methyl-piperazin-1-yl)-4-o-tolyl-nicotinamide in step e).

MS m/e (%): 587 ($M+H^+$, 100).

EXAMPLE 42

(3,5-bis-Trifluoromethyl-benzyl)-[4-(2-chloro-phenyl)-6-(4-methyl-piperazin-1-yl)-pyridin-3-ylmethyl]-methyl-amine; Hydrochloride (1:3)

To a solution of 260 mg (0.455 mmol) N-(3,5-bis-trifluoromethyl-benzyl)-4-(2-chloro-phenyl)-N-methyl-6-(4-methyl-piperazin-1-yl)-nicotinamide (Example 13) in 6.3 ml dry tetrahydrofuran were added 2.73 ml (2.73 mmol) 1M borane solution in tetrahydrofuran. The mixture was heated at reflux for 16 h. After cooling to room temperature 12.6 ml 3N hydrogen chloride solution in diethyl ether were added, and the mixture was heated at reflux for 40 min. After cooling to room temperature 1N aqueous sodium hydroxide solution was added. Extraction with ethyl acetate, drying with sodium sulfate and concentration were followed by flash chromatography affording 165 mg of a colorless oil. To a solution of the oil in 2 ml diethyl ether were added 3 ml 3N hydrogen chloride solution in diethyl ether. After stirring the mixture for 45 min. a precipitate had formed which was collected by filtration. Drying in vacuo afforded 144 mg (47.5%) of the title compound as a white solid.

MS m/e (%): 557 ($M+H^+$, 100).

EXAMPLE 43

4-{5-[(3,5-bis-Trifluoromethyl-benzyl)-methyl-carbamoyl]-4-o-tolyl-pyridin-2-yl}-piperazine-1-carboxylic Acid tert-Butyl Ester a) 6-Chloro-N-methyl-4-o-tolyl-nicotinamide To a solution of 3.41 g (20.0 mmol) 6-chloro-N-methyl-nicotinamide (Example 12 step a)) in 80 ml tetrahydrofuran 50 ml (50 mmol) of a 1 M solution of o-tolyl magnesium chloride in tetrahydrofuran was added dropwise at 0° C. After completed addition the reaction mixture was allowed to warm to room temperature and stirred for 1.5 h. The mixture was again cooled to 0° C., followed by the dropwise addition of 5.7 ml (100 mmol) acetic acid and a solution of 5.1 g (22 mmol) 2,3-dichloro-5,6-dicyano-1,4-benzoquinone in 18 ml tetrahydrofuran. After completed addition the reaction mixture was allowed to warm to room temperature and stirred for 15 min. Addition of 30 ml 2 N aqueous sodium hydroxide solution was followed by dilution with 1 l ethyl acetate and 200 ml water. The layers were separated and the organic layer was washed with 4250-ml portions of 2 N aqueous sodium hydroxide solution. The combined aqueous layers were extracted with 3 500-ml portions of ethyl acetate. The combined organic extracts were washed with saturated aqueous sodium chloride solution and dried with sodium sulfate. Concentration gave 5.44 g of a brown-red oil. Flash column chromatography afforded 2.15 g (41.3%) of the title compound as a light yellow solid.

MS m/e (%): 260 ($M^+$, 11), M.p. 91–93° C.

b) 4-(5-Methylcarbamoyl-4-o-tolyl-pyridin-2-yl)-piperazine-1-carboxylic Acid tert-Butyl Ester A mixture of 8.31 g (31.9 mmol) 6-chloro-N-methyl-4-o-tolyl-nicotinamide, 6.53 g (35.0 mmol) 1-tert-butoxycarbonyl piperazine, 16.7 ml (95.6 mmol) N-ethyldiisopropylamine and a catalytic amount of 4-(N,N-dimethylamino)-pyridine was heated at reflux over night. After cooling to room temperature the mixture was dissolved in dichloromethane and washed with two portions of 0.1 N aqueous hydrochloric acid solution. Drying with sodium sulfate and concentration gave 10.7 g of the crude product. Flash column chromatography afforded 6.28 g (48.0%) of the title compound as an off-white solid.

MS m/e (%): 411 ($M+H^+$, 100).

c) 4-{5-[(3,5-bis-Trifluoromethyl-benzyl)-methyl-carbamoyl]-4-o-tolyl-pyridin-2-yl}-piperazine-1-carboxylic Acid tert-Butyl Ester The title compound was obtained as a white solid in comparable yield according to the procedure described above for the preparation of N-(3,5-bis-trifluoromethyl-benzyl)-N-methyl-6-(4-methyl-piperazin-1-yl)-4-o-tolyl-nicotinamide (Example 12, step e)) using 4-(5-methylcarbamoyl-4-o-tolyl-pyridin-2-yl)-piperazine-1-carboxylic acid tert-butyl ester instead of N-methyl-6-(4-methyl-piperazin-1-yl)-4-o-tolyl-nicotinamide.

MS m/e (%): 637 ($M+H^+$, 100).

EXAMPLE 44

(4-{5-[(3,5-bis-Trifluoromethyl-benzyl)-methyl-carbamoyl]-4-o-tolyl-pyridin-2-yl}-piperazin-1-yl)-acetic Acid Ethyl Ester The title compound was obtained as a yellow solid in comparable yield for step b) and 3% yield for step c)

according to the procedures described above for the preparation of 4-{5-[(3,5-bis-trifluoromethyl-benzyl)-methyl-carbamoyl]-4-o-tolyl-pyridin-2-yl}-piperazine-1-carboxylic acid tert-butyl ester (Example 43) using 1-(ethoxycarbonylmethyl)-piperazine instead of 1-tert-butoxycarbonyl piperazine in step b) and using[4-(5-methylcarbamoyl-4-o-tolyl-pyridin-2-yl)-piperazin-1-yl]-acetic acid ethyl ester instead of 4-(5-methylcarbamoyl-4-o-tolyl-pyridin-2-yl)-piperazine-1-carboxylic acid tert-butyl ester in step c).

MS m/e (%): 623 (M+H+, 100).

EXAMPLE 45

5'-[(3,5-bis-Trifluoromethyl-benzyl)-methyl-carbamoyl]-4'-o-tolyl-3,4,5,6-tetrahydro-2H-[1,2']bipyridinyl-4-carboxylic Acid Ethyl Ester The title compound was obtained as a white solid in comparable yields according to the procedures described above for the preparation of 4-{5-[(3,5-bis-trifluoromethyl-benzyl)-methyl-carbamoyl]-4-o-tolyl-pyridin-2-yl}-piperazine-1-carboxylic acid tert-butyl ester (Example 43) using ethyl isonipecotate instead of 1-tert-butoxycarbonyl piperazine in step b) and using 5'-methylcarbamoyl-4'-o-tolyl-3,4,5,6-tetrahydro-2H-[1,2']bipyridinyl-4-carboxylic acid ethyl ester instead of 4-(5-methylcarbamoyl-4-o-tolyl-pyridin-2-yl)-piperazine-1-carboxylic acid tert-butyl ester in step c).

MS m/e (%): 608 (M+H+, 100).

EXAMPLE 46

N-(3,5-bis-Trifluoromethyl-benzyl)-N-methyl-6-(4-propyl-piperazin-1-yl)-4-o-tolyl-nicotinamide The title compound was obtained as a light-yellow solid in comparable yields according to the procedures described above for the preparation of 4-{5-[(3,5-bis-trifluoromethyl-benzyl)-methyl-carbamoyl]-4-o-tolyl-pyridin-2-yl}-piperazine-1-carboxylic acid tert-butyl ester (Example 43) using 1-propyl piperazine instead of 1-tert-butoxycarbonyl piperazine in step b) and using N-methyl-6-(4-propyl-piperazin-1-yl)-4-o-tolyl-nicotinamide instead of 4-(5-methylcarbamoyl-4-o-tolyl-pyridin-2-yl)-piperazine-1-carboxylic acid tert-butyl ester in step c).

MS m/e (%): 579 (M+H+, 100).

EXAMPLE 47

(RS)-6-[3-(Acetyl-methyl-amino)-pyrrolidin-1-yl]-N-(3,5-bis-trifluoromethyl-benzyl)-N-methyl-4-o-tolyl-nicotinamide The title compound was obtained as a light-yellow solid in comparable yields according to the procedures described above for the preparation of 4-{5-[(3,5-bis-trifluoromethyl-benzyl)-methyl-carbamoyl]-4-o-tolyl-pyridin-2-yl}-piperazine-1-carboxylic acid tert-butyl ester (Example 43) using (RS)-3-(acetyl-methyl-amino)-pyrrolidine instead of 1-tert-butoxycarbonyl piperazine in step b) and using (RS)-6-[3-(acetyl-methyl-amino)-pyrrolidin-1-yl]-N-methyl-4-o-tolyl-nicotinamide instead of 4-(5-methylcarbamoyl-4-o-tolyl-pyridin-2-yl)-piperazine-1-carboxylic acid tert-butyl ester in step c).

MS m/e (%): 593 (M+H+, 100).

EXAMPLE 48

N-(3,5-bis-Trifluoromethyl-benzyl)-N-methyl-6-[methyl-(2-morpholin-4-yl-ethyl)-amino]-4-o-tolyl-nicotinamide The title compound was obtained as a light-yellow solid in comparable yields according to the procedures described above for the preparation of 4-{5-[(3,5-bis-trifluoromethyl-benzyl)-methyl-carbamoyl]-4-o-tolyl-pyridin-2-yl}-piperazine-1-carboxylic acid tert-butyl ester (Example 43) using methyl-(2-morpholin-4-yl-ethyl)-amine instead of 1-tert-butoxycarbonyl piperazine in step b) and using N-methyl-6-[methyl-(2-morpholin-4-yl-ethyl)-amino]-4-o-tolyl-nicotinamide instead of 4-(5-methylcarbamoyl-4-o-tolyl-pyridin-2-yl)-piperazine-1-carboxylic acid tert-butyl ester in step c).

MS m/e (%): 595 (M+H+, 100).

EXAMPLE 49

N-(3,5-bis-Trifluoromethyl-benzyl)-N-methyl-6-morpholin-4-yl-4-o-tolyl-nicotinamide The title compound was obtained as a white solid in comparable yields according to the procedures described above for the preparation of 4-{5-[(3,5-bis-trifluoromethyl-benzyl)-methyl-carbamoyl]-4-o-tolyl-pyridin-2-yl}-piperazine-1-carboxylic acid tert-butyl ester (Example 43) using morpholine instead of 1-tert-butoxycarbonyl piperazine in step b) and using N-methyl-6-morpholin-4-yl-4-o-tolyl-nicotinamide instead of 4-(5-methylcarbamoyl-4-o-tolyl-pyridin-2-yl)-piperazine-1-carboxylic acid tert-butyl ester in step c).

MS m/e (%): 538 (M+H+, 100).

EXAMPLE 50

N-(3,5-bis-Trifluoromethyl-benzyl)-N-methyl-6-thiomorpholin-4-yl-4-o-tolyl-nicotinamide The title compound was obtained as a white solid in comparable yields according to the procedures described above for the preparation of 4-{5-[(3,5-bis-trifluoromethyl-benzyl)-methyl-carbamoyl]-4-o-tolyl-pyridin-2-yl}-piperazine-1-carboxylic acid tert-butyl ester (Example 43) using thiomorpholine instead of 1-tert-butoxycarbonyl piperazine in step b) and using N-methyl-6-thiomorpholin-4-yl-4-o-tolyl-nicotinamide instead of 4-(5-methylcarbamoyl-4-o-tolyl-pyridin-2-yl)-piperazine-1-carboxylic acid tert-butyl ester in step c).

MS m/e (%): 554 (M+H, 100).

EXAMPLE 51

N-(3,5-bis-Trifluoromethyl-benzyl)-N-methyl-6-(1-oxo-1$\lambda^4$-thiomorpholin-4-yl)-4-o-tolyl-nicotinamide To a solution of 1.24 g (2.24 mmol) N-(3,5-bis-trifluoromethyl-benzyl)-N-methyl-6-thiomorpholin-4-yl-4-o-tolyl-nicotinamide (Example 50) in 25 ml methanol were added 689 mg (1.12 mmol) Oxone® at 0° C. After completed addition the reaction mixture was allowed to warm to room temperature and stirred for 1.5 h. Quenching with 5 ml 40% aqueous sodium hydrogen sulfite solution was followed by addition of 6 ml 1N sodium hydroxide solution to adjust the pH to 7–8. The mixture was diluted with 50 ml water and extracted with 3 150-ml portions of dichloromethane. The combined extracts were dried with sodium sulfate and concentrated to give 1.20 g of crude product. Flash chromatography afforded 1.02 g (79.9%) of the title compound as a white solid.

MS m/e (%): 570 (M+H+, 100).

EXAMPLE 52

N-(3,5-bis-Trifluoromethyl-benzyl)-6-(1,1-dioxo-1$\lambda^6$-thiomorpholin-4-yl)-N-methyl-4-o-tolyl-nicotinamide The title compound was obtained as a white solid in comparable yield according to the procedure described above for the preparation of N-(3,5-bis-trifluoromethyl-benzyl)-N-methyl-6-(1-oxo-1l-4-thiomorpholin-4-yl)-4-o-tolyl-nicotinamide (Example 51) using N-(3,5-bis-trifluoromethyl-benzyl)-N-methyl-6-(1-oxo-1l-4-thiomorpholin-4-yl)-4-o-tolyl-nicotinamide instead of N-(3,5-bis-trifluoromethyl-benzyl)-N-methyl-6-thiomorpholin-4-yl-4-o-tolyl-nicotinamide.

MS m/e (%): 586 (M+H$^+$, 100).

EXAMPLE 53

N-(3,5-bis-Trifluoromethyl-benzyl)-N-methyl-6-piperazin-1-yl-4-o-tolyl-nicotinamide To a solution of 6.60 g (104 mmol) 4-{5-[(3,5-bis-trifluoromethyl-benzyl)-methyl-carbamoyl]-4-o-tolyl-pyridin-2-yl}-piperazine-1-carboxylic acid tert-butyl ester (Example 43) and 8.40 ml (207 mmol) methanol in 50 ml ethyl acetate 14.7 ml (207 mmol) acetyl chloride were added dropwise at 0° C. After 4 h the reaction mixture was diluted with ethyl acetate and treated with 1 N sodium hydroxide solution. The layers were separated and the aqueous layer extracted with dichloromethane. The combined organic layers were dried with sodium sulfate and concentrated to give 5.36 g of crude product. Flash column chromatography afforded 4.86 g (87.4%) of the title compound as a light brown solid.

MS m/e (%): 537 (M+H$^+$, 100).

EXAMPLE 54

N-(3,5-bis-Trifluoromethyl-benzyl)-6-[4-(2-hydroxy-ethyl)-piperazin-1-yl]-N-methyl-4-o-tolyl-nicotinamide A mixture of 100 mg (0.186 mmol) N-(3,5-bis-trifluoromethyl-benzyl)-N-methyl-6-piperazin-1-yl-4-o-tolyl-nicotinamide (Example 53), 0.030 ml (0.42 mmol) 2-bromo-ethanol and 46 mg (0.33 mmol) potassium carbonate in 2 ml acetonitrile was stirred at 45° C. for 70 h. After cooling to room temperature 10 ml 1 N sodium hydroxide solution were added. Extraction with 3 15-ml portions of ethyl acetate, drying with sodium sulfate and concentration gave 138 mg of the crude product. Flash column chromatography afforded 85 mg (78.6%) of the title compound as a white solid.

MS m/e (%): 581 (M+H$^+$, 100).

EXAMPLE 55

N-(3,5-bis-Trifluoromethyl-benzyl)-6-(4-cyanomethyl-piperazin-1-yl)-N-methyl-4-o-tolyl-nicotinamide The title compound was obtained as a white solid in comparable yield according to the procedure described above for the preparation of N-(3,5-bis-trifluoromethyl-benzyl)-6-[4-(2-hydroxy-ethyl)-piperazin-1-yl]-N-methyl-4-o-tolyl-nicotinamide (Example 54) using chloro-acetonitrile instead of 2-bromo-ethanol.

MS m/e (%): 576 (M+H$^+$, 100).

EXAMPLE 56

N-(3,5-bis-Trifluoromethyl-benzyl)-6-{4-[2-(2-hydroxy-ethoxy)-ethyl]-piperazin-1-yl}-N-methyl-4-o-tolyl-nicotinamide A mixture of 400 mg (0.746 mmol) N-(3,5-bis-trifluoromethyl-benzyl)-N-methyl-6-piperazin-1-yl-4-o-tolyl-nicotinamide (Example 53), 0.18 ml (1.7 mmol) 2-(2-chloroethoxy)-ethanol and 0.189 g (1.35 mmol) potassium carbonate in 8 ml acetonitrile was stirred at 85° C. for 48 h. After cooling to room temperature 40 ml 1 N sodium hydroxide solution were added. Extraction with 3 60-ml portions of dichloromethane, drying with sodium sulfate and concentration gave 528 mg of the crude product. Flash column chromatography afforded 300 mg (64.4%) of the title compound as a light-brown solid.

MS m/e (%): 625 (M+H$^+$, 100).

EXAMPLE 57

N-(3,5-bis-Trifluoromethyl-benzyl)-N-methyl-6-(4-[1,2,4]oxadiazol-3-ylmethyl-piperazin-1-yl)-4-o-tolyl-nicotinamide A mixture of 200 mg (0.373 mmol) N-(3,5-bis-trifluoromethyl-benzyl)-N-methyl-6-piperazin-1-yl-4-o-tolyl-nicotinamide (Example 53), 66 mg (0.56 mmol) 3-(chloromethyl)-1,2,4-oxadiazole and 62 mg (0.45 mmol) potassium carbonate in 4 ml acetonitrile was stirred at 45° C. for 1 h and at room temperature over night. The reaction mixture was diluted with 10 ml water and extracted with 3 30-ml portions of dichloromethane. Drying with sodium sulfate and concentration gave 244 mg of the crude product. Flash column chromatography afforded 80 mg (34.7%) of the title compound as a red-brown solid.

MS m/e (%): 619 (M+H$^+$, 100).

EXAMPLE 58

N-(3,5-bis-Trifluoromethyl-benzyl)-N-methyl-6-[4-(5-oxo-4,5-dihydro-1H-[1,2,4]triazol-3-ylmethyl)-piperazin-1-yl]-4-o-tolyl-nicotinamide A mixture of 800 mg (1.49 mmol) N-(3,5-bis-trifluoromethyl-benzyl)-N-methyl-6-piperazin-1-yl-4-o-tolyl-nicotinamide (Example 53), 296 mg (1.79 mmol) N-carbomethoxy-2-chloroacetamidrazone and 0.52 ml (3.0 mmol) N-ethyl-diisopropylamine in 14 ml acetonitrile was stirred at room temperature for 2 h. The reaction mixture was diluted with 20 ml water and extracted with 3 50-ml portions of dichloromethane. The combined extracts were dried with sodium sulfate and concentrated. The residue was dissolved in 14 ml DMF, and 0.29 ml (1.6 mmol) N-ethyl-diisopropylamine were added. The reaction mixture was stirred at 140° C. over night. Concentration and drying in high vacuo gave 1.09 g of crude product. Flash column chromatography afforded 820 mg (86.8%) of the title compound as a light-brown solid.

MS m/e (%): 634 (M+H$^+$, 100).

EXAMPLE 59

N-(3,5-bis-Trifluoromethyl-benzyl)-6-(4-formyl-piperazin-1-yl)-N-methyl-4-o-tolyl-nicotinamide To a mixture of 0.089 ml (1.1 mmol) N,N-dimethylformamide and 38 mg (0.56 mmol) imidazole 0.071 ml (0.56 mmol) trimethylchlorosilane were added dropwise at room temperature. The reaction mixture was cooled to 0° C., and 0.10 g (0.19 mmol) N-(3,5-bis-trifluoromethyl-benzyl)-N-methyl-6-piperazin-1-yl-4-o-tolyl-nicotinamide (Example 53) were added. The ice-water bath was removed and the mixture stirred over night. The reaction was quenched with a mixture of 2 ml 1 N aqueous hydrochloric acid solution and 4 ml water, and the mixture was extracted with ethyl acetate. The combined extracts were dried with sodium sulfate and concentrated. Flash column chromatography afforded 81 mg (82%) of the, title compound as a white solid.

MS m/e (%): 565 (M+H⁺, 100).

EXAMPLE 60

N-Methyl-N-(2-methyl-naphthalen-1-ylmethyl)-6-morpholin-4yl-4-o-tolyl-nicotinamide a) N-Methyl-6-morpholin-4-yl-4-o-tolyl-nicotinamide The title compound was obtained as an off-white solid in comparable yield according to the procedure described above for the preparation of 4-{5-[(3,5-bis-trifluoromethyl-benzyl)-methyl-carbamoyl]-4-o-tolyl-pyridin-2-yl}-piperazine-1-carboxylic acid tert-butyl ester (Example 43, step b) using morpholine instead of 1-tert-butoxycarbonyl piperazine.

MS m/e (%): 311 (M⁺, 63).

b) N-Methyl-N-(2-methyl-naphthalen-1-ylmethyl)-6-morpholin-4-yl-4-o-tolyl-nicotinamide The title compound was obtained as a white solid in comparable yield according to the procedure described above for the preparation of N-(3,5-bis-trifluoromethyl-benzyl)-N-methyl-6-morpholin-4-yl-4-o-tolyl-nicotinamide (Example 12, step e)) using 1-chloromethyl-2-methylnaphthalene instead of 3,5-bis-trifluoromethyl-benzyl bromide.

MS m/e (%): 466 (M+H⁺, 100).

EXAMPLE 61

N-Methyl-6-morpholin-4-yl-N-naphthalen-1-ylmethyl-4-o-tolyl-nicotinamide

The title compound was obtained as a colorless viscous oil in comparable yields according to the procedures described above for the preparation of N-methyl-N-(2-methyl-naphthalen-1-ylmethyl)-6-morpholin-4-yl-4-o-tolyl-nicotinamide (Example 60) using 1-chloromethylnaphthalene instead of 1-chloromethyl-2-methylnaphthalene in step b).

MS m/e (%): 452 (M+H⁺, 100).

EXAMPLE 62

N-(2-Methoxy-naphthalen-1-ylmethyl)-N-methyl-6-morpholin-4-yl-4-o-tolyl-nicotinamide The title compound was obtained as a colorless viscous oil in comparable yields according to the procedures described above for the preparation of N-methyl-N-(2-methyl-naphthalen-1-ylmethyl)-6-morpholin-4-yl-4-o-tolyl-nicotinamide (Example 60) using toluene-4-sulfonic acid2-methoxy-naphthalen-1-ylmethyl ester instead of 1-chloromethyl-2-methylnaphthalene in step b).

MS m/e (%): 482 (M+H⁺, 100).

EXAMPLE 63

N-(2-Methoxy-benzyl)-N-methyl-6-morpholin-4-yl-4-o-tolyl-nicotinamide

The title compound was obtained as a colorless viscous oil in comparable yields according to the procedures described above for the preparation of N-methyl-N-(2-methyl-naphthalen-1-ylmethyl)-6-morpholin-4-yl-4-o-tolyl-nicotinamide (Example 60) using 2-methoxy-benzyl chloride instead of 1-chloromethyl-2-methylnaphthalene in step b).

MS m/e (%): 432 (M+H⁺, 100).

EXAMPLE 64

N-(5-Chloro-2-methoxy-benzyl)-N-methyl-6-morpholin-4-yl-4-o-tolyl-nicotinamide

The title compound was obtained as a white solid in comparable yields according to the procedures described above for the preparation of N-methyl-N-(2-methyl-naphthalen-1-ylmethyl)-6-morpholin-4-yl-4-o-tolyl-nicotinamide (Example 60) using 5-chloro-2-methoxy-benzyl chloride instead of 1-chloromethyl-2-methylnaphthalene in step b).

MS m/e (%): 466 (M+H⁺, 100).

EXAMPLE 65

N-(2-Chloro-5-methoxy-benzyl)-N-methyl-6-morpholin-4-yl-4-o-tolyl-nicotinamide

The title compound was obtained as a white solid in comparable yields according to the procedures described above for the preparation of N-methyl-N-(2-methyl-naphthalen-1-ylmethyl)-6-morpholin-4-yl-4-o-tolyl-nicotinamide (Example 60) using 2-chloro-5-methoxy-benzyl bromide instead of 1-chloromethyl-2-methylnaphthalene in step b).

MS m/e (%): 466 (M+H⁺, 100).

EXAMPLE 66

N-(2-Chloro-5-methoxy-benzyl)-N-methyl-6-morpholin-4-yl-4-o-tolyl-nicotinamide

The title compound was obtained as a white solid in comparable yields according to the procedures described above for the preparation of N-methyl-N-(2-methyl-naphthalen-1-ylmethyl)-6-morpholin-4-yl-4-o-tolyl-nicotinamide (Example 60) using 2,3,4,5,6-pentafluoro-benzyl bromide instead of 1-chloromethyl-2-methylnaphthalene in step b).

MS m/e (%): 492 (M+H⁺, 100).

EXAMPLE 67

N-Methyl-6-morpholin-4-yl-N-naphthalen-2-ylmethyl-4-o-tolyl-nicotinamide

The title compound was obtained as a white solid in comparable yields according to the procedures described above for the preparation of N-methyl-N-(2-methyl-naphthalen-1-ylmethyl)-6-morpholin-4-yl-4-o-tolyl-nicotinamide (Example 60) using 2-chloromethyl-naphthalene instead of 1-chloromethyl-2-methylnaphthalene in step b).

MS m/e (%): 452 (M+H⁺, 100).

EXAMPLE 68

N-[2-Methoxy-5-(5-trifluoromethyl-tetrazol-1-yl)-benzyl]-N-methyl-6-morpholin-4-yl-4-o-tolyl-nicotinamide The title compound was obtained as a white solid in comparable yields according to the procedures described above for the preparation of N-methyl-N-(2-methyl-naphthalen-1-ylmethyl)-6-morpholin-4-yl-4-o-tolyl-nicotinamide (Example 60) using toluene-4-sulfonic acid [2-methoxy-5-(5-trifluoromethyl-tetrazol-1-yl)-phenyl]- methyl ester instead of 1-chloromethyl-2-methylnaphthalene in step b).

MS m/e (%): 568 (M+H$^+$, 100).

EXAMPLE 69

N-(1,4-Dimethoxy-naphthalen-2-ylmethyl)-N-methyl-6-morpholin-4-yl-4-o-tolyl-nicotinamide The title compound was obtained as a colorless viscous oil in comparable yields according to the procedures described above for the preparation of N-methyl-N-(2-methyl-naphthalen-1-ylmethyl)-6-morpholin-4-yl-4-o-tolyl-nicotinamide (Example 60) using 2-chloromethyl-1,4-dimethoxy-naphthalene instead of 1-chloromethyl-2-methylnaphthalene in step b).

MS m/e (%): 512 (M+H$^+$, 100).

EXAMPLE 70

5'-[(3,5-bis-Trifluoromethyl-benzyl)-methyl-carbamoyl]-4'-o-tolyl-3,4,5,6-tetrahydro-2H-[1,2']bipyridinyl-4-carboxylic Acid A mixture of 200 mg (0.33 mmol) 5'-[(3,5-bis-trifluoromethyl-benzyl)-methyl-carbamoyl]-4'-o-tolyl-3,4,5,6-tetrahydro-2H-[1,2']bipyridinyl-4-carboxylic acid ethyl ester (Example 45), 10 ml 1N aqueous sodium hydroxide solution and 10 ml methanol was stirred at room temperature over night. After washing with 2 portions of ethyl acetate the aqueous layer was acidified to pH 4 with 1N aqueous hydrochloric acid solution. Extraction with dichloromethane, drying with sodium sulfate and flash column chromatography afforded 81 mg (42%) of the title compound as a white solid.

MS m/e (%): 580 (M+H$^+$, 100).

EXAMPLE 71

N-(3,5-bis-Trifluoromethyl-benzyl)-N-methyl-6-[4-(1H-tetrazol-5-ylmethyl)-piperazin-1-yl]-4-o-tolyl-nicotinamide A mixture of 0.10 g (0.17 mmol) N-(3,5-bis-trifluoromethyl-benzyl)-6-(4-cyanomethyl-piperazin-1-yl)-N-methyl-4-o-tolyl-nicotinamide (Example 55), 34 mg (0.52 mmol) sodium azide and 36 mg (0.26 mmol) triethylammonium chloride in 1 ml 1-methyl-2-pyrrolidone was heated at reflux for 2 h. After cooling to room temperature 6 ml ice water were added. The mixture was acidified with 1N hydrochloric acid solution to pH 1–2 and extracted with dichloromethane. Drying of the combined extracts with sodium sulfate, concentration and flash column chromatography afforded 95 mg (88%) of the title compound as a light brown solid.

MS m/e (%): 619 (M+H$^+$, 100).

EXAMPLE 72

N-(6-Benzylamino-4-o-tolyl-pyridin-3-yl)-2-(3,5-bis-trifluoromethyl-phenyl)-N-methyl-isobutyramide a) 2-Benzyl-N-5-methyl-4-o-tolyl-pyridine-2,5-diamine The title compound was prepared following the procedures described above for the synthesis of methyl-6-morpholin-4-yl-4-o-tolyl-pyridin-3-yl)-amine (Example 23, step f).

MS m/e (%): 304 (M+H$^+$, 100).

b) Benzyl-(5-methylamino-4-o-tolyl-pyridin-2-yl)-carbamic Acid Benzyl Ester

To a solution of 2.03 g (6.7 mmol) N2-benzyl-N5-methyl-4-o-tolyl-pyridine-2,5-diamine in 100 ml dichloromethane and 40 ml N-ethyldiisopropylamine was added dropwise at 0° C. a solution of 2.1 ml (14.09 mmol) benzyl chloroformate in 50 ml dichloromethane. After stirring for 2 h at room temperature the reaction mixture was washed with water (2×50 ml), brine (50 ml), dried (magnesium sulfate) and evaporated. Chromatography of the residue afforded 2.36 g (80%) of the title compound as light brown crystals. M.p. 110–112° C.

MS m/e (%): 438 (M+H$^+$, 100).

c) Benzyl-(5-[2-(3,5-bis-trifluoromethyl-phenyl)-2-methyl-propionyl]-methyl-amino-4-o-tolyl-pyridin-2-yl)-carbamic Acid Benzyl Ester To a solution of 1.075 g (2.5 mmol) benzyl-(5-methylamino-4-o-tolyl-pyridin-2-yl)-carbamic acid benzyl ester in 10 ml dichloromethane and 1 ml N-ethyldiisopropylamine was added dropwise at 0° C. a solution of 1.15 g (3.5 mmol) 2-(3,5-bis-trifluoromethyl-phenyl)-2-methyl-propionic acid chloride in 2 ml dichloromethane and the mixture was stirred for 3 h at room temperature. The solution was washed with water (20 ml), saturated aqueous sodium hydrogencarbonate solution (20 ml) and brine (20 ml), dried (magnesium sulfate) and evaporated. Chromatography of the residue afforded 1.15 g (62%) of the tide compound as a yellow oil.

MS m/e (%): 720 (M+H$^+$, 100).

d) N-(6-Benzylamino-4-o-tolyl-pyridin-3-yl)-2-(3,5-bis-trifluoromethyl-phenyl)-N-methyl-isobutyramide To a solution of 973 mg (1.35 mmol) benzyl-(5-{[2-(3,5-bis-trifluoromethyl-phenyl)-2-methyl-propionyl]-methyl-amino}-4-o-tolyl-pyridin-2-yl)-carbamic acid benzyl ester in 13 ml methanol and 1 ml N,N-dimethylformamide was added 40 mg 10% palladium on activated charcoal and the mixture was hydrogenated (room temperature, 1 bar) for 1 h. Filtration of the catalyst and evaporation of the filtrate afforded 795 mg (quantitative) of the title compound as a yellow oil.

MS m/e (%): 586 (M+H$^+$, 100).

EXAMPLE 73

N-(6-Amino-4-o-tolyl-pyridin-3-yl)-2-(3,5-bis-trifluoromethyl-phenyl)-N-methyl-isobutyramide A solution of 750 mg (1.28 mmol) N-(6-benzylamino-4-o-tolyl-pyridin-3-yl)-2-(3,5-bis-trifluoromethyl-phenyl)-N-methyl-isobutyramide (Example 73, step d) in 25 ml of a 5 N solution of hydrochloric acid in ethanol was evaporated to dryness and the residue was dissolved in 30 ml methanol and hydrogenated in the presence of 60 mg 10% palladium on activated charcoal (room temperature, 10 bar) for 20 h. After filtration of the catalyst and evaporation of the solvent the residue was dissolved in 30 ml ethyl acetate, washed twice with saturated aqueous sodium hydrogencarbonate solution and dried (magnesium sulfate). Evaporation of the solution afforded 514 mg (81%) of the title compound as light brown crystals.

MS m/e (%): 496 (M+H$^+$, 100).

EXAMPLE 74

2-(3,5-bis-Trifluoromethyl-phenyl)-N-[6-(dimethylamino-methyleneamino)-4-o-tolyl-pyridin-3-yl]-N-methyl-isobutyramide To a solution of 100 mg (0.2 mmol) N-(6-amino-4-o-tolyl-pyridin-3-yl)-2-(3,5-bis-trifluoromethyl-phenyl)-N- methyl-isobutyramide (Example 73) in 4 ml N,N-dimethylformamide was added at 0° C. 11 mg (0.252 mmol) sodium hydride as a 60% dispersion in oil and the mixture was stirred for 30 min without cooling. Then 28 μl (0.218 mmol) benzenesulfonyl chloride were added at 0° C. and the solution was stirred over night at room temperature. The reaction mixture was added to water and extracted with ethyl acetate (3×10 ml). The combined extracts were washed with water (3×20 ml), brine (20 ml), dried (magnesium sulfate) and evaporated. Chromatography of the residue afforded 51 mg (46%) of the title compound as a white foam.

MS m/e (%): 551 (M+H$^+$, 100).

EXAMPLE 75

2-(3,5-bis-Trifluoromethyl-phenyl)-N-(6-methanesulfonylamino-4-o-tolyl-pyridin-3-yl)-N-methyl-isobutyramide To a solution of 100 mg (0.2 mmol) N-(6-amino-4-o-tolyl-pyridin-3-yl)-2-(3,5-bis-trifluoromethyl-phenyl)-N-methyl-isobutyramide i (Example 73) in 2 ml pyridine were added 27 μl (0.35 mmol) methanesulfonyl chloride and the mixture was stirred over night at room temperature. After evaporation of the solvent the residue was dissolved in ethyl acetate, washed twice with saturated aqueous sodium hydrogencarbonate solution, brine and dried (magnesium sulfate). Chromatography of the residue afforded 24 mg (42%) of the title compound as a white foam.

MS m/e (%): 574 (M+H$^+$, 100).

EXAMPLE 76

N-(6-Benzenesulfonylamino-4-o-tolyl-pyridin-3-yl)-2-(3,5-bis-trifluoromethyl-phenyl)-N-methyl-isobutyramide To a solution of 100 mg (0.2 mmol) N-(6-amino-4-o-tolyl-pyridin-3-yl)-2-(3,5-bis-trifluoromethyl-phenyl)-N-methyl-isobutyramide in 4 ml dichloromethane and 85 μl N-ethyldiisopropylamine were added 56 μl (0.436 mmol) benzenesulfonyl chloride and the mixture was stirred over night at room temperature. The reaction mixture was washed twice with saturated aqueous sodium hydrogencarbonate solution and dried (magnesium sulfate). Chromatography of the residue afforded 26 mg (28%) of the title compound as a white foam.

MS m/e (%): 634 (M−H$^+$, 100).

EXAMPLE 77

N-(3,5-bis-Trifluoromethyl-benzyl)-N-methyl-6-(4-methyl-piperazin-1-yl)-4-o-tolyl-nicotinamide a) Chloro-N-methyl-nicotinamide To a mixture of 63.0 g (0.40 mol) 6-chloronicotinic acid and 37.7 ml (0.52 mol) thionylchloride was added 340 ml toluene and 0.92 ml (12.0 mmol) DMF. The brown suspension was heated to 95° C. and stirred at 95° C. for 1.5 h. The solvent was subsequently removed and the residue treated with 340 ml CH$_2$Cl$_2$. This solution was cooled to 2° C. and treated with 81.0 g (1.2 mol) methylaminhydrochloride. To the so formed brown suspension was added at −2° C. to −6° C. dropwise over 75 min. 167.5 ml (1.2 mol) NEt$_3$ (the reaction was finished after further 30 min.). The reaction mixture was poured onto 400 ml brine and 100 ml sat. aqueous sodium carbonate and extracted. The aqueous phase was extracted with total 2.41 CH$_2$Cl$_2$. The organic phases were washed with 400 ml sat. aqueous sodium carbonate and 400 ml brine, combined, dried over MgSO$_4$. The solvent was removed under reduced pressure to give 67.5 g (98.9%) product as brown crystals, m.p. 147.5–148.0° C.

MS (EI): m/e=172 (13), 171 (18), 170 ([M]37), 169 (47), 142 (34), 140 (100), 135 (67), 112 (43).

b) (RS)-6-(4-Methyl-piperazin-1-yl)-4-o-tolyl-4,5-dihydro-pyridine-3-carboxylic Acid Methylamide A solution of 3.0 g (17.6 mmol) 6-chloro-N-methyl-nicotinamide in 42.0 ml THF was treated at 4° C. dropwise over 15 min. with 43.8 ml (43.8 mmol) o-tolylmagnesiumchloride-solution (1M in THF). The reaction mixture was stirred for 2 h at r.t., cooled to 0° C. and treated dropwise with 50 ml 5% aqueous NH$_4$Cl. The aqueous phase was separated and extracted twice with toluene and the organic phases were washed twice with 5% aqueous NH$_4$Cl. The combined organic phases were dried over Na$_2$SO$_4$ and the solvent was removed under reduced pressure to yield 5.4 g (94.6%) product as yellowish crystals, m.p. 137.0–138.0° C.

MS (ISP): m/e=328 (24), 327 ([M+H$^+$] 100), 270 (12).

c) N-Methyl-6-(4-methyl-piperazin-1-yl)-4-o-tolyl-nicotinamide

A solution of 1.5 g (4.6 mmol) (RS)-6-(4-methyl-piperazin-1-yl)-4-o-tolyl-4,5-dihydro-pyridine-3-carboxylic acid methylamide in 15 ml CHCl$_3$ was treated with 2.3 g (23.0 mmol) MnO$_2$. The black suspension was heated to 65° C., stirred for 3 h at 65° C. and treated again with 2.3 g (23.0 mmol) MnO$_2$, stirred for 3 h and added an other 0.9 g (9.2 mmol) MnO$_2$. The reaction mixture was stirred for 10.5 h at 65° C., treated with 0.9 g (9.2 mmol) MnO$_2$, stirred for 1 h at 65° C. and cooled to r.t. After filtration of the MnO$_2$ the solvent was removed under reduced pressure and the residue purified by chromatography over silica gel (CHCl$_3$: MeOH= 4:1) to yield 1.24 g (83.2%) product as beige foam.

MS (ISP): m/e=326 (18), 325 ([M+H$^+$] 100), 268 (31).

d) 6-Chloro-N-methyl-4-o-tolyl-nicotinamide

A solution of 1.5 g (8.8 mmol) 6-chloro-N-methyl-nicotinamide in 18 ml THF was added at 4° C. over 15 min to a solution of 21.9 ml (21.9 mmol) o-tolylmagnesium chloride 1M in THF. The reaction mixture was stirred at r.t. for 2 h cooled to 4° C. and treated dropwise over 10 min with 30.0 ml 5% aqueous NH$_4$Cl. The aqueous phase was separated and extracted twice with THF and the organic phases were washed twice with 5% aqueous NH$_4$Cl. The combined organic phases were dried over Na$_2$SO$_4$ and subsequently treated at r.t. in four portions over 10 h with 0.9 g (5.7 mmol) KMnO$_4$. The reaction mixture was stirred for 5.5 h at r.t., filtrated and the solvent was removed. The residue was purified by chromatography over silica gel (CHCl$_3$) to yield 1.8 g (78.9%) product as a yellow oil.

MS (EI): m/e=260 ([M] 12), 245 (17), 230 (100), 194 (18), 166 (32), 139 (27).

e) N-Methyl-6-(4-methyl-piperazin-1-yl)-4-o-tolyl-nicotinamide

A solution of 3.2 g (12.2 mmol) 6-chloro-N-methyl-4-o-tolyl-nicotinamide in 6.7 ml (60.3 mmol) 1-methylpiperazine was stirred at 100° C. for 2.5 h. The reaction mixture was cooled to r.t., treated with 10 ml 0. 1N NaOH and extracted. The aqueous phase was separated and extracted twice with THF and the organic phases were washed twice with brine. The combined organic phases were dried over Na$_2$SO$_4$, the solvent was removed under reduced pressure and the residue purified by chromatography over silica gel (CH$_2$Cl$_2$: MeOH=99:1) to yield 3.3 g (83.7%) product as beige foam.

MS (EI): m/e=324 ([M] 10), 268 (12), 254 (100).

f) N-(3,5-bis-Trifluoromethyl-benzyl)-N-methyl-6-(4-methyl-piperazin-1-yl)-4-o-tolyl-nicotinamide To a solution of 2.5 g (7.7 mmol) N-methyl-6-(4-methyl-piperazin-1-yl)-4-o-tolyl-nicotinamide in 51 ml THF at 4° C. was added dropwise over 30 min 10.2 ml (10.2 mmol) potassium bis(trimethylsilyl) amide (1M in THF). The reaction mixture was stirred for 30 min and subsequently treated at 4° C. dropwise over 30 min with 1.46 ml (7.7 mmol) 3,5-bis-trifluoromethyl-benzylbromide. The reaction mixture was stirred for 1.5 h at 4° C., treated with 31 ml water and extracted. The aqueous phase was separated and adjusted to pH 12 with 2N NaOH and subsequently extracted with 30 ml ethyl acetate. The aqueous phase was separated, the combined organic phases were dried over $Na_2SO_4$, the solvent was removed under reduced pressure and the residue purified by chromatography over silica gel ($CH_2CG_2$: MeOH=99:1) to yield 3.6 g (84.1%) product as beige foam.

MS (ISP): m/e=552 (47), 551 ([M+H$^+$] 100).

EXAMPLE 78

Methyl-[6-(4-methyl-piperazin-1-yl)-4-o-tolyl-pyridin-3-yl]-amine a) 6-Chloro-4-o-tolyl-nicotinic Acid 13.0 g (82.5 mMol) 6-Chloro-nicotinic acid in 65 ml THF were cooled to 0° C. and 206.3 ml (206.3 mMol) o-tolylmagnesium chloride solution (1M in THF) were added over 45 minutes. The solution obtained was further stirred 3 hours at 0° C. and overnight at room temperature. It was cooled to −60° C. and 103.8 ml (1.8 Mol) acetic acid were added, followed by 35 ml THF and 44.24 g (165 mMol) manganese(III) acetate dihydrate. After 30 minutes at −60° C. and one hour at room temperature, the reaction mixture was filtered and THF removed under reduced pressure. The residue was partitioned between water and dichloromethane and extracted. The crude product was filtered on silica gel (eluent:ethyl acetate/toluene/formic acid 20:75:5) then partitioned between 200 ml aqueous half-saturated sodium carbonate solution and 100 ml dichloromethane. The organic phase was washed with 50 ml aqueous half-saturated sodium carbonate solution. The combined aqueous phases were acidified with 25 ml aqueous HCl 25% and extracted with dichloromethane. The organic extracts were dried ($Na_2SO_4$) and concentrated under reduced pressure to yield 10.4 g (51%) of 6-chloro-4-o-tolyl-nicotinic acid as a yellow foam.

MS (ISN): 246 (M−H, 100), 202 (M—$CO_2H$, 85), 166 (36).

b) 6-Chloro-4-o-tolyl-nicotinamide

To a solution of 8.0 g (32.3 mMol) 6-chloro-4-o-tolyl-nicotinic acid in 48.0 ml THF were added 3.1 ml (42.0 mMol) thionylchloride and 143 µl (1.8 mMol) DMF. After 2 hours at 50° C., the reaction mixture was cooled to room temperature and added to a solution of 72.5 ml aqueous ammonium hydroxide 25% and 96 ml water cooled to 0° C. After 30 minutes at 0° C., THF was removed under reduced pressure and the aqueous layer was extracted with ethyl acetate. Removal of the solvent yielded 7.8 g (98%) 6-chloro-4-o-tolyl-nicotinamide as a beige crystalline foam.

MS (ISP): 247 (M+H$^+$, 100).

c) 6-(4-Methyl-piperazin-1-yl)-4-o-tolyl-nicotinamide 1.0 g (4.05 mMol) 6-Chloro-4-o-tolyl-nicotinamide in 9.0 ml 1-methyl-piperazine was heated to 100° C. for 2 hours. The excess N-methyl-piperazine was removed under high vacuum and the residue was filtered on silica gel (eluent:dichloromethane) to yield 1.2 g (95%) 6-(4-methyl-piperazin-1-yl)-4-o-tolyl-nicotinamide as a light yellow crystalline foam.

MS (ISP): 311 (M+H$^+$, 100), 254 (62).

d) 6-(4-Methyl-piperazin-1-yl)-4-o-tolyl-pyridin-3-ylamine

A solution of 0.2 g (0.6 mMol) 6-(4-methyl-piperazin-1-yl)-4-o-tolyl-nicotinamide in 1.0 ml methanol was added to a solution of 103 mg (2.6 mMol) sodium hydroxide in 1.47 ml (3.2 mMol) NaOCl (13%)and heated for 2 hours at 70° C. After removal of methanol, the aqueous layer was extracted with ethyl acetate. The combined organic extracts were dried ($Na_2SO_4$), concentrated under reduced pressure and the residue filtered on silica gel (eluent:dichloromethane/methanol 4:1) to yield 100 mg (70%) 6-(4-methyl-piperazin-1-yl)-4-o-tolyl-pyridin-3-ylamine as a brown resin.

MS (ISP): 283 (M+H$^+$, 100), 226 (42).

e) [6-(4-Methyl-piperazin-1-yl)-4-o-tolyl-pyridin-3-yl]-carbamic Acid Methyl Ester 2.15 ml (11.6 mMol) Sodium methoxide in methanol were added over 30 minutes to a suspension of 0.85 g (4.6 mMol) N-bromosuccinimide in 5.0 ml dichloromethane cooled to −5° C. The reaction mixture was stirred 16 hours at −5° C. Still at this temperature, a solution of 1.0 g (3.1 mMol) 6-(4-methyl-piperazin-1-yl)-4-o-tolyl-nicotinamide in 5.0 ml methanol was added over 20 minutes and stirred for 5 hours. 7.1 ml (7.1 mMol) Aqueous HCl 1N and 20 ml dichloromethane were added. The phases were separated and the organic phase was washed with deionized water. The aqueous phases were extracted with dichloromethane, brought to pH=8 with aqueous NaOH 1N and further extracted with dichloromethane. The latter organic extracts were combined, dried ($Na_2SO_4$) and concentrated to yield 1.08 g (quant.) [6-(4-methyl-piperazin-1-yl)-4-o-tolyl-pyridin-3-yl]-carbamic acid methyl ester as a grey foam.

MS (ISP): 341 (M+H$^+$, 100), 284 (35).

f) Methyl-[6-(4-methyl-piperazin-1-yl)-4-o-tolyl-pyridin-3-yl]-amine

A solution of 0.5 g (1.4 mMol)[6-(4-methyl-piperazin-1-yl)-4-o-tolyl-pyridin-3-yl]-carbamic acid methyl ester in 3.0 ml dichloromethane was added over 10 minutes to a solution of 1.98 ml (6.9 mMol) Red-Al® (70% in toluene) and 2.5 ml toluene (exothermic, cool with a water bath to avoid temperature to go >50° C). The reaction mixture was stirred 2 hours at 50° C. in $CH_2Cl_2$, extracted with ethyl acetate and cooled to 0° C. 4 ml Aqueous NaOH 1N were carefully (exothermic) added over 15 minutes, followed by 20 ml ethyl acetate. The phases were separated and the aqueous phase was extracted with ethyl acetate. The combined organic extracts were washed with deionized water and brine, dried ($Na_2SO_4$) and concentrated under reduced pressure to yield 0.37 g (89%) methyl-[6-(4-methyl-piperazin-1-yl)-4-o-tolyl-pyridin-3-yl]-amine as an orange resin.

MS (ISP): 297 (M+H$^+$, 100).

Alternatively 35 g (124 mMol) 6-(4-Methyl-piperazin-1-yl)-4-o-tolyl-pyridin-3-ylamine were dissolved in 273 ml ortho-formic acid trimethyl ester and 8 drops trifluoroacetic acid were added. The reaction mixture was refluxed for 3 hours then concentrated under reduced pressure and dried under high vacuum. The residue was dissolved in 100 ml tetrahydrofuran and added dropwise at 0° C. to a suspension of 9.4 g (248 mMol) lithium alimunium hydride in 300 ml tetrahydrofuran. The reaction mixture was stirred at room temperature for 1 hour, cooled gain to 0° C. and its pH was brought to 1 by careful addition of aqueous HCl 28%. After 5 minutes, the pH was raised to 10 by addition of aqueous NaOH 28%, the reaction mixture was filtered on Hyflo and concentrated under reduced pressure. The residue was chromatographed (eluent:dichloromethane/methanol 9:1) to yield 23.6 g (64%) methyl-[6-(4-methyl-piperazin-1-yl)-4-o-tolyl-pyridin-3-yl]-amine as a brown oil.

MS (ISP): 297 (M+H$^+$, 100).

EXAMPLE 79

N-Benzyl-6-morpholin-4-yl-4-o-tolyl-nicotinamide a) N-Benzyl-6-chloro-nicotinamide 3.5 ml (47.6 mMol) Thionylchloride and 50 µl DMF were added to a suspension of 5.0 g (31.7 mMol) 6-chloronicotinic acid in 50 ml toluene and the reaction mixture was heated at 80° C. for 2 hours. The solvent and excess thionyl chloride were removed under reduced pressure and the residue was dissolved in 50 ml dichloromethane. After cooling to 0° C., 10.4 ml (95.2 mMol) benzylamine were added over 20 minutes and after 30 minutes further stirring at room temperature, the reaction mixture was poured onto 50 ml aqueous saturated sodium bicarbonate solution. Extraction with dichloromethane, followed by crystallization from ethyl acetate/n-hexane 2:1 gave 6.13 g (78%) N-benzyl-6-chloro-nicotinamide as light brown crystals of m.p.=113–114° C.

MS (EI): 246 (M$^+$, 100), 211 (M$^+$—Cl, 19), 140 (M$^+$—NHBn, 64).

b) N-Benzyl-6-chloro-4-o-tolyl-nicotinamide

A solution of 0.5 g (2.0 mMol) N-benzyl-6-chloro-nicotinamide in 5.0 ml THF was added over 25 minutes to 10.1 ml (10.1 mMol) of o-tolylmagnesium chloride solution (1M in THF) cooled to 0° C. After 2.5 hours stirring at room temperature, the reaction mixture was cooled again to 0° C. and 4.0 ml acetic acid were added over 15 minutes followed by 1.1 g (4.1 mMol) manganese triacetate dihydrate. After stirring for 1 hour at room temperature, the reaction mixture was filtered and the filtrate was poured onto 20 ml deionized water. Sodium bicarbonate was added portionwise to bring the pH to 7 and the phases were separated. The aqueous layer was extracted with dichloromethane. The combined organic extracts were washed with water, dried (Na$_2$SO$_4$) and evaporated. The residue was purified by flash chromatography (eluent ethyl acetate/n-hexane 2:1) to yield 0.6 g (88%) N-benzyl-6-chloro-4-o-tolyl-nicotinamide as an orange resin.

MS (EI): 336 (M$^+$, 49), 230 (M$^+$—PhNH, 100), 106 (75), 91 (82).

c) N-Benzyl-6-(4-methyl-piperazin-1-yl)-4-o-tolyl-nicotinamide

A solution of 2.5 g (7.4 mMol) N-benzyl-6-chloro-4-o-tolyl-nicotinamide and 3.3 ml (29.7 mMol) N-methyl-piperazine in 25 ml ethyl acetate was heated to 80° C. for 18 hours. After adding 1.65 ml (14.8 mMol) N-methyl-piperazine, the reaction mixture was further heated 2 hours at 80° C., and after a new addition of 1.65 ml (14.8 mMol) N-methyl-piperazine 6 hours at 85° C. It was then concentrated under reduced pressure and the residue was filtered on silica gel (eluent: CH$_2$Cl$_2$/MeOH 5:1) to yield 2.21 g (74%) N-benzyl-6-(4-methyl-piperazin-1-o-tolyl-nicotinamide as a yellow resin.

MS (ISP): 401 (M+H$^+$, 100), 344 (18).

d) N-Benzyl-6-morpholin-4-yl-4-o-tolyl-nicotinamide

A mixture of 5.0 g (14.8 mMol) of N-benzyl-6-chloro-4-o-tolyl-nicotinamide and 25 ml morpholine was heated to 100° C. for 3.5 hours. After cooling to room temperature, extractive work-up with ethyl acetate, water and brine gave 5.7 g (100%) N-benzyl-6-morpholin-4-yl-4-o-tolyl-nicotinamide as a yellow powder.

MS (ISP): 388 (M+H$^+$, 100).

EXAMPLE 80

2-(3,5-bis-Trifluoromethyl-phenyl)-N-methyl-N-(6-morpholin-4-yl-4-o-tolyl-pyridin-3-yl)-isobutyramide a) N-tert.-Butyl-6-chloro-nicotinamide 25.7 ml (349 mMol) Thionylchloride and 0.5 ml (6.35 mMol) DMF were added to a suspension of 50.0 g (317 mMol) 6-chloro-nicotinic acid in 250 ml toluene and the reaction mixture was heated to 80° C. for 2 hours. After cooling to 10° C., 100.5 ml (952 mMol) tert.-butylamine were added over 40 minutes and stirring was pursued for 30 minutes at the same temperature. 250 ml Aqueous sodium hydroxide 2N were added and the mixture was stirred 30 minutes at room temperature. Dilution with 300 ml water and extraction with ethyl acetate yielded 63.3 g (94%) N-tert.-butyl-6-chloro-nicotinamide as a beige powder of m.p.=108–110° C.

MS (ISP): 235 (M+Na$^+$, 36), 213 (M+H$^+$, 100), 157 (M—C$_4$H$_8$, 25).

b) N-tert.-Butyl-6-chloro-4-o-tolyl-nicotinamide 92 ml (92 mMol) o-Tolylmagnesium chloride solution (1M in THF) were added over 15 minutes to a solution of 5.0 g (23 mMol) N-tert.-butyl-6-chloro-nicotinamide in 25 ml THF cooled to 0° C. The reaction mixture was stirred 18 hours at 30° C. and cooled again to 0° C. 5.6 ml (138 mMol) Methanol were added over 30 minutes, stirring was pursued for 10 minutes and 6.3 g (27 mMol) 2,3-dichloro-5,6-dicyano-1,4-benzoquinone were added. After 1 hour at room temperature, the reaction mixture was concentrated to 50 g under reduced pressure, heated to 50° C. and 100 ml tert.-butyl-methylether were added. The resulting suspension was refluxed for 30 minutes, cooled to room temperature and, after 1 hour, filtered off. The filtrate was concentrated and dried under high vacuum to yield 6.3 g (90%) of N-tert.-butyl-6-chloro-4-o-tolyl-nicotinamide as an orange foam.

MS (ISP): 303 (M+H$^+$, 100), 247 (M—C$_4$H$_8$, 10).

Alternatively

To a solution of 3-N-tert-Butyl-6-chloro-nicotinamide (10.0 g, 47.0 mmol) in THF (50 ml) at 2–4° C. was added a solution of o-tolylmagnesium chloride (1.0 M solution in THF, 190 ml, 188.10 mmol, 4.0 eq) dropwise over 30 minutes and the resulting suspension warmed to 30° C. for 18 h. The obtained brown solution was cooled to 0–4° C. and MeOH (11.43 ml, 282.10 mmol, 6 eq) added dropwise over 20 min followed by o-chloroanil (15.34 g, 61.13 mmol, 1.3 eq.) The dark green solution was stirred at 22° C. for one hour and then concentrated to give 71.71 g of a blue foam. This was taken up in MeOH (200 ml) and H$_2$O (75 ml), stirred for 30 min and filtered through Speedex, the filtrate concentrated, suspended between TBME and 1 N NaOH, stirred for 12 h and again filtered through Speedex. The organic phase was washed with aq Na$_2$CO$_3$, H$_2$O and brine, dried over MgSO$_4$ and concentrated to give 13.57 g brown solid which was recrystallised from heptane (100 ml) to give 6.94 g of product (93% pure by quantitative hplc) as a yellow solid m.p. 120° C.;

IR (NJL): 3305 m (NH), 1637s (C═O); MS(EI): 303 ([M+H]$^+$); 1H NMR (DMSO) 1.06 (s, 9H), 2.10 (s, 3H), 7.18–7.32 (m, 4H), 7.45 (s, 1H), 7.61 (bs, 1H), 8.46 (s, 1H).

The residue from the above recrystallisation was continuously extracted with TBME for 16 h and combined with the mother liquor, concentrated and recrystallised three times from heptane to give a further 0.71 g of product (91% pure by quant. hplc). Total yield: 54%.

c) N-tert.-Butyl-6-morpholin-4-yl-4-o-tolyl-nicotinamide

A mixture of 6.0 g (19 mMol) of N-tert.-butyl-6-chloro-4-o-tolyl-nicotinamide and 12 ml (138 mMol) morpholine was heated at 100° C. for 4 hours. After cooling to room temperature, extractive work-up with ethyl acetate, water and brine yielded 6.3 g (91%) of N-tert.-butyl-6-morpholin-4-yl-4-o-tolyl-nicotinamide as a brown crystalline foam.

MS (ISP): 376 (M+Na$^+$, 8), 254 (M+H$^+$, 100).

Alternatively 92 ml (92 mMol) o-Tolylmagnesium chloride solution (1M in THF) were added over 15 minutes to a solution of 5.0 g (23 mMol) N-tert.-butyl-6-chloro-nicotinamide in 25 ml THF cooled to 0° C. The reaction mixture was stirred 18 hours at 30° C. and cooled again to 0° C. 5.6 ml (138 mMol) Methanol were added over 30 minutes, stirring was pursued for 10 minutes and 6.2 g (25 mMol) o-chloranil were added. After 30 minutes at room temperature, the green solution was concentrated under reduced pressure to a green-black foam. This residue was suspended in 48.8 ml morpholine and stirred at 100° C. for 30 minutes. After cooling to 50° C., 100 ml tert.-butyl-methylether were added and the suspension further cooled to room temperature. After 30 minutes at room temperature, it was filtered, the precipitate was washed with tert.-butyl-methylether and the filtrate was poured onto 50 ml aqueous NaOH 1N. The phases were separated and the aqueous phase was extracted with tert.-butyl-methylether. The combined organic extracts were washed with deionized water and brine, dried (Na$_2$SO$_4$) and concentrated under reduced pressure to yield 6.2 g (75%) N-tert.-butyl-6-morpholin-4-yl-4-o-tolyl-nicotinamide as a brown resin.

MS (ISP): 376 (M+Na$^+$, 6), 354 (M+H$^+$, 100).

d) 6-Morpholin-4-yl-4-o-tolyl-nicotinamide

A mixture of 6.0 g (16.5 mMol) N-tert.-butyl-6-morpholin-4-yl-4-o-tolyl-nicotinamide and 12 ml (185 mMol) methanesulfonic acid was stirred at 100° C. for 5 hours, then poured on ice. The aqueous phase was extracted with tert.-butyl-methylether, brought to pH=10 with NaOH aq. 28% and extracted further with tert.-butyl-methylether. The second organic extracts were dried (Na$_2$SO$_4$) and concentrated to yield 4.75 g (96%) 6-morpholin-4-yl-4-o-tolyl-nicotinamide as a light beige crystalline foam.

MS (ISP): 320 (M+Na$^+$, 5), 298 (M+H$^+$, 100).

Alternatively 0.5 g (1.29 mMol) N-Benzyl-6-morpholin-4-yl-4-o-tolyl-nicotinamide was dissolved in 2.5 ml methanesulfonic acid and 0.25 ml sulfuric acid and heated to 100° C. for 1 hour. A second portion of 0.25 ml sulfuric acid was added and heating was pursued for 22 hours. After cooling to room temperature, the reaction mixture was poured onto 75 ml aqueous saturated sodium carbonate, cooled with ice and extracted with ethyl acetate. The combined organic extracts were washed with aqueous saturated sodium carbonate and brine, dried (Na$_2$SO$_4$) and concentrated. The residue was flash chromatographed (eluent: dichloromethane/methanol 95:5) to yield 0.15 g (39%) 6-morpholin-4-yl-4-o-tolyl-nicotinamide as a yellow resin.

MS (EI): 297 (M$^+$, 73), 266 (100), 252 (44), 240 (72).

e) (6-Morpholin-4-yl-4-o-tolyl-pyridin-3-yl)-carbamic Acid Methyl Ester 9.9 ml (53.7 mMol) Sodium methoxide solution (5.4 M in MeOH) were added over 15 minutes to a solution of 3.9 g (21.5 mMol) N-bromosuccinimide in 22.5 ml dichloromethane cooled to −5° C. The milky suspension was stirred at −5° C. for 18 hours, then, at the same temperature, a solution of 4.5 g (14 mMol) 6-morpholin-4-yl-4-o-tolyl-nicotinamide in 22.5 ml dichloromethane was added over 15 minutes. After 5 hours at 5° C., 33 ml (33 mMol) aqueous HCl 1N were added, the phases were separated, the organic phase washed with water and the aqueous phases extracted with dichloromethane. The combined organic phases were dried (Na$_2$SO$_4$) and evaporated. The residue was treated with basic Alox (1:1 weight) in ethyl acetate/heptane 1:1 for 30 minutes at room temperature. After filtration and removal of the solvents, the residue was crystallized from di-iso-propylether/n-heptane 1:2 at 0° C. to yield 3.4 g (72.5%) (6-morpholin-4-yl-4-o-tolyl-pyridin-3-yl)-carbamic acid methyl ester as a yellow powder.

MS (ISP): 350 (M+Na$^+$, 3), 328 (M+H$^+$, 100), 296 (M—MeO, 13).

f) Methyl-(6-morpholin-4-yl-4-o-tolyl-pyridin-3-yl)-amine

A solution of 3.0 g (9.1 mMol) (6-morpholin-4-yl-4-o-tolyl-pyridin-3-yl)-carbamic acid methyl ester in 15 ml toluene was added at room temperature over 15 minutes to a solution of 13 ml (46 mMol) Red-Al® (70% in toluene) and 15 ml toluene. After 2 hours at 50° C., the reaction mixture was cooled to 0° C. and 25.5 ml aqueous NaOH 1N were added over 10 minutes (very exothermic). The phases were separated and the aqueous phase extracted with toluene. The combined organic extracts were washed with water and brine, dried (Na$_2$SO$_4$) and evaporated. The residue was crystallized from n-heptane at −10° C. to yield 2.3 g (88%) methyl-(6-morpholin-4-yl-4-o-tolyl-pyridin-3-yl)-amine as a light beige powder of m.p.=73.5–76° C.

MS (ISP): 284 (M+H$^+$, 100).

g) 2-(3,5-bis-Trifluoromethyl-phenyl)-N-methyl-N-(6-morpholin-4-yl-4-o-tolyl-pyridin-3-yl)-isobutyramide A solution of 1.2 g (3.8 mMol) 2-(3,5-bis-trifluoromethyl-phenyl)-2-methyl-propionyl chloride and 0.5 ml dichloromethane were added dropwise over 15 minutes at 0° C. to a solution of 1.0 g (3.5 mMol) methyl-(6-morpholin-4-yl-4-o-tolyl-pyridin-3-yl)-amine and 0.85 ml (4.9 mMol) N-ethyl-di-isopropylamine in 7.0 ml dichloromethane. The reaction mixture was stirred 2.5 hours at 0° C., poured onto 8 ml deionized water and stirred further 30 minutes at room temperature. The phases were separated and the aqueous phase extracted with dichloromethane. The organic extracts were washed with deionized water, aqueous sodium hydroxide 2% and aqueous sodium bicarbonate 5%, dried (Na$_2$SO$_4$) and concentrated under reduced pressure. The residue was crystallized from ethanol at −20° C. to yield 1.27 g (64%) 2-(3,5-bis-trifluoromethyl-phenyl)-N-methyl-N-(6-morpholin-4-yl-4-o-tolyl-pyridin-3-yl)-isobutyramide as a white powder. Concentration of the mother-liquors gave 0.77 g of a slowly crystallizing brown oil which can be further purified.

MS (ISP): 588 (M+Na$^+$, 12), 566 (M+H$^+$, 100).

EXAMPLE 81

6-Chloro-N,N-diethyl-4-o-tolyl-nicotinamide a) 6-Chloro-N,N-diethyl-nicotinamide 0.51 ml (6.98 mMol) Thionylchloride and 10 µl DMF were added to a suspension of 1.0 g (6.34 mMol) 6-chloronicotinic acid in 5 ml tetrahydrofuran. The reaction mixture was stirred at 65° C. for 1.5 hours, cooled to 0° C. and 1.98 ml (19.0 mMol) diethylamine were added over 40 minutes. The resulting suspension was stirred 4 hours at room temperature and 1 hour at 60° C. After cooling to room temperature, 5.0 ml aqueous NaOH 2N were added and stirring pursued for 30 minutes. The system was diluted with 25 ml deionized water and 20 ml ethyl acetate. The phases were separated and the aqueous phase was further extracted with ethyl acetate. The combined organic extracts were washed with aqueous NaOH 1N and half-saturated aqueous NaCl, dried ($Na_2SO_4$) and evaporated to yield 0.68 g (50%) 6-chloro-N,N-diethyl-nicotinamide as a yellow oil.

MS (ISP): 425 ($2M+H^+$, 82), 230 ($M+NH_4^+$, 62), 213 ($M+H^+$, 100).

b) 6-Chloro-N,N-diethyl-4-o-tolyl-nicotinamide 7.62 ml (7.62 mMol) o-Tolylmagnesium chloride solution (1M in THF) were added over 15 minutes to a solution of 0.60 g (2.54 mMol) 6-chloro-N,N-diethyl-nicotinamide in 3.0 ml THF cooled to 0° C. The reaction mixture was stirred 2 hours at room temperature, then cooled again to 0° C. and 0.41 ml methanol (10.1 mMol) were added followed by 692 mg 2,3-dichloro-5,6-dicyano-1,4-benzoquinone (3.1 mMol). After stirring 2 hours at room temperature, the reaction mixture was concentrated under reduced pressure and 50 ml t-butyl-methylether were added at 50° C. The resulting suspension was filtered off, the filtrate was concentrated and the residue was purified by flash chromatography (eluent:ethyl acetate/n-heptane 1:1) to yield 0.67 g (86%) of 6-chloro-N,N-diethyl-4-o-tolyl-nicotinamide as a yellow oil.

MS (EI): 301 (M–H, 10); 267 (M—Cl, 6); 230 (M—$Et_2N$, 100); 166 (31).

EXAMPLE 82

N-tert.-Butyl-6-methyl-4-o-tolyl-nicotinamide a) N-tert.-Butyl-6-methyl-nicotinamide 3.5 ml (40 mMol) Oxalylchloride and 57.4 µl (0.74 mMol) DMF were added to a suspension of 5.0 g (36.5 mMol) 6-methyl-nicotinic acid in 25 ml toluene and the system was heated to 40° C. for one hour. After diluting with 20 ml toluene and cooling to 0° C., 11.5 ml (109 mMol) tert.-butylamine were slowly added. After 30 minutes stirring at room temperature, 25 ml aqueous NaOH 2N were added and stirring pursued for 30 minutes. The phases were separated and the aqueous phase was extracted with toluene. The combined organic extracts were washed with water and brine, dried ($Na_2SO_4$) and concentrated. The residue was purified by flash chromatography (eluent:ethyl acetate/n-heptan 1:1) to yield 5.4 g (77%) N-tert.-butyl-6-methyl-nicotinamide as a light beige solid of m.p.=103.5–104.8° C.

MS (EI): 192 ($M^+$, 22), 177 ($M^+$—$CH_3$, 27), 120 ($M^+$—NHtBu, 100).

b) N-tert.-Butyl-6-methyl-4-o-tolyl-nicotinamide 38.9 ml (38.9 mMol) o-Tolylmagnesium chloride solution (1M in THF) were added over 15 minutes to a solution of 2.5 g (10.1 mMol) N-tert.-butyl-6-methyl-nicotinamide in 12.5 ml THF cooled to 0° C. The suspension obtained was stirred overnight at room temperature, then one more hour at 50° C. After cooling to 0° C., 2.1 ml (51.9 mMol) methanol were added over 30 minutes (exothermic!), followed after 10 minutes by 3.5 g (15.6 mMol) 2,3-dichloro-5,6-dicyano-benzoquinone. After one hour at room temperature, the reaction mixture was concentrated under reduced pressure to a still stirrable oil, heated to 50° C. and 100 ml tert.-butyl-methylether were added. The suspension was stirred 30 minutes at reflux, 1 hour at room temperature and filtered. The filtrate was evaporated and the residue was purified by flash chromatography (50 g $SiO_2$, eluent:AcOEt/n-heptane 2:1) to yield 3.1 g (84.5%) N-tert.-butyl-6-methyl-4-o-tolyl-nicotinamide as a light brown resinous solid.

MS (EI): 282 ($M^+$, 11), 210 ($M^+$—NHtBu, 100).

EXAMPLE 83

N-tert-Butyl-6-chloro-4-(prop-2-yl)-nicotinamide 7.0 ml (14.1 mMol) iso-Propylmagnesium chloride solution (2M in THF) were added over 5 minutes to a solution of 1.0 g (4.7 mMol) N-tert.-butyl-6-chloro-nicotinamide in 5.0 ml THF cooled to 0° C. and the reaction mixture was stirred 18 hours at room temperature. After cooling to 0° C., 1.14 ml (28.2 mMol) methanol were added over 10 minutes, followed, after 15 minutes, by 1.17 g (5.2 mMol) 2,3-dichloro-5,6-dicyano-1,4-benzoquinone. After stirring 30 minutes at room temperature, the red-brown solution was concentrated under reduced pressure to about 10 g, heated to 50° C. and 20 ml tert.-butyl-methylether were added. The resulting suspension was stirred 1 hour at 55° C., then 1 hour at room temperature and filtered. The filtrate was concentrated under reduced pressure and digested in 9 ml n-hexane/ethyl acetate 4:1 to yield 0.67 g (56%) N-tert.-butyl-6-chloro-4-(prop-2-yl)-nicotinamide as a beige powder of m.p.=130–140° C. (dec.)

MS (EI): 254 ($M^+$, 51), 198 ($M^+$—$C_4H_8$, 38), 182 ($M^+$—NHtBu, 100).

EXAMPLE 84

N-tert.-Butyl-6-chloro-4-p-fluoro-phenyl-nicotinamide 14.1 ml (14.1 mmol) 4-Fluoro-phenylmagnesium chloride solution (1M in THF) were added over 10 minutes to a solution of 1.0 g (4.7 mMol) N-tert.-butyl-6-chloro-nicotinamide in 5.0 ml THF cooled to 0° C. and the reaction mixture was stirred 18 hours at 35° C. After cooling to 0° C., 1.14 ml (28.2 mMol) methanol were added over 20 minutes, followed, after 15 minutes, by 1.17 g (5.2 mMol) 2,3-dichloro-5,6-dicyano-1,4-benzoquinone. After 30 minutes at room, temperature, the brown solution was concentrated under reduced pressure to about 10 g, heated to 50° C. and 20 ml tert.-butyl-methylether were added. The resulting suspension was stirred 1 hour at 55° C., then 1 hour at room temperature and filtered. The filtrate was concentrated under reduced pressure and digested in 5 ml n-hexane/ethyl acetate 4:1 to yield 0.69 g (48%) N-tert.-butyl-6-chloro-4-p-fluoro-phenyl-nicotinamide as a light brown powder of m.p.= 168–173° C.

MS (ISP): 307 ($M+H^+$, 100).

Example A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition are manufactured:

|  | mg/capsule |
|---|---|
| Active substance | 10 |
| Lactose | 155 |
| Corn starch | 30 |

-continued

|  | mg/capsule |
|---|---|
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

Example C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

What is claimed is:

1. A compound of the formula

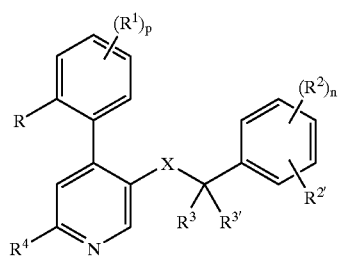

wherein

R is lower alkyl, lower alkoxy, halogen or trifluoromethyl;

$R^1$ is halogen or hydrogen; and when p is 1, $R^1$ may in addition to the above substituents be taken together with R to form —CH=CH—CH=CH—;

$R^2$ and $R^{2'}$ are independently hydrogen, halogen, trifluoromethyl, lower alkoxy or cyano; and when n is 1, $R^2$ and $R^{2'}$ may in addition to the above substituents form —CH=CH—CH=CH—, unsubstituted or substituted by one or two substituents selected from lower alkyl or lower alkoxy;

$R^3$ and $R^{3'}$ are hydrogen, lower alkyl or taken together with the attached carbon atom form a cycloalkyl group;

$R^4$ is —N($R^5$)$_2$, —N($R^5$)(CH$_2$)$_n$OH, —N($R^5$)S(O)$_2$-lower alkyl, —N($R^5$)S(O)$_2$-phenyl, —N=CH—N($R^5$)$_2$,

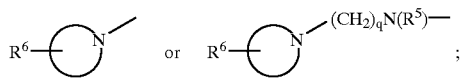

$R^5$ is hydrogen, $C_{3-6}$-cycloalkyl, benzyl or lower alkyl;

$R^6$ is hydrogen, hydroxy, lower alkyl, —(CH$_2$)$_n$COO—($R^5$), —N($R^5$)CO-lower alkyl, hydroxy-lower alkyl, —(CH$_2$)$_n$CN, —(CH$_2$)$_n$O(CH$_2$)$_n$OH, —CHO or a 5- or 6 membered heterocyclic ring containing from 1 to 4 heteroatoms, selected from the group consisting of oxygen, nitrogen, and sulfur, and with one of the carbon atoms in said ring being unsubstituted or substituted with an oxo group, which heterocyclic ring is directly bonded or bonded via an alkylene group to the remainder of the molecule;

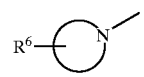

is a cyclic tertiary amine which may contain one additional heteroatom selected from the group consisting of oxygen, nitrogen, or sulfur, wherein any sulfur present in the ring is thio or can be oxidized to sulfoxide or sulfur dioxide by which said cyclic tertiary amine is directly attached to the remainder of the molecule or is attached through the linker —(CH$_2$)$_n$N($R^5$)—;

X is —C(O)—N($R^5$)—;

n, p and q are 1 to 4; and m is 1 or 2;

or pharmaceutically acceptable acid addition salts thereof.

2. A compound of claim 1 wherein X is —C(O)N($R^5$)—.

3. A compound of claim 1 wherein $R^4$ is

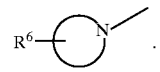

4. A compound of claim 3 wherein $R^4$ is a six-membered ring.

5. A compound of claim 4 wherein $R^4$ is unsubstituted or substituted piperazinyl.

6. A compound of claim 5 which is N-(3,5-bis-trifluoromethyl-benzyl)-N-methyl-6-(4-methyl-piperazin-1-yl)-4-o-tolyl-nicotinamide.

7. A compound of claim 5 which is N-(3,5-bis-trifluoromethyl-benzyl)-4-(2-chloro-phenyl)-N-methyl-6-(4-methyl-piperazin-1-yl)-nicotinamide.

8. A compound of claim 5 which is 4-{5-[(3,5-bis-trifluoromethyl-benzyl)-methyl-carbamoyl]-4-o-tolyl-pyridin-2-yl}-piperazine-1-carboxylic acid.

9. A compound of claim 5 which is N-(3,5-bis-trifluoromethyl-benzyl)-N-methyl-6-(4-propyl-piperazin-1-yl)-4-o-tolyl-nicotinamide.

10. A compound of claim 5 which is N-(3,5-bis-trifluoromethyl-benzyl)-N-methyl-6-piperazin-1-yl-4-o-tolyl-nicotinamide.

11. A compound of claim 5 which is N-(3,5-bis-trifluoromethyl-benzyl)-6-[4-(2-hydroxy-ethyl)-piperazin-1-yl]-N-methyl-4-o-tolyl-nicotinamide.

12. A compound of claim 5 which is N-(3,5-bis-trifluoromethyl-benzyl)-6-(4-cyanomethyl-piperazin-1-yl)-N-methyl-4-o-tolyl-nicotinamide.

13. A compound of claim 5 which is N-(3,5-bis-trifluoromethyl-benzyl)-6-{4-[2-(2-hydroxy-ethoxy)-ethyl]-piperazin-1-yl}-N-methyl-4-o-tolyl-nicotinamide.

14. A compound of claim 5 which is N-(3,5-bis-trifluoromethyl-benzyl)-N-methyl-6-(4-[1,2,4]oxadiazol-3-ylmethyl-piperazin-1-yl)-4-o-tolyl-nicotinamide.

15. A compound of claim 5 which is N-(3,5-bis-trifluoromethyl-benzyl)-6-(4-formyl-piperazin-1-yl)-N-methyl-4-o-tolyl-nicotinamide.

16. A compound of claim 5 which is N-(3,5-bis-trifluoromethyl-benzyl)-N-methyl-6-[4-(1H-tetrazol-5-ylmethyl)-piperazin-1-yl]-4-o-tolyl-nicotinamide.

17. A compound of claim 4 wherein $R^4$ is morpholino or substituted morpholino.

18. A compound of claim 17 which is N-(3,5-bis-trifluoromethyl-benzyl)-N-methyl-6-morpholin-4-yl-4-o-tolyl-nicotinamide.

19. A compound of claim 17 which is N-(2-methoxy-benzyl)-N-methyl-6-morpholin-4-yl-4-o-tolyl-nicotinamide.

20. A compound of claim 17 which is N-(5-chloro-2-methoxy-benzyl)-N-methyl-6-morpholin-4-yl-4-o-tolyl-nicotinamide.

21. A compound of claim 17 which is N-(2-chloro-5-methoxy-benzyl)-N-methyl-6-morpholin-4-yl-4-o-tolyl-nicotinamide.

22. A compound of claim 17 which is N-(2-chloro-5-methoxy-benzyl)-N-methyl-6-morpholin-4-yl-4-o-tolyl-nicotinamide.

23. A compound of claim 17 which is N-[2-methoxy-5-(5-trifluoromethyl-tetrazol-1-yl)-benzyl]-N-methyl-6-morpholin-4-yl-4-o-tolyl-nicotinamide.

24. A compound of claim 4 wherein $R^4$ is thiomorpholino or oxidized thiomorpholino.

25. A compound of claim 24 which is N-(3,5-bis-trifluoromethyl-benzyl)-N-methyl-6-thiomorpholin-4-yl-4-o-tolyl-nicotinamide.

26. A compound of claim 24 which is N-(3,5-bis-trifluoromethyl-benzyl)-N-methyl-6-(1-oxo-1$\lambda^4$-thiomorpholin-4-yl)-4-o-tolyl-nicotinamide.

27. A compound of claim 24 which is N-(3,5-bis-trifluoromethyl-benzyl)-6-(1,1-dioxo-1$\lambda^6$-thiomorpholin-4-yl)-N-methyl-4-o-tolyl-nicotinamide.

28. A compound of claim 4 wherein $R^4$ is unsubstituted or substituted piperidinyl.

29. A compound of claim 28 which is 5'-[(3,5-bis-trifluoromethyl-benzyl)-methyl-carbamoyl]-4'-o-tolyl-3,4,5,6-tetrahydro-2H-[1,2']bipyridinyl-4-carboxylic acid.

30. A compound of claim 3 wherein $R^4$ is a five-membered ring.

31. A compound of claim 30 wherein $R^4$ is unsubstituted or substituted pyrrolidinyl.

32. A compound of claim 30 which (RS)-6-[3-(acetyl-methyl-amino)-pyrrolidin-1-yl]-N-(3,5-bis-trifluoromethyl-benzyl)-N-methyl-4-o-tolyl-nicotinamide.

33. A compound of claim 3 wherein $R^4$ is attached through the linker —$(CH_2)_nN(R_5)$—.

34. A compound of claim 33 which is N-(3,5-bis-trifluoromethyl-benzyl)-N-methyl-6-[methyl-(2-morpholin-4-yl-ethyl)-amino]-4-o-tolyl-nicotinamide.

* * * * *